United States Patent
Nichols et al.

(10) Patent No.: US 11,884,945 B2
(45) Date of Patent: *Jan. 30, 2024

(54) METHODS FOR PURIFICATION OF ARYLSULFATASE A

(71) Applicant: Takeda Pharmaceutical Company Limited, Osaka (JP)

(72) Inventors: Dave Nichols, Lexington, MA (US); Igor Quinones-Garcia, Lexington, MA (US); Bee Lin Cheang, Lexington, MA (US); Mei Huei Jang, Lexington, MA (US)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/810,396

(22) Filed: Jul. 1, 2022

(65) Prior Publication Data

US 2023/0235303 A1    Jul. 27, 2023

Related U.S. Application Data

(63) Continuation of application No. 14/759,645, filed as application No. PCT/US2014/010856 on Jan. 9, 2014, now Pat. No. 11,407,984.

(60) Provisional application No. 61/750,693, filed on Jan. 9, 2013.

(51) Int. Cl.
*C12N 9/16* (2006.01)
*A61K 38/46* (2006.01)
*C12M 1/00* (2006.01)

(52) U.S. Cl.
CPC .............. *C12N 9/16* (2013.01); *A61K 38/465* (2013.01); *C12M 47/12* (2013.01); *C12Y 301/06001* (2013.01); *C12Y 301/06008* (2013.01)

(58) Field of Classification Search
CPC ........ C12N 9/16; A61K 38/465; C12M 47/12; C12Y 301/06001; C12Y 301/06008
See application file for complete search history.

(56) References Cited

U.S. PATENT DOCUMENTS

| | | |
|---|---|---|
| 6,197,507 B1 | 3/2001 | Berg et al. |
| 6,812,339 B1 | 11/2004 | Venter et al. |
| 7,232,670 B2 | 6/2007 | D'Azzo et al. |
| 8,536,315 B2 | 9/2013 | Fogh et al. |
| 2003/0199073 A1 | 10/2003 | Fogh et al. |
| 2004/0126370 A1 | 7/2004 | d'Azzo et al. |
| 2008/0003211 A1 | 1/2008 | Fogh et al. |
| 2009/0246187 A1 | 10/2009 | Nilsson |
| 2015/0353904 A1 | 12/2015 | Nichols et al. |

FOREIGN PATENT DOCUMENTS

| | | |
|---|---|---|
| EP | 0456229 A2 | 11/1991 |
| EP | 2943568 B1 | 11/2019 |
| JP | 2002-517516 A | 6/2002 |
| WO | WO 1999/037325 A2 | 7/1999 |
| WO | WO 1999/064462 A1 | 12/1999 |
| WO | WO 2000/067789 A1 | 11/2000 |
| WO | WO 2001/007065 A2 | 2/2001 |
| WO | WO 2002/040686 A2 | 5/2002 |
| WO | WO 2002/098455 A2 | 12/2002 |
| WO | WO 2002/099092 A2 | 12/2002 |
| WO | WO 2003/002731 A1 | 1/2003 |
| WO | WO 2003/029403 A2 | 4/2003 |
| WO | WO 2003/057179 A2 | 7/2003 |
| WO | WO 2003/066669 A2 | 8/2003 |
| WO | WO 2005/073367 A1 | 8/2005 |
| WO | WO 2005/094874 A1 | 10/2005 |
| WO | WO 2006/031560 A2 | 3/2006 |
| WO | WO 2007/112757 A2 | 10/2007 |
| WO | WO 2014/110246 A1 | 7/2014 |

OTHER PUBLICATIONS

Abzalimov et al., "Studies of pH-dependent self-association of a recombinant form of arylsulfatase A with electrospray ionization mass spectrometry and size-exclusion chromatography", Anal. Chem., 85(3): 1591-1596 (2013).
Aronson et al., "Lysosomal degradation of Asn-linked glycoprotein," The FASEB Journal, 3: 2615-2622 (1989).
Asenjo et al., "Protein purification using chromatography: selection of type, modelling and optimization of operating conditions", J Mol Recognit., 22(2): 65-76 (2009).
Auclair et al., "Intrathecal recombinant human 4-sulfatase reduces accumulation of glycosaminoglycans in dura of mucopolysaccharidosis VI cats," 2012. Translational Investigation. vol. 71. No. 1. 7 pages.
Austin et al., "Abnormal sulphatase activities in two human diseases (metachromatic leucodystrophy and gargoylism)," Biochem. J., 93: 15c-17c (1964).
Baum et al., "The assay of arylsulfatases A and B in human urine," Clin. Chim. Acta., 4: 453-455 (1959).
Ben-Yoseph et al., "The Interrelations between High- and Low-Molecular-Weight Forms of Normal and Mutant (Krabbe-Disease) Galactocerebrosidase," J. Biochem., 189: 9-15 (1980).
Berg et al., "Purification and characterization of Recombinant Human Lysosomal a-mannosidase," Molecular Genetics and Metabolism, 73: 18-29 (2001).
Bond et al., "Structure of a human lysosomal sulfatase," Structure, 5(2): 277-289 (1997).
Bostick et al., "Separation and Analysis of Arylsulfatase Isoenzymes in Body Fluids of Man," Clinical Chemistry, American Association for Clinical Chemistry, 24(8): 1305-1316 (1978).

(Continued)

*Primary Examiner* — Paul J Holland
(74) *Attorney, Agent, or Firm* — Proskauer Rose LLP; Fangli Chen

(57) ABSTRACT

The present invention provides, among other things, improved methods for purifying arylsulfatase A (ASA) protein produced recombinantly for enzyme replacement therapy. The present invention is, in part, based on the surprising discovery that recombinant ASA protein can be purified from unprocessed biological materials, such as, ASA-containing cell culture medium, using a process involving as few as four chromatography columns and only one step of post-chromatographic ultrafiltration/diafiltration.

16 Claims, 6 Drawing Sheets

Specification includes a Sequence Listing.

(56) References Cited

OTHER PUBLICATIONS

Branden et al., "Introduction to Protein Structure," Garland Publishing Inc., New York, p. 247 (1991).
Braulke et al., "Insulin-like Growth Factors I and II Stimulate Endocytosis but Do Not Affect Sorting of Lysosomal Enzymes in Human Fibroblasts," The Journal of Biological Chemistry, 265(12): 6650-6655 (1990).
Braulke et al., "Sulfated Oligosaccharides in Human Lysosomal Enzymes," Biochemical and Biophysical Research Communications, 143(1): 178-185 (1987).
Calias, P. et al., "CNS Penetration of Intrathecal-Lumbar Idursulfase in the Monkey, Dog and Mouse: Implications of Neurological Outcomes of Lysosomal Storage Disorder," 2012. PLoS One 7 (1). 13 pages.
Challener, "Challenges of Protein Aggregation during Purification", BioPharm Interanational, 27(9) (Sep. 2014), 4 pages.
Chen et al., "Galactocerebrosidase from human urine: purification and partial characterization," Biochimica et Biophysica Acta, 1170: 53-61 (1993).
Coenen et al., "Morphological alterations in the inner ear of the arylsulfatase A-deficient mouse," Acta Neuropathol, 101: 491-498 (2001).
Cummings et al., "Protein chromatography on hydroxyapatite columns", Methods Endymol., 163: 387-404 (2009).
Current Protocols in Protein Science, John Wiley & Sons, Inc., Unit 5.10 (1998). 41 pages.
Demeule et al., "High transcytosis of melanotransferrin (P97) across the blood-brain barrier," Journal of Neurochemistry, 83: 924-933 (2002).
D'Hooge et al., "Hyperactivity, neuromotor defects, and impaired learning and memory in a mouse model for metachromatic leukodystrophy," Brain Research, 907: 35-43 (2001).
Dierks et al., "Conversion of cysteine to formylglycine: A protein modification in the endoplasmic reticulum," Proc. Natl. Acad. Sci. USA, 94: 11963-11968 (1997).
Dunican et al., "Designing Cell-Permeant Phosphopeptides to Modulate Intracellular Signaling Pathways," Biopolymers (Peptide Science), 60: 45-60 (2001).
Farooqui et al., "Isolation, Characterization and the Role of Rabbit Testicular Arylsulphatase A in Fertilization," Biochem. J., 181: 331-337 (1979).
Fluharty et al., "[58] Arylsulfatases A and B from Human liver," Meth. Enzymol., 50: 537-547 (1978).
Franco et al., "A Cluster of Sulfatase Genees on Xp22.3: Mutations in Chrondrodysplasia Punctata (CDPX) and Implications for Warfarin Embryopathy," Cell, 81: 15-25 (1995).
Gieselmann et al., "Arylsulfatase A pseudodeficiency: Loss of a polyadenylylation signal and N-glycosylation site," Proc. Natl. Acad. Sci. USA, 86(9436-9440 (1989).
Gieselmann et al., "In Vitro Mutagenesis of Potentioal N-Glycosylation Sites of Arylsulfatase A," Journal of Biological Chemistry, 267(19): 13262-13266 (1992).
Gieselmann et al., Metaachromatic leukodystrophy: consequences of sulphatide accumulation, Acta Paediatr Suppl., 443: 74-79 (2003).
Gieselmann et al., "Metachromatic leukodystrophy: Molecular genetics and an animal model," J. Inher. Metab. Dis., 21: 564-574 (1998).
Gomori, G., "Preparation of Buffers for Use in Enzyme Studies," Methods in Enzymology, p. 136-146 (1955).
Hallmann et al., "An inducible arylsulfatase of Volvox carteri with properties suitable for a reporter-gene system," Eur. J. Biochem., 221: 143-150 (1994).
Hess et al., "Phenotype of arylsufatase A-deficient mice: Relationship to human metachromatic leukodystrophy," Proc. Natl. Acad. Sci. USA, 93: 14821-14826 (1996).
Hess, et al., "Isolation and comparison of arylsulfatase A from rat liver and Morris hepatoma 7777," Eur. J. Biochem., 135: 505-509 (1983).

Hift et al., "Variegate porphyria in South Africa, 1688-1996—new developments in an old disease," S. Afr. Med. J., 87(6): 722-731 (1997).
Ho et al., "Synthetic Protein Transduction Domains: Enhanced Transduction Potential in Vitro and in Vivo," Cancer Research, 61: 474-477 (2001).
Ida et al., "Pathological and biochemical studies of fetal Krabbe disease," Brain & Development, 16: 480-484 (1994).
International Search Report for PCT/US2012/045927, 7 pages, (dated Nov. 1, 2013.).
International Search Report and Written Opinion for PCT/US2014/010856, 10 pages (dated Mar. 25, 2014).
James, Gordon T., "Essential Arginine Residues in Human Liver Arylsulfatase A," Archives of Biochemistry and Biophysics, 197(1): 57-62 (1979).
Jordon et al., "Purification, crystallization and properties of porphobilinogen deaminase from a recombiant strain of *Escherichia coli* K12," Biochem, 254: 427-435 (1988).
Kakkis et al., Abstract only, Abstract No. 281-0, "A Method to Reduce the Immune REsponse to Enzyme Replacement Therapy: Studies of Criteria for Success," J. Inherit. Metab. Dis., 26(2) (2003). 1 page.
Kakkis et al., Abstract only, Abstract No. 282-0, "Effective Reduction of Lysosomal Storage in Brain and Meninges Following Intrathecal Administration of Iduronidase in Canine Mucopolysaccharidosis I (MPS I)," J. Inherit. Metab. Dis. 26(2) (2003). 1 page.
Kaneda et al., "Regional assignment of five genes of human chromosome 19," Chromosoma (BerJ), 95: 8-12 (1987).
Kelly et al., "Presence of a lysosomal enzyme, arylsulfatase-A, in the prelysosome-endosome compartments of human cultured fibroblasts," European Journal of Cell Biology, 48: 71-78 (1989).
Kling, "Highly Concentrated Protein Formulations: Finding Solutions for the next Generation of Parenteral Biologics"; BioProcess International, 12(5) (May 2014), 10 pages.
Kudoh et al., "Diagnosis of Metachromatic Leukodystrophy, Krabbe Disease, and Farber Disease after Uptake of Fatty Acid-labeled Cerobroside Sulfate into Cultured Skin Fibroblasts," J. Clin. Invest., 70: 89-97 (1982).
Lee et al., "Evidence for an Essential Histidine Residue in Rabbit Liver Aryl Sulfatase A," Archives of Biochemistry and Biophysics, 171: 424-434 (1975).
Liao et al., "Cloning, Expression, Purification and Characterization of the Human Blood Specificity Lysosomal Acid a-Mannosidase," The Journal of Biological Chemistry, 271(45): 28348-28358 (1996).
Lindgren et al., "Cell-penetrating peptides," TIPS, 21: 99-103 (2000).
Lukatela et al., "Crystal Structure of Human Arylsufatase A: The Aldehyde Function and the Metal Ion at the Active Site Suggest a Novel Mechanism for Sulfate Ester Hydrolysis," Biochemistry, 37: 3654-3664 (1998).
Lüllmann-Rauch et al., "Lysosomal sulfoglycolipid storage in the kidneys of mice deficient for arylsulfatase A (ASA) and of double-knockout mice deficient for ASA and galactosylceramide synthase," Histochem Cell Biol., 116: 161-169 (2001).
Matsushima et al., "Absence of MHC Class II Molecules Reduces CNS Demyelination, Microglial/Macrophage Infiltration, and Twitching in Murine Globoid Cell Leukodystrophy," Cell, 78: 645-656 (1994).
Matzner et al., "Bone marrow stem cell-based gene transfer in a mouse model for metachromatic leukodystrophy: effects on visceral and nervous system disease manifestations," Gene Therapy, 9: 53-63 (2002).
Matzner et al., "Enzyme replacement improves nerve system pathology and function in a mouse model for metachromatic leukodystrophy," Human Molecular Genetics, 14: 1139-1152 (2005).
Matzner et al., "Long-term expression and transfer of arylsulfatase A into brain of arylsulfatase A-deficient mice transplanted with bone marrow expressing the arylsulfatase A cDNA from a retroviral vector," Gene Therapy, 7: 1250-1257 (2000).
Matzner et al., "Retrovirally expressed human arylsulfatase A corrects the metabolic defect of arylsulfatase A-deficient mouse cells," Gene Therapy, 7: 805-812 (2000).

(56) References Cited

OTHER PUBLICATIONS

Meissner et al., "Allosteric Inhibition of Human Lymphoblast and Purified Porphobilinogen Deaminase by Protoporphyrinogen and Coproporphyrinogen," J. Clin. Invest., 91: 1436-1444 (1993).
Meissner et al., "Protoporphyrinogen oxidase and porphobilinogen deaminase in variegate porphyria," European Journal of Clinical Investigation, 16: 257-261 (1986).
Millipore, "Protein Concentration and Diafiltration by Tangential Flow Filtration," Millipore Corporation, Billerica, MA 01821, USA (2003). 24 pages.
Muschol et al., "Secretion of phosphomannosyl-deficient arylsulphatase A and cathepsin D from isolated human macrophages," Biochem J., 368: 845-853 (2002).
Nebes et al., "Human Lysosomal Alpha-Mannosidase: Isolation and Nuceotide Sequence of the Full-Length cDNA," Biochemical and Biophysical Research Communications, 200(1): 239-245 (1994).
Nilssen et al., "a-Mannosidosis: functional cloning of the lysosomal a-mannosidase cDNA and identification of a mutation in two affected siblings," Human Molecular Genetics, 6(5): 717-726 (1997).
Pan et al., "TNF α Transport across the Blood-Brain Barrier is Abolished in Receptor Knockout Mice," Experimental Neurology, 174: 193-200 (2002).
Pan et al., "Upregulation of the Transport System for TNF α at the Blood-Brain Barrier," Archives of Physiology and Biochemistry, 109(4): 350-353 (2001).
Pearson et al., "Improved tools for biological sequence comparison," Procl Natl Acad Sci USA, 85: 2444-2448 (1988).
Pearson, William R., "(5) Rapid and Sensitive Sequence Comparison with FASTP and FASTA," Methods of Enzymology, 183: 63-98 (1990).
Perusi et al., "A novel mutation which represents the fifth non-pathogenic polymorphism in the coding sequence of the Arylsulfatase A gene," Molecular and Cellular Probes, 11: 449-451 (1997).
Peters et al., "Phylogenetic Conservation of Arylsulfatases," The Journal of Biological Chemistry, 265(6): 3374-3381 (1990).
Pezzini, J et al., "Comparative Study of strong anion exchangers: Structure-related chromatographic performances," Journal of Chromatography B. 877. p. 2443-2450 (2009).
Pohl, Thomas, "(7) Concentration of Proteins and Removal of Solutes," Methods in Enzymology, 182: 68-83 (1990).
Protein Purification Handbook, GE Healthcare (Oct. 2001). 96 pages.
Rafi et al., "Disease-causing mutations in cis with teh common arylsulfatase A pseudodeficiency allele compound the difficulties in accurately identifying patients and carriers of metachromatic leukodystrophy," Molecular Genetics and Metabolism, 79: 83-90 (2003).
Ricketts et al., "The R496H Mutation of Arylsulfatase A Does Not Cause Metachromatic Leukodystrophy," Human Mutation, 12: 238-239 (1998).
Riise et al., Genomic Structure of the Human Lysosomal a-Mannosidase Gene (MANB), Genomics, 42: 200-207 (1997).
Rodman et al., "Circulating natural IgM antibodies and their corresponding human cord blood cell-derived Mabs specifically combat the Tat protein of HIV," Experimental Hematology, 29: 1004-1009 (2001).
Rothenberger et al., "Coincident expression and distribution of melanotransferrin and transferring receptor in human brain capillary endothelium," Brain Research, 712: 117-121 (1996).
Sakai et al., "Purification and Characterization of Galactocerebrosidase from Human Lymphocytes," J. Biochem, 116(3): 615-620 (1994).
Sandhoff et al., "Kidney Sulfatides in Mouse Models of Inherited Glycosphingolipid Disorders," The Journal of Biological Chemistry, 277(23): 20386-20398 (2002).
Sangalli et al., "Transduced Fibroblasts and Metachromatic Leukodystrophy Lymphocytes Transfer Arylsulfatase A to Myelinating Glia and Deficient Cells In Vitro," Human Gene Therapy, 9: 2111-2119 (1998).
Sarafian et al., "Studies on the Charge Isomers of Arylsulfatase A," Biochemical Medicine, 33: 372-380 (1985).
Schmidt et al., "A Novel Amino Acid Modification in Sulfatases That is Defective in Multiple Sulfatase Deficiency," Cell, 82: 271-278 (1995).
Schröder et al., "Site-specific analysis of N-linked oligosaccharides of recombinant lysosomal arylsufatase A produced in different cell lines," Glycobiology, 20(2): 248-259 (2010).
Schuchman et al., "Human Arylsulfatase B: MOPAC Cloning, Nucleotide Sequence of a Full-Length cDNA, and Regions of Amino Acid Identity with Arylsulfatases A and C," Genomics, 6: 149-158 (1990).
Schwarze et al., "Protein transduction: unrestricted delivery into all cells?," trends in Cell Biology, 10: 290-295 (2000).
Scott et al., "Differential Staining of Acid Glycosaminoglycans (Mucopolysaccharides) by Alcian Blue in Salt Solutions," Histochemie, 5: 221-233 (1965).
Selmer et al., "The evolutionary conversation of a novel protein modification, the conversion of cysteine to serinesemialdehyde in arylsulfatase from Volvox carteri," Eur. J. Biochem., 238: 341-345 (1996).
Sevin et al., "Intracerebral adeno-associated virus-mediated gene transfer in rapidly progressive forms of metachromatic leukodystrophy," Human Molecular Genetics, 15(1): 53-64 (2006).
Shire et al., "Challenges in the Development of High Protein Concentration Formulations," Journal of Pharmaceutical Sciences, 93(6): 1390-1402 (2004).
Sofer et al., "Preparative chromatographic separation in pharmacuetical, diagnostic, and biotechnology industries: current and future trends," J. Chromatogr. A., 707(1): 23-28 (1995).
Sommerlade et al., "Four monoclonal antibodies inhibit the recognition of arylsulphatase A by the lysosomal enzyme phosphotransferase," Biochem J., 297: 123-130 (1994).
Stein et al., "Cloning and Expression of Human Arylsulfatase A," The Journal of Biological Chemistry, 264(2): 1252-1259 (1989).
Stevens et al., "Purification and Properties of Arylfulfatase A from Human Urine," The Journal of Biological Chemistry, 250(7): 2495-2501 (1975).
Thompson et al., "CIUSTAI W: improving the sensitivity of progressive multiple sequence alignment through sequence weighting, position-specific gap penalties and weight matrix choice," Nucleic Acids Research, 22(22): 4673-4680 (1994).
Tollersrud et al., "Purification of bovine lysosomal a-mannosidase, characterization of its gene and determination of two mutations that cause a-mannosidosis," Eur. J. Biochem, 246: 410-419 (1997).
Treuheit et al., "Inverse Relationship of Protein Concentration and Aggregation," Pharmaceutical Research, 19(4): 511-516 (2002).
Von Bulow, R. et al., "Defective Oligomerization of Arylsulfastase A as a Cause of Its Instability in Lysosomes and Metachromatic Leukodystrophy," 2022. The Journal of Biological Chemistry. vol. 277, No. 11, pp. 9455-9461.
Wada et al., "Microglial activation precedes acute neurodegeneration in Sandhoff disease and is suppressed by bone marrow transplantation," Proc. Natl. Acad Sci. (USA), 97(20): 10954-10959 (2000).
Waheed et al., "Phosphorylation and sulfation of arylsulfatase A accompanies biosynthesis of the enzyme in normal and carcinoma cell lines," Biochimica et Biophysica Acta, 847: 53-61 (1985).
Wang et al., "Erythropoietin production from CHO cells grown by continuous culture in a fluidized-bed bioreactor," Biotechnol. Bioeng., 77(2): 194-203 (2002).
Wittke et al., "Lysosomal sulfatide storage in the brain of arylsulfatase A-deficient mice: cellular alterations and topographic distribution," Acta Neuropathol, 108: 261-271 (2004).
Wu et al., "Neuroprotection with noninvasive neurotrophin delivery to the brain," Proc. Natl. Acad. Sci. USA, 96: 254-259 (1999).
Yao et al., "Microanalysis of Complex Tissue Lipids by High-Performance Thin-Layer Chromatography," Analytical Biochemistry, 150: 111-116 (1985).
Zielasek et al., "Functional Abnormalities in P0-Deficient Mice Resemble Human Hereditary Neuropathies Linked to P0 Gene Mutations," Muscle & Nerve, 19: 946-952 (1996).

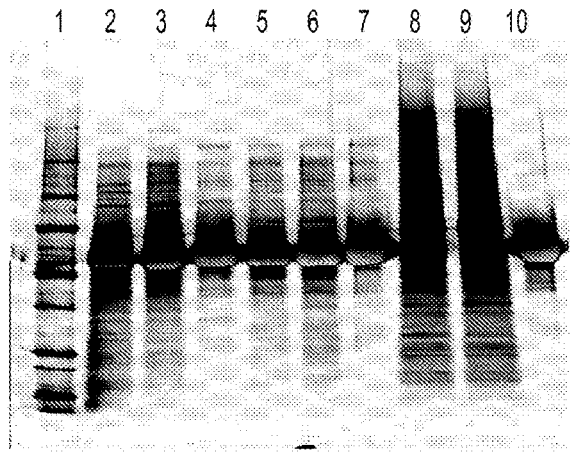

|     | Sample ID | %Purity by CE-SDS | HCP/ rhASA ratio |
| --- | --- | --- | --- |
| 0 | Q FF UPB | 27 | 1.1 |
| 00 | Fractogel UPB | 22 | 1.0 |
| 000 | Control UPB | 18 | 0.14 |
| 1 | Precision standard | N/A | |
| 2 | Q FF Q elution | 67 | 0.36 |
| 3 | Fractogel Q elution | 77 | 0.11 |
| 4 | Control Q elution | 86 | 0.012 |
| 5 | Q FF HA Elution | 76 | |
| 6 | Fractogel HA Elution | 85 | |
| 7 | Control HA elution | 100 | |
| 8 | Q FF HA Strip | 5 | |
| 9 | Fractogel HA Strip | 2 | |
| 10 | RHASA Standard | N/A | |

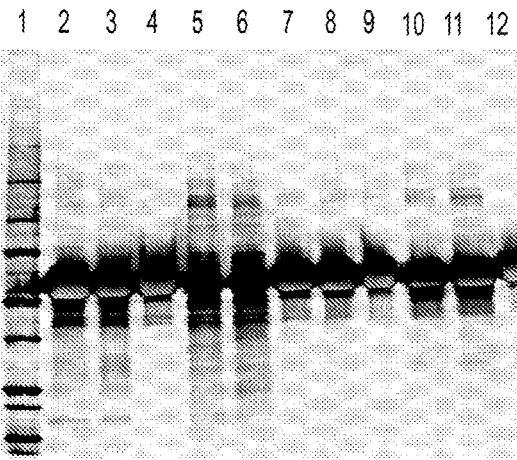

|     | Sample ID | %Purity by CE-SDS | HCP/ rhASA ratio |
| --- | --- | --- | --- |
| 1 | Precision Standard | N/A | |
| 2 | Q FF Phenyl elution | 100 | 0.07 |
| 3 | Fractogel Phenyl elution | 99 | 0.05 |
| 4 | Control Phenyl elution | 100 | 0.0029 |
| 5 | Q FF Phenyl strip | 54 | |
| 6 | Fractogel Phenyl strip | 46 | |
| 7 | Q FF SP Elution | 99 | 5.9E-04 |
| 8 | Fractogel SP Elution | 98 | 6.6E-04 |
| 9 | Control SP Elution | 100 | 1.8E-05 |
| 10 | Q FF SP strip | 98 | |
| 11 | Fractogel SP strip | 91 | |
| 12 | RHASA Standard | N/A | |

FIG. 4

| Lane | load sample | PAD ID | load vol. pl | total pg |
|---|---|---|---|---|
| 1 | Precision Plus Proteins Stds (Unstained) | | 10pl | |
| 2 | Assay Control #1 (0.5%) | | 20 | 50 ng each, 13-lac and Ref |
| 3 | Assay Control #2 (1%) | | 20 | 100 ng each, 13-lac and Ref |
| 4 | Reference Standard, 5.2 mg/mL | Lot# RS-JPT11-001 | 20 | 10 |
| 5 | RDAC11-172 B DS Feasibility 1 | 12AD0142 | 20 | 10 |
| 6 | RDAC11-172 E DS Feasibility 2 | 12AD0142 | 20 | 10 |
| 7 | RDAC11-172 B DS Control | 12AD0142 | 20 | 10 |
| 8 | Buffer Blank | | 20 | |
| 9 | Buffer Blank | | 20 | |
| 10 | Buffer Blank | | 20 | |

SEQUENCE LISTING

```
Sequence total quantity: 2
SEQ ID NO: 1            moltype = AA   length = 489
FEATURE                 Location/Qualifiers
source                  1..489
                        mol_type = protein
                        organism = Homo sapiens
SEQUENCE: 1
RPPNIVLIFA DDLGYGDLGC YGHPSSTTPN LDQLAAGGLR FTDFYVPVSL CTPSRAALLT   60
GRLPVRMGMY PGVLVPSSRG GLPLEEVTVA EVLAARGYLT GMAGKWHLGV GPEGAFLPPH   120
QGFHRFLGIP YSHDQGPCQN LTCFPPATPC DGGCDQGLVP IPLLANLSVE AQPPWLPGLE   180
ARYMAFAHDL MADAQRQDRP FFLYYASHHT HYPQFSGQSF AERSGRGPFG DSLMELDAAV   240
GTLMTAIGDL GLLEETLVIF TADNGPETMR MSRGGCSGLL RCGKGTTYEG GVREPALAFW   300
PGHIAPGVTH ELASSLDLLP TLAALAGAPL PNVTLDGFDL SPLLLGTGKS PRQSLFFYPS   360
YPDEVRGVFA VRTGKYKAHF FTQGSAHSDT TADPACHASS SLTAHEPPLL YDLSKDPGEN   420
YNLLGGVAGA TPEVLQALKQ LQLLKAQLDA AVTFGPSQVA RGEDPALQIC CHPGCTPRPA   480
CCHCPDPHA                                                           489

SEQ ID NO: 2            moltype = AA   length = 507
FEATURE                 Location/Qualifiers
source                  1..507
                        mol_type = protein
                        organism = Homo sapiens
SEQUENCE: 2
MGAPRSLLLA LAAGLAVARP PNIVLIFADD LGYGDLGCYG HPSSTTPNLD QLAAGGLRFT   60
DFYVPVSLCT PSRAALLTGR LPVRMGMYPG VLVPSSRGGL PLEEVTVAEV LAARGYLTGM   120
AGKWHLGVGP EGAFLPPHQG FHRFLGIPYS HDQGPCQNLT CFPPATPCDG GCDQGLVPIP   180
LLANLSVEAQ PPWLPGLEAR YMAFAHDLMA DAQRQDRPFF LYYASHHTHY PQFSGQSFAE   240
RSGRGPFGDS LMELDAAVGT LMTAIGDLGL LEETLVIFTA DNGPETMRMS RGGCSGLLRC   300
GKGTTYEGGV REPALAFWPG HIAPGVTHEL ASSLDLLPTL AALAGAPLPN VTLDGFDLSP   360
LLLGTGKSPR QSLFFYPSYP DEVRGVFAVR TGKYKAHFFT QGSAHSDTTA DPACHASSSL   420
TAHEPPLLYD LSKDPGENYN LLGGVAGATP EVLQALKQLQ LLKAQLDAAV TFGPSQVARG   480
EDPALQICCH PGCTPRPACC HCPDPHA                                       507
```

METHODS FOR PURIFICATION OF ARYLSULFATASE A

CROSS REFERENCE TO RELATED APPLICATIONS

This application claims benefit under 35 U.S.C. § 119(e) of U.S. Provisional Patent Application Ser. No. 61/750,693, filed Jan. 9, 2013, which application is hereby incorporated by reference in its entirety.

INCORPORATION BY REFERENCE OF SEQUENCE LISTING

The present specification makes reference to a Sequence Listing (submitted electronically as an XML file named SHR-1092US2). The XML file was generated on Jan. 25, 2023 and is 4 kilobytes in size. The entire contents of the sequence are herein incorporated by reference.

BACKGROUND

Metachromatic Leukodystrophy Disease (MLD), is an autosomal recessive disorder resulting from a deficiency of the enzyme Arylsulfatase A (ASA). ASA, which is encoded by the ARSA gene in humans, is an enzyme that breaks down cerebroside 3-sulfate or sphingolipid 3-O-sulfogalactosylceramide (sulfatide) into cerebroside and sulfate. In the absence of the enzyme, sulfatides accumulate in the nervous system (e.g., myelin sheaths, neurons and glial cells) and to a lesser extent in visceral organs. The consequence of these molecular and cellular events is progressive demyelination and axonal loss within the CNS and PNS, which is accompanied clinically by severe motor and cognitive dysfunction.

A defining clinical feature of this disorder is central nervous system (CNS) degeneration, which results in cognitive impairment (e.g., mental retardation, nervous disorders, and blindness, among others).

MLD can manifest itself in young children (Late-infantile form), where affected children typically begin showing symptoms just after the first year of life (e.g., at about 15-24 months), and generally do not survive past the age of 5 years. MLD can manifest itself in children (Juvenile form), where affected children typically show cognitive impairment by about the age of 3-10 years, and life-span can vary (e.g., in the range of 10-15 years after onset of symptoms). MLD can manifest itself in adults (Adult-onset form) and can appear in individuals of any age (e.g., typically at age 16 and later) and the progression of the disease can vary greatly.

Enzyme replacement therapy (ERT) is an approved therapy for treating MLD, which involves administering exogenous replacement ASA enzyme, particularly recombinant Arylsulfatase A (rASA) (e.g., recombinant human Arylsulfatase A (rhASA)) to patients with MLD.

SUMMARY

The present invention provides, among other things, improved methods for purifying ASA protein produced recombinantly for enzyme replacement therapy. The present invention is, in part, based on the surprising discovery that recombinant ASA protein can be purified from unprocessed biological materials, such as, ASA-containing cell culture medium, using a process involving only a single step of post-chromatographic ultrafiltration/diafiltration, resulting in pharmaceutically acceptable drug substance directly into a final formulation buffer. As described in the Examples below, this single step UF/DF process is achieved by simply pooling eluate from the chromatography steps and adjusting the pH of the pooled eluate to about 6.0. Prior to the present invention, processes for purifying recombinantly produced rASA protein involved at least two steps of postchromatographic ultrafiltration/diafiltration (UF/DF). As described in the Examples section, recombinant ASA protein purified using a one-step UF/DF process according to the invention has comparable purity, activity and yield as compared to the recombinant ASA proteins purified using multiple UF/DF steps. For example, the recombinant ASA enzyme purified according to the present invention has no more than 100 pg/mg Host Cell DNA, retains high specific activity (e.g., about 50-140 U/mg) and other distinct characteristics that may facilitate bioavailability and/or lysosomal targeting of the recombinant ASA protein. Therefore, this simplified process is faster, cheaper and equally effective in purifying recombinant ASA protein. This process is particularly useful when combined with high loading capacity chromatography steps to facilitate large scale production of recombinant ASA protein.

Thus, in one aspect, the present invention provides a method of purifying recombinant arylsulfatase A (ASA) protein including steps of purifying recombinant arylsulfatase A (ASA) protein from an impure preparation by conducting one or more chromatography steps; pooling eluate from the one or more chromatography steps; adjusting the pH of the pooled elute to pH of or greater than about 5.8, 5.9, or 6.0; and subjecting the pH-adjusted eluate to ultrafiltration and/or diafiltration. In some embodiments, the pH is adjusted to about 5.8-7.0 (e.g., about 5.8-6.8, about 5.8-6.6, about 5.8-6.4, about 5.8-6.2, about 5.8-6.1, about 5.8-6.0, about 5.9-7.0, about 5.9-6.8, about 5.9-6.6, about 5.9-6.4, about 5.9-6.2, about 5.9-6.1, about 5.9-6.0, about 5.95-6.20, about 5.95-6.15, about 5.95-6.10, or about 5.95-6.05). In some embodiments, the pH is adjusted to about 6.0.

In some embodiments, the pH is adjusted using a buffer comprising sodium phosphate, sodium chloride and sodium citrate with pH 7.0. In some embodiments, the buffer comprises about 0.1-0.5 M (e.g., about 0.1-0.4 M, 0.1-0.3 M, 0.2-0.4 M, or 0.2-0.3 M) sodium phosphate, about 0.5-2.5 M (e.g., about 0.5-2.0 M, 0.5-1.5 M, 0.75-2.5 M, 0.75-2.0 M, 0.75-1.5 M, 1.0-2.5 M, 1.0-2.0 M, or 1.0-1.5 M) sodium chloride and about 0.1-0.6 M (e.g., about 0.1-0.5 M, 0.1-0.4 M, 0.2-0.5 M, 0.2-0.4 M, 0.3-0.5 M, or 0.3-0.4 M) sodium citrate with pH of about 7.0, 7.1, 7.2, 7.3, 7.4 or 7.5. In some embodiments, the buffer comprises about 0.25 M sodium phosphate, about 1.33 M sodium chloride and about 0.34 M sodium citrate with pH of about 7.0.

In some embodiments, a viral filtration is performed before the step of ultrafiltration and diafiltration. In some embodiments, a single step of ultrafiltration and/or diafiltration is performed. In some embodiments, the single step of ultrafiltration and/or diafiltration comprises only one diafiltration. In various embodiments, the ultrafiltration is tangential flow ultrafiltration.

In some embodiments, the one or more chromatography steps comprise a cation-exchange chromatography. In some embodiments, the cation-exchange chromatography is the last chromatography step and the eluate from the cation-exchange chromatography is pooled before adjusting the pH. In some embodiments, one or more of anion-exchange chromatography, mixed-mode chromatography, and hydrophobic interaction chromatography are conducted prior to conducting the cation-exchange chromatography.

In some embodiments, the one or more chromatography steps comprise an affinity chromatography. In some embodiments, the affinity chromatography is the first chromatography step. In some embodiments, the affinity chromatography is the last chromatography step and the eluate from the affinity chromatography is pooled before adjusting the pH. In some embodiments, one or more of anion-exchange chromatography, mixed-mode chromatography, and hydrophobic interaction chromatography are conducted before conducting the affinity chromatography. In some embodiments, one or more of anion-exchange chromatography, mixed-mode chromatography, and hydrophobic interaction chromatography are conducted after conducting the affinity chromatography.

In some embodiments, the anion-exchange chromatography is Q chromatography. In some embodiments, the anion-exchange chromatography comprises a TMAE resin (e.g., FRACTOGEL® TMAE). In some embodiments, the TMAE resin, once loaded with the impure preparation, is washed with a first wash buffer comprising MES-Tris with pH about 7.0. In certain embodiments, the first wash buffer comprises about 20-75 mM MES-Tris (e.g., about 30-60 mM, 40-70 mM, or 40-60 mM). In certain embodiments, the first wash buffer comprises about 20 mM, 25 mM, 30 mM, 35 mM, 40 mM, 45 mM, 50 mM, 55 mM, 60 mM, 65 mM, 70 mM, or 75 mM MES-Tris.

In some embodiments, the TMAE resin is washed with a second wash buffer comprising MES-Tris and NaCl with pH about 7.0. In some embodiments, the second wash buffer comprises about 5-75 mM MES-Tris (e.g., about 5-70 mM, 5-60 mM, 5-50 mM, 5-40 mM, 5-30 mM, 10-60 mM, 10-50 mM, 10-40 mM, 10-30 mM, or 15-25 mM) and about 50-150 mM NaCl (e.g., about 50-140 mM, 50-130 mM, 50-120 mM, 50-110 mM, 75-150 mM, 75-140 mM, 75-130 mM, 75-120 mM, or 75-110 mM) with pH of about 7.0. In some embodiments, the second wash buffer comprises about 5 mM, 10 mM, 20 mM, 30 mM, 40 mM, 50 mM, 60 mM, or 75 mM MES-Tris and about 50 mM, 60 mM, 70 mM, 80 mM, 90 mM, 100 mM, 110 mM, 120 mM, 130 mM, 140 mM or 150 mM NaCl with pH of about 7.0. In some embodiments, the second wash buffer comprises about 20 mM MES-Tris and about 100 mM NaCl with pH of about 7.0.

In some embodiments, the TMAE resin, once loaded with the impure preparation, is eluted using an elution buffer comprising MES-Tris and NaCl with pH of about 7.0. In some embodiments, the elution buffer comprises about 5-75 mM MES-Tris (e.g., about 5-70 mM, 5-60 mM, 5-50 mM, 5-40 mM, about 5-30 mM, 10-75 mM, 10-60 mM, 10-50 mM, 10-40 mM, or 10-30 mM) and about 150-300 mM NaCl (e.g., about 150-250 mM, about 180-260 mM, about 200-280 mM, 200-260 mM, 200-240 mM, 210-300 mM, 210-280 mM, 210-260 mM, or 210-240 mM) with pH of about 7.0. In some embodiments, the elution buffer comprises about 10 mM, 20 mM, 30 mM, 40 mM, 50 mM, 60 mM, 70 mM, or 75 mM MES-Tris and about 150 mM, 180 mM, 200 mM, 210 mM, 220 mM, 230 mM, 240 mM, 250 mM, 260 mM, 270 mM, 280 mM, 290 mM, or 300 mM NaCl with pH of about 7.0. In some embodiments, the elution buffer comprises about 20 mM MES-Tris and about 220 mM NaCl with pH of about 7.0.

In some embodiments, the anion-exchange chromatography utilizes a column selected from the group consisting of Q SEPHAROSE™ Fast Flow, Q SEPHAROSE™ High Performance, Q SEPHAROSE™ XL, CAPTO™ Q, DEAE, TOYOPEARL GIGACAP® Q, FRACTOGEL® TMAE, ESHMUNO™ Q, NUVIA™ Q, or UNOSPHERE™ Q.

In some embodiments, a suitable mixed-mode chromatography for the present invention is hydroxyapatite (HA) chromatography.

In some embodiments, a suitable hydrophobic interaction chromatography for the present invention is phenyl chromatography.

In some embodiments, anion-exchange chromatography (e.g., with TMAE resin), mixed-mode chromatography (e.g., HA chromatography), hydrophobic interaction chromatography (e.g., phenyl chromatography) and cation-exchange chromatography (e.g., SP chromatography), are conducted in that order.

In some embodiments, a suitable affinity chromatography for the present invention utilizes an anti-Arylsulfatase A antibody (e.g., an anti-human Arylsulfatase A antibody).

In some embodiments, suitable anion-exchange chromatography uses a column with a loading capacity greater than about 4.5 g/L (e.g., greater than about 5 g/L, 6 g/L, 7 g/L, 8 g/L, 9 g/L, 10 g/L, 11 g/L, 12 g/L, 13 g/L, 14 g/L, or 15 g/L). In some embodiments, suitable anion-exchange chromatography uses a column with a loading capacity ranging between about 4.5-20 g/L (e.g., ranging between about 5-20 g/L; 5-19 g/L, 5-18 g/L, 5-17 g/L, 5-16 g/L, 5-15 g/L, 7.5-20 g/L, 7.5-19 g/L, 7.5-18 g/L, 7.5-17 g/L, 7.5-16 g/L, 7.5-15 g/L, 10-20 g/L, 10-19 g/L, 10-18 g/L, 10-17 g/L, 10-16 g/L, or 10-15 g/L). In particular embodiments, a suitable loading capacity of the column is about 10-15 g/L.

In some embodiments, ultrafiltration of the impure preparation is conducted prior to the one or more chromatography steps. In some embodiments, an ultrafiltration step suitable for the present invention is tangential flow ultrafiltration. In certain embodiments, suitable ultrafiltration uses a membrane filter comprising a pore size with a molecular weight cutoff of at least about 10 kDA, at least about 20 kDA, at least about 30 kDA, at least about 40 kDA, at least about 50 kDA. In certain embodiments, at least 75% of the recombinant ASA is retained in the impure preparation. In certain embodiments, at least 75% of the recombinant ASA permeates the filter. In certain embodiments, a suitable ultrafiltration step utilizes a polyethersulfone or cellulose membrane.

In some embodiments, clarification of the impure preparation is conducted prior to ultrafiltration of the impure preparation. In some embodiments, a clarification step suitable for the present invention is conducting filtration with one or more depth filters. In some certain embodiments, filtration of the impure preparation is conducted using a series of depth filters. In some certain embodiments, a suitable series of depth filters utilizes a membrane comprising cellulose, diatomaceous earth, polyethersulfone, or a combination thereof.

In some embodiments, the ultrafiltration is followed by one or more steps of depth filtration and/or viral inactivation. In some embodiments, the one or more steps of depth filtration and/or viral inactivation is followed by the one or more chromatography steps. In some embodiments, the step of viral inactivation comprises adding a detergent to the impure preparation.

In some embodiments, a method according to the present invention can be used to purify a recombinant ASA protein produced by mammalian cells cultured in suspension. In some embodiments, the mammalian cells are cultured in a bioreactor. In some embodiments, the media is serum-based. In some embodiments, the media is serum-free. In some embodiments, the serum-free medium is a chemically-defined medium.

In some embodiments, the impure preparation is a feed stream from a perfusion bioreactor. In some embodiments, the impure preparation is prepared from the medium (e.g., serum-based or serum-free) containing recombinant ASA protein secreted from the mammalian cells. In some embodiments, the impure preparation is thawed from a frozen medium preparation.

In some embodiments, the step of ultrafiltration and/or diafiltration comprises exchanging the purified recombinant ASA protein into a drug formulation buffer.

In some embodiments, the recombinant ASA protein has an amino acid sequence at least about 50%, 55%, 60%, 65%, 70%, 75%, 80%, 85%, 90%, 95%, 96%, 97%, 98%, or 99% identical to SEQ ID NO:1. In some embodiments, the recombinant ASA protein has an amino acid sequence identical to SEQ ID NO:1.

In some embodiments, the purified recombinant ASA protein according to the present invention contains less than about 150 ng/mg, 140 ng/mg, 130 ng/mg, 120 ng/mg, 110 ng/mg, 100 ng/mg, 90 ng/mg, 80 ng/mg, 70 ng/mg, 60 ng/mg, 50 ng/mg, 40 ng/mg, 30 ng/mg, 20 ng/mg, or 10 ng/mg Host Cell Protein (HCP).

In some embodiments, the purified recombinant ASA protein, when subject to SDS-PAGE with Coomassie Blue staining, has no new bands with intensity greater than a 1.0% assay control.

In some embodiments, the purified recombinant ASA protein contains less than about 150 pg/mg, 140 pg/mg, 130 pg/mg, 120 pg/mg, 110 pg/mg, 100 pg/mg, 90 pg/mg, 80 pg/mg, 70 pg/mg, 60 pg/mg, 50 pg/mg, 40 pg/mg, 30 pg/mg, 20 pg/mg, or 10 pg/mg Host Cell DNA.

In some embodiments, the present invention provides a method of purifying recombinant arylsulfatase A (ASA) protein comprising steps of purifying recombinant arylsulfatase A (ASA) protein from an impure preparation by conducting one or more chromatography steps, wherein the first chromatography step uses a column with a loading capacity of or greater than about 4.5 g protein/L resin (e.g., greater than about 5 g/L, 6 g/L, 7 g/L, 8 g/L, 9 g/L, 10 g/L, 11 g/L, 12 g/L, 13 g/L, 14 g/L, 15 g/L, 16 g/L, 17 g/L, 18 g/L, 19 g/L or 20 g/L); pooling eluate from the one or more chromatography steps; adjusting the pH of the pooled elute to pH of or greater than about 6.0; and subjecting the pH-adjusted eluate to ultrafiltration and/or diafiltration.

In some embodiments, the step of conducting one or more chromatography steps comprises conducting a first ion-exchange chromatography, mixed-mode chromatography, hydrophobic interaction chromatography and a second ion-exchange chromatography, in that order.

In some embodiments, the one or more chromatography steps includes an affinity chromatography. In some certain embodiments, the affinity chromatography is conducted prior to the first ion-exchange chromatography step. In some certain embodiments, the affinity chromatography is conducted after conducting the second ion-exchange chromatography step. In some embodiments, the affinity chromatography is conducted between the first ion-exchange chromatography step and the second ion-exchange chromatography step.

In some embodiments, the step of conducting one or more chromatography steps comprises conducting anion-exchange chromatography, mixed-mode chromatography, hydrophobic interaction chromatography and cation-exchange chromatography, in that order.

In some embodiments, the step of conducting one or more chromatography steps comprises conducting affinity chromatography anion-exchange chromatography, mixed-mode chromatography, hydrophobic interaction chromatography and cation-exchange chromatography, in that order.

In some embodiments, the step of conducting one or more chromatography steps comprises conducting anion-exchange chromatography, mixed-mode chromatography, hydrophobic interaction chromatography, cation-exchange chromatography and affinity chromatography, in that order.

In some embodiments, the anion-exchange chromatography uses a column with TMAE resin. In certain embodiments, the TMAE column has a loading capacity of about 5-20 g protein/L resin (e.g., about 5-19 g/L, 5-18 g/L, 5-17 g/L, 5-16 g/L, 5-15 g/L, 7.5-20 g/L, 7.5-19 g/L, 7.5-18 g/L, 7.5-17 g/L, 7.5-16 g/L, 7.5-15 g/L, 10-20 g/L, 10-19 g/L, 10-18 g/L, 10-17 g/L, 10-16 g/L, or 10-15 g/L).

In some embodiments, a single step of ultrafiltration and/or diafiltration is performed after the one or more chromatography steps.

Among other things, the present invention provides a recombinant arylsulfatase A (ASA) protein purified according to an inventive method described herein and a pharmaceutical composition containing the same.

In some embodiments, the present invention provides a composition comprising purified recombinant arylsulfatase A (ASA) having an amino acid sequence at least about 50%, 55%, 60%, 65%, 70%, 75%, 80%, 85%, 90%, 95%, 96%, 97%, 98%, or 99% identical to SEQ ID NO:1, wherein the purified recombinant ASA a specific activity of at least about 50 U/mg and further wherein the purified recombinant ASA contains less than 150 ng/mg Host Cell Protein (HCP) and/or 150 pg/mg Host Cell DNA (HCD). In some embodiments, the purified recombinant ASA has an amino acid sequence identical to SEQ ID NO:1. In some embodiments, the purified recombinant ASA contains less than about 140 ng/mg, 130 ng/mg, 120 ng/mg, 110 ng/mg, 100 ng/mg, 90 ng/mg, 80 ng/mg, 70 ng/mg, 60 ng/mg, 50 ng/mg, 40 ng/mg, 30 ng/mg, 20 ng/mg, or 10 ng/mg Host Cell Protein (HCP). In some embodiments, the purified recombinant ASA contains less than about 140 pg/mg, 130 pg/mg, 120 pg/mg, 110 pg/mg, 100 pg/mg, 90 pg/mg, 80 pg/mg, 70 pg/mg, 60 pg/mg, 50 pg/mg, 40 pg/mg, 30 pg/mg, 20 pg/mg, or 10 pg/mg Host Cell DNA.

In some embodiments, the purified recombinant ASA has a specific activity of at least about 50 U/mg, 60 U/mg, 70 U/mg, 80 U/mg, 90 U/mg, 100 U/mg, 110 U/mg, 120 U/mg, 130 U/mg, 140 U/mg. In some embodiments, the purified recombinant ASA has a specific activity ranging from about 50-200 U/mg (e.g., about 50-190 U/mg, 50-180 U/mg, 50-170 U/mg, 50-160 U/mg, 50-150 U/mg, 50-140 U/mg, 50-130 U/mg, 50-120 U/mg, 50-110 U/mg, 50-100 U/mg, 60-140 U/mg, 60-130 U/mg, 60-120 U/mg, 60-110 U/mg, 60-100 U/mg, 70-140 U/mg, 70-130 U/mg, 70-120 U/mg, 70-110 U/mg, 70-100 U/mg, 80-140 U/mg, 80-130 U/mg, 80-120 U/mg, 80-110 U/mg, 80-100 U/mg, 90-140 U/mg, 90-130 U/mg, 90-120 U/mg, 90-110 U/mg, 90-100 U/mg, 100-140 U/mg, 100-130 U/mg, 100-120 U/mg, 100-110 U/mg, 110-140 U/mg, 110-130 U/mg, 110-120 U/mg, 120-140 U/mg, 120-130 U/mg, or 130-140 U/mg).

In some embodiments, the present invention provides a composition comprising purified recombinant arylsulfatase A (ASA) having an amino acid sequence at least about 50%, 55%, 60%, 65%, 70%, 75%, 80%, 85%, 90%, 95%, 96%, 97%, 98%, or 99% identical to SEQ ID NO:1, wherein the purified ASA is characterized with a glycan map comprising one or more peak groups selected from the peak groups indicative of neutral (peak group 1), mono-sialylated (peak group 2), capped mannose-6-phosphated (peak group 3), di-sialylated (peak group 4), mono-mannose-6-phosphated (peak group 5), hybrid (peak group 6), and di-mannose-6-phosphated (peak group 7). In some embodiments, the purified ASA is characterized with a glycan map comprising at least two or more, three or more, four or more, five or more, six or more or seven or more of the peak groups 1-7. In some embodiments, the purified recombinant ASA has an amino acid sequence identical to SEQ ID NO:1.

In some embodiments, the present invention provides a formulation comprising the composition described herein and a physiologically acceptable carrier. In some embodiments, the formulation is suitable for intravenous administration. In some embodiments, the formulation is suitable for intrathecal administration. In some embodiments, the formulation is suitable for subcutaneous administration.

Among other things, the present invention provides methods of treating Metachromatic Leukodystrophy Disease comprising administering into a subject in need of treatment a purified recombinant ASA protein, a pharmaceutical composition or formulation described herein.

As used herein, the terms "ASA protein," "ASA," "ASA enzyme," or grammatical equivalents, refer to a preparation of recombinant ASA protein molecules unless otherwise specifically indicated.

As used in this application, the terms "about" and "approximately" are used as equivalents. Any numerals used in this application with or without about/approximately are meant to cover any normal fluctuations appreciated by one of ordinary skill in the relevant art.

Other features, objects, and advantages of the present invention are apparent in the detailed description that follows. It should be understood, however, that the detailed description, while indicating embodiments of the present invention, is given by way of illustration only, not limitation. Various changes and modifications within the scope of the invention will become apparent to those skilled in the art from the detailed description.

BRIEF DESCRIPTION OF THE DRAWING

The Figures described below, that together make up the Drawing, are for illustration purposes only, not for limitation.

FIG. 4 depicts exemplary SDS-PAGE (silver) gels showing similar band profiles for both Fractogel and Q FF through the entire process.

DEFINITIONS

Figure 1:
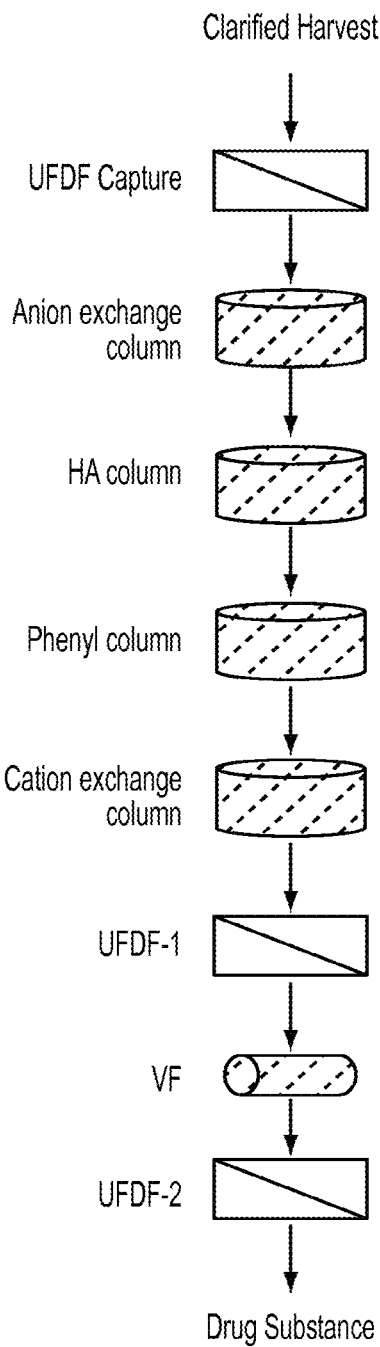
FIG. 1 illustrates a generalized flow diagram of an exemplary purification process.

In order for the present invention to be more readily understood, certain terms are first defined below. Additional definitions for the following terms and other terms are set forth throughout the specification.

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Biologically active: As used herein, the phrase "biologically active" refers to a characteristic of any agent that has activity in a biological system, and particularly in an organism. For instance, an agent that, when administered to an organism, has a biological effect on that organism, is considered to be biologically active. In particular embodiments, where a protein or polypeptide is biologically active, a portion of that protein or polypeptide that shares at least one biological activity of the protein or polypeptide is typically referred to as a "biologically active" portion.

Cation-independent mannose-6-phosphate receptor (CI-MPR): As used herein, the term "cation-independent mannose-6-phosphate receptor (CI-MPR)" refers to a cellular receptor that binds mannose-6-phosphate (M6P) tags on acid hydrolase precursors in the Golgi apparatus that are destined for transport to the lysosome. In addition to mannose-6-phosphates, the CI-MPR also binds other proteins including IGF-II. The CI-MPR is also known as "M6P/IGF-II receptor," "CI-MPR/IGF-II receptor," "IGF-II receptor" or "IGF2 Receptor." These terms and abbreviations thereof are used interchangeably herein.

Chromatography: As used herein, the term "chromatography" refers to a technique for separation of mixtures. Typically, the mixture is dissolved in a fluid called the "mobile phase," which carries it through a structure holding another material called the "stationary phase." Column chromatography is a separation technique in which the stationary bed is within a tube, i.e., column.

Diluent: As used herein, the term "diluent" refers to a pharmaceutically acceptable (e.g., safe and non-toxic for administration to a human) diluting substance useful for the preparation of a reconstituted formulation. Exemplary diluents include sterile water, bacteriostatic water for injection (BWFI), a pH buffered solution (e.g. phosphate-buffered saline), sterile saline solution, Ringer's solution or dextrose solution.

Elution: As used herein, the term "elution" refers to the process of extracting one material from another by washing with a solvent. For example, in ion-exchange chromatography, elution is a process to wash loaded resins to remove captured ions.

Eluate: As used herein, the term "eluate" refers to a combination of mobile phase "carrier" and the analyte material that emerge from the chromatography, typically as a result of eluting.

Enzyme replacement therapy (ERT): As used herein, the term "enzyme replacement therapy (ERT)" refers to any therapeutic strategy that corrects an enzyme deficiency by providing the missing enzyme. Once administered, enzyme is taken up by cells and transported to the lysosome, where the enzyme acts to eliminate material that has accumulated in the lysosomes due to the enzyme deficiency. Typically, for lysosomal enzyme replacement therapy to be effective, the therapeutic enzyme is delivered to lysosomes in the appropriate cells in target tissues where the storage defect is manifest. The purification processes described herein may be used to purify and formulate recombinant Arylsulfatase A as a drug substance for ERT of MLD.

Equilibrate or Equilibration: As used herein, the terms "equilibrate" or "equilibration" in relation to chromatography refer to the process of bringing a first liquid (e.g., buffer) into balance with another, generally to achieve a stable and equal distribution of components of the liquid (e.g., buffer). For example, in some embodiments, a chromatographic column may be equilibrated by passing one or more column volumes of a desired liquid (e.g., buffer) through the column.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control individual (or multiple control individuals) in the absence of the treatment described herein. A "control individual" is an individual afflicted with the same form of lysosomal storage disease as the individual being treated, who is about the same age as the individual being treated (to ensure that the stages of the disease in the treated individual and the control individual(s) are comparable).

Impurities: As used herein, the term "impurities" refers to substances inside a confined amount of liquid, gas, or solid, which differ from the chemical composition of the target material or compound. Impurities are also referred to as contaminants.

Load: As used herein, the term "load" refers to, in chromatography, adding a sample-containing liquid or solid to a column. In some embodiments, particular components of the sample loaded onto the column are then captured as the loaded sample passes through the column. In some embodiments, particular components of the sample loaded onto the column are not captured by, or "flow through", the column as the loaded sample passes through the column.

Polypeptide: As used herein, a "polypeptide", generally speaking, is a string of at least two amino acids attached to one another by a peptide bond. In some embodiments, a polypeptide may include at least 3-5 amino acids, each of which is attached to others by way of at least one peptide bond. Those of ordinary skill in the art will appreciate that polypeptides sometimes include "non-natural" amino acids or other entities that nonetheless are capable of integrating into a polypeptide chain, optionally.

Pool: As used herein, the term "pool" in relation to chromatography refers to combining one or more fractions of fluid that has passed through a column together. For example, in some embodiments, one or more fractions which contain a desired component of a sample that has been separated by chromatography (e.g., "peak fractions") can be "pooled" together generate a single "pooled" fraction.

Replacement enzyme: As used herein, the term "replacement enzyme" refers to any enzyme that can act to replace at least in part the deficient or missing enzyme in a disease to be treated. In some embodiments, the term "replacement enzyme" refers to any enzyme that can act to replace at least in part the deficient or missing lysosomal enzyme in a lysosomal storage disease to be treated. In some embodiments, a replacement enzyme (e.g., rASA) is capable of reducing accumulated materials in mammalian lysosomes or that can rescue or ameliorate one or more lysosomal storage disease (e.g., MLD) symptoms. Replacement enzymes suitable for the invention include both wild-type or modified lysosomal enzymes and can be produced using recombinant and synthetic methods or purified from nature sources. A replacement enzyme can be a recombinant, synthetic, gene-activated or natural enzyme.

Soluble: As used herein, the term "soluble" refers to the ability of a therapeutic agent to form a homogenous solution. In some embodiments, the solubility of the therapeutic agent in the solution into which it is administered and by which it is transported to the target site of action is sufficient to permit the delivery of a therapeutically effective amount of the therapeutic agent to the targeted site of action. Several factors can impact the solubility of the therapeutic agents. For example, relevant factors which may impact protein solubility include ionic strength, amino acid sequence and the presence of other co-solubilizing agents or salts (e.g., calcium salts). In some embodiments, therapeutic agents in accordance with the present invention are soluble in its corresponding pharmaceutical composition.

Stability: As used herein, the term "stable" refers to the ability of the therapeutic agent (e.g., a recombinant enzyme) to maintain its therapeutic efficacy (e.g., all or the majority of its intended biological activity and/or physiochemical integrity) over extended periods of time. The stability of a therapeutic agent, and the capability of the pharmaceutical composition to maintain stability of such therapeutic agent, may be assessed over extended periods of time (e.g., for at least 1, 3, 6, 12, 18, 24, 30, 36 months or more). In the context of a formulation a stable formulation is one in which the therapeutic agent therein essentially retains its physical and/or chemical integrity and biological activity upon storage and during processes (such as freeze/thaw, mechanical mixing and lyophilization). For protein stability, it can be measure by formation of high molecular weight (HMW) aggregates, loss of enzyme activity, generation of peptide fragments and shift of charge profiles.

Viral Processing: As used herein, the term "viral processing" refers to "viral removal," in which viruses are simply removed from the sample (e.g. viral filtration), or "viral inactivation," in which the viruses remain in a sample but in a non-infective form. In some embodiments, viral removal may utilize nanofiltration and/or chromatographic techniques, among others. In some embodiments, viral inactivation may utilize solvent inactivation, detergent inactivation, pasteurization, acidic pH inactivation, and/or ultraviolet inactivation, among others.

DETAILED DESCRIPTION

The present invention provides, among other things, improved methods for purifying ASA protein produced recombinantly for enzyme replacement therapy. In some embodiments, the present invention provides a method of purifying a recombinant ASA protein from an impure preparation (e.g., unprocessed biological materials, such as, ASA-containing cell culture medium) using a process involving only a single step of post-chromatographic ultrafiltration/diafiltration. In some embodiments, this single step UF/DF process is achieved by pooling eluate from the chromatography steps and adjusting the pH of the pooled eluate to or greater than about 6.0. In some embodiments, this simplified process is combined with high loading capacity chromatography steps to facilitate large scale production of recombinant ASA protein.

Various aspects of the invention are described in further detail in the following subsections. The use of subsections is not meant to limit the invention. Each subsection may apply to any aspect of the invention. In this application, the use of "or" means "and/or" unless stated otherwise.

Arylsulfatase A

Arylsulfatase A (ASA, ARSA, or cerebroside-sulfatase) is an enzyme that breaks down cerebroside 3-sulfate (or sulfatide) into cerebroside and sulfate. Specifically, galactosyl sulfatide is normally metabolized by the hydrolysis of 3-O-sulphate linkage to form galactocerebroside through the combined action of the lysosomal enzyme Arylsulfatase A (EC 3.1.6.8) (Austin et al. *Biochem J.* 1964, 93, 15C-17C) and a sphingolipid activator protein called saposin B. A deficiency of Arylsulfatase A occurs in all tissues from patients with the late infantile, juvenile, and adult forms of Metachromatic Leukodystrophy (MLD). As used herein, the Arylsulfatase A protein will be termed "ASA" or "ARSA" and the saposin B will be termed "Sap-B".

Arylsulfatase A is an acidic glycoprotein with a low isoelectric point. Above pH 6.5, the enzyme exists as a monomer with a molecular weight of approximately 100 kDa. ASA exists as a 480 kDa octamer in acidic conditions (pH≤about 5.0), but dissociates into dimers at neutral pH levels. In human urine, the enzyme consists of two non-identical subunits of 63 and 54 kDa (Laidler P M et al. *Biochim Biophys Acta.* 1985, 827, 73-83). Arylsulfatase A purified from human liver, placenta, and fibroblasts also consist of two subunits of slightly different sizes varying between 55 and 64 kDa (Draper R K et al. *Arch Biochemica Biophys.* 1976, 177, 525-538, Waheed A et al. *Hoppe Seylers Z Physiol Chem.* 1982, 363, 425-430, Fujii T et al. *Biochim Biophys Acta.* 1992, 15 1122, 93-98). As in the case of other lysosomal enzymes, arylsulfatase A is synthesized on membrane-bound ribosomes as a glycosylated precursor. It then passes through the endoplasmic reticulum and Golgi, where its N-linked oligosaccharides are processed with the formation of phosphorylated and sulfated oligosaccharide of the complex type (Waheed A et al. *Biochim Biophys Acta.* 1985, 847, 53-61, Braulke T et al. *Biochem Biophys Res Commun.* 1987, 143, 178-185). In normal cultured fibroblasts, a precursor polypeptide of 62 kDa is produced, which translocates via mannose-6-phosphate receptor binding (Braulke T et al. *J Biol Chem.* 1990, 265, 6650-6655) to an acidic prelysosomal endosome (Kelly B M et al. *Eur J Cell Biol.* 1989, 48, 71-78).

The methods described herein can be used to purify arylsulfatase A from any source, e.g., from tissues, or cultured cells (e.g., human cells (e.g., fibroblasts) that recombinantly produce arylsulfatase A). Arylsulfatase A of any origin, including, but not limited to human and other animals, such as mammals, can be produced by the methods described herein.

The length (18 amino acids) of the human Arylsulfatase A signal peptide is based on the consensus sequence and a specific processing site for a signal sequence. Hence, from the deduced human ASA cDNA (EMBL GenBank accession numbers J04593 and X521151) the cleavage of the signal peptide occurs in all cells after residue number 18 (Ala), resulting in the mature form of the human arylsulfatase A. As used herein, recombinant arylsulfatase A will be abbreviated "rASA". The mature form of arylsulfatase A including the mature form of human arylsulfatase A will be termed "mASA" and the mature recombinant human ASA will be termed "mrhASA".

Multiple forms of arylsulfatase A have been demonstrated on electrophoresis and isoelectric focusing of enzyme preparations from human urine (Luijten J A F M et al. *J Mol Med.* 1978, 3, 213), leukocytes (Dubois et al. Biomedicine. 1975, 23, 116-119, Manowitz P et al. *Biochem Med Metab Biol.* 1988, 39, 117-120), platelets (Poretz et al. *Biochem J.* 1992, 287, 979-983), cultured fibroblasts (Waheed A et al. *Hoppe Seylers Z Physiol Chem.* 1982, 363, 425-430, Stevens R L et al. *Biochim Biophys Acta.* 1976, 445, 661-671, Farrell D F et al. *Neurology.* 1979, 29, 16-20) and liver (Stevens R L et al. *Biochim Biophys Acta.* 1976, 445, 661-671, Farrell D F et al. *Neurology.* 1979, 29, 16-20, Sarafian T A et al. *Biochem Med.* 1985, 33, 372-380). Treatment with endo-glycosidase H, sialidase, and alkaline phosphatase reduces the molecular size and complexity of the electrophoretic pattern, which suggests that much of the charge heterogeneity of arylsulfatase A is due to variations in the carbohydrate content of the enzyme.

The active site of arylsulfatase A contains an essential histidine residue (Lee G D and Van Etten R L, *Arch Biochem Biophys.* 1975, 171, 424-434) and two or more arginine residues (James G T, *Arch Biochem Biophys.* 1979, 97, 57-62). Many anions are inhibitors of the enzyme at concentrations in the millimolar range or lower.

The human arylsulfatase A gene structure has been described. As used herein, this gene will be termed "ARSA." However, "ARSA" may also refer to arylsulfatase A protein in some cases. The ARSA gene is located near the end of the long arm of chromosome 22 (22q13.31-qter), it spans 3.2 kb (Kreysing et al. *Eur J Biochem.* 1990, 191, 627-631) and consists of eight exons specifying the 507 amino acid enzyme unit (Stein et al. *J Biol Chem.* 1989, 264, 1252-1259). Messenger RNAs of 2.1, 3.7, and 4.8 kb have been detected in fibroblast cells, with the 2.1-kb message apparently responsible for the bulk of the active arylsulfatase A generated by the cell (Kreysing et al. *Eur J Biochem.* 1990, 191, 627-631). The ARSA sequence has been deposited at the EMBL GenBank with the accession number X521150. Differences between the published cDNA and the coding part of the ARSA were described by Kreysing et al. (*Eur J Biochem.* 1990, 191, 627-631). The cDNA sequence originally described by Stein et al. (*J Biol Chem.* 1989, 264, 1252-1259) and the cDNA sequence described by Kreysing et al. (*Eur J Biochem.* 1990, 191, 627-631) have been deposited at the EMBL GenBank with the following accession numbers J04593 and X521151, respectively.

Several polymorphisms and more than 40 disease-related mutations have been identified in the ARSA gene (Gieselmann et al. *Hum Mutat.* 1994, 4, 233-242, Barth et al. *Hum Mutat.* 1995, 6, 170-176, Draghia et al. *Hum Mutat.* 1997, 9, 234-242). The disease-related mutations in the ARSA gene can be categorized in two broad groups that correlate fairly well with the clinical phenotype of MLD. One group (I) produces no active enzyme, no immunoreactive protein, and expresses no ASA activity when introduced into cultured animal cell lines. The other group (A) generates small amounts of cross-reactive material and low levels of functional enzyme in cultured cells. Individuals homozygous for a group (I) mutation, or having two different mutations from this group, express late infantile MLD. Most individuals with one group (I)-type and one group (A)-type mutation develop the juvenile-onset form, whereas those with two group (A)-type mutations generally manifest adult MLD. Some of the mutations have been found relatively frequently, whereas others have been detected only in single families. It is possible to trace specific mutations through members of many families, however general carrier screening is not yet feasible.

In addition to the disease-related mutations described above, several polymorphisms have been identified in the ARSA gene. Extremely low ASA activity has been found in some clinically normal parents of MLD patients and also in the general population. This so-called pseudodeficiency ASA has been associated with a common polymorphism of the ARSA gene (Gieselmann et al. *Dev Neurosci.* 1991, 13, 222-227).

Recombinant ASA Protein

As used herein, the term "recombinant ASA protein" refers to any molecule or a portion of a molecule that can substitute for at least partial activity of naturally-occurring Arylsulfatase A (ASA) protein or rescue one or more phenotypes or symptoms associated with ASA-deficiency. As used herein, the terms "recombinant ASA enzyme" and "recombinant ASA protein", and grammatical equivalents, are used inter-changeably. In some embodiments, the present invention is used to purify a recombinant ASA protein that is a polypeptide having an amino acid sequence substantially similar or identical to mature human ASA protein.

Typically, human ASA is produced as a precursor molecule that is processed to a mature form. This process generally occurs by removing the 18 amino acid signal peptide. Typically, the precursor form is also referred to as full-length precursor or full-length ASA protein, which contains 507 amino acids. The N-terminal 18 amino acids are cleaved, resulting in a mature form that is 489 amino acids in length. Thus, it is contemplated that the N-terminal 18 amino acids is generally not required for the ASA protein activity. The amino acid sequences of the mature form (SEQ ID NO:1) and full-length precursor (SEQ ID NO:2) of a typical wild-type or naturally-occurring human ASA protein are shown in Table 1.

TABLE 1

Human Arylsulfatase A

| | |
|---|---|
| Mature Form | RPPNIVLIFADDLGYGDLGCYGHPSSTTPNLDQLAAGG LRFTDFYVPVSLCTPSRAALLTGRLPVRMGMYPGVLVP SSRGGLPLEEVTVAEVLAARGYLTGMAGKWHLGVGPEG AFLPPHQGFHRFLGIPYSHDQGPCQNLTCFPPATPCDG GCDQGLVPIPLLANLSVEAQPPWLPGLEARYMAFAHDL MADAQRQDRPFFLYYASHHTHYPQFSGQSFAERSGRGP FGDSLMELDAAVGTLMTAIGDLGLLEETLVIFTADNGP ETMRMSRGGCSGLLRCGKGTTYEGGVREPALAFWPGHI APGVTHELASSLDLLPTLAALAGAPLPNVTLDGFDLSP LLLGTGKSPRQSLFFYPSYPDEVRGVFAVRTGKYKAHF FTQGSAHSDTTADPACHASSSLTAHEPPLLYDLSKDPG ENYNLLGGVAGATPEVLQALKQLQLLKAQLDAAVTFGP SQVARGEDPALQICCHPGCTPRPACCHCPDPHA (SEQ ID NO: 1) |
| Full-Length Precursor | MGAPRSLLLALAAGLAVARPPNIVLIFADDLGYGDLGC YGHPSSTTPNLDQLAAGGLRFTDFYVPVSLCTPSRAAL LTGRLPVRMGMYPGVLVPSSRGGLPLEEVTVAEVLAAR GYLTGMAGKWHLGVGPEGAFLPPHQGFHRFLGIPYSHD QGPCQNLTCFPPATPCDGGCDQGLVPIPLLANLSVEAQ PPWLPGLEARYMAFAHDLMADAQRQDRPFFLYYASHHT HYPQFSGQSFAERSGRGPFGDSLMELDAAVGTLMTAIG DLGLLEETLVIFTADNGPETMRMSRGGCSGLLRCGKGT TYEGGVREPALAFWPGHIAPGVTHELASSLDLLPTLAA LAGAPLPNVTLDGFDLSPLLLGTGKSPRQSLFFYPSYP DEVRGVFAVRTGKYKAHFFTQGSAHSDTTADPACHASS SLTAHEPPLLYDLSKDPGENYNLLGGVAGATPEVLQAL KQLQLLKAQLDAAVTFGPSQVARGEDPALQICCHPGCT PRPACCHCPDPHA (SEQ ID NO: 2) |

Thus, in some embodiments, a recombinant ASA protein purified by embodiments of the present invention is mature human ASA protein (SEQ ID NO:1). In some embodiments, a recombinant ASA protein purified by embodiments of the present invention may be a homologue or an analogue of mature human ASA protein. For example, a homologue or an analogue of mature human ASA protein may be a modified mature human ASA protein containing one or more amino acid substitutions, deletions, and/or insertions as compared to a wild-type or naturally-occurring ASA protein (e.g., SEQ ID NO:1), while retaining substantial ASA protein activity. Thus, in some embodiments, a recombinant ASA protein purified by embodiments of the present invention is substantially homologous to mature human ASA protein (SEQ ID NO:1). In some embodiments, a recombinant ASA protein purified by embodiments of the present invention has an amino acid sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO:1. In some embodiments, a recombinant ASA protein purified by embodiments of the present invention is substantially identical to mature human ASA protein (SEQ ID NO:1). In some embodiments, a recombinant ASA protein purified by embodiments of the present invention has an amino acid sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:1. In some embodiments, a recombinant ASA protein purified by embodiments of the present invention contains a fragment or a portion of mature human ASA protein.

Alternatively, a recombinant ASA protein purified by embodiments of the present invention is full-length ASA protein. In some embodiments, a recombinant ASA protein may be a homologue or an analogue of full-length human ASA protein. For example, a homologue or an analogue of full-length human ASA protein may be a modified full-length human ASA protein containing one or more amino acid substitutions, deletions, and/or insertions as compared to a wild-type or naturally-occurring full-length ASA protein (e.g., SEQ ID NO:2), while retaining substantial ASA protein activity. Thus, in some embodiments, a recombinant ASA protein purified by embodiments of the present invention is substantially homologous to full-length human ASA protein (SEQ ID NO:2). In some embodiments, a recombinant ASA protein purified by embodiments of the present invention has an amino acid sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO:2. In some embodiments, a recombinant ASA protein purified by embodiments of the present invention is substantially identical to SEQ ID NO:2. In some embodiments, a recombinant ASA protein purified by embodiments of the present invention has an amino acid sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:2. In some embodiments, a recombinant ASA protein purified by embodiments of the present invention contains a fragment or a portion of full-length human ASA protein. As used herein, a full-length ASA protein typically contains signal peptide sequence.

Homologues or analogues of human ASA proteins can be prepared according to methods for altering polypeptide sequence known to one of ordinary skill in the art such as are found in references that compile such methods. In some embodiments, conservative substitutions of amino acids include substitutions made among amino acids within the following groups: (a) M, I, L, V; (b) F, Y, W; (c) K, R, H; (d) A, G; (e) S, T; (f) Q, N; and (g) E, D. In some embodiments, a "conservative amino acid substitution" refers to an amino acid substitution that does not alter the relative charge or size characteristics of the protein in which the amino acid substitution is made.

In some embodiments, recombinant ASA proteins may contain a moiety that binds to a receptor on the surface of target cells to facilitate cellular uptake and/or lysosomal targeting. For example, such a receptor may be the cation-independent mannose-6-phosphate receptor (CI-MPR) which binds the mannose-6-phosphate (M6P) residues. In addition, the CI-MPR also binds other proteins including IGF-II. In some embodiments, a recombinant ASA protein contains M6P residues on the surface of the protein. In particular, a recombinant ASA protein may contain bis-phosphorylated oligosaccharides which have higher binding affinity to the CI-MPR. In some embodiments, a suitable enzyme contains up to about an average of about at least 20% bis-phosphorylated oligosaccharides per enzyme. In other embodiments, a suitable enzyme may contain about 10%, 15%, 18%, 20%, 25%, 30%, 35%, 40%, 45%, 50%, 55%, 60% bis-phosphorylated oligosaccharides per enzyme.

In some embodiments, recombinant ASA enzymes may be fused to a lysosomal targeting moiety that is capable of binding to a receptor on the surface of target cells. A suitable lysosomal targeting moiety can be IGF-I, IGF-II, RAP, p97, and variants, homologues or fragments thereof (e.g., including those peptide having a sequence at least 70%, 75%, 80%, 85%, 90%, or 95% identical to a wild-type mature human IGF-I, IGF-II, RAP, p97 peptide sequence). The lysosomal targeting moiety may be conjugated or fused to an ASA protein or enzyme at the N-terminus, C-terminus or internally.

Production of Recombinant ASA Proteins

The present invention may be used to purify a recombinant ASA protein produced by various means. For example, an ASA protein may be recombinantly produced by utilizing a host cell system engineered to express an ASA-encoding nucleic acid. Alternatively, an ASA protein may be produced by activating an endogenous ASA gene.

It is contemplated that the present invention can be used to purify a recombinant ASA protein produced using various expression system. Suitable expression systems include, for example, egg, baculovirus, plant, yeast, or mammalian cells.

In some embodiments, ASA enzymes are produced in mammalian cells. Non-limiting examples of mammalian cells that may be used in accordance with the present invention include BALB/c mouse myeloma line (NSO/1, ECACC No: 85110503); human retinoblasts (PER.C6, CruCell, Leiden, The Netherlands); monkey kidney CV1 line transformed by SV40 (COS-7, ATCC CRL 1651); human embryonic kidney line (HEK293 or 293 cells subcloned for growth in suspension culture, Graham et al., J. Gen Virol., 36:59, 1977); human fibrosarcoma cell line (e.g., HT1080); baby hamster kidney cells (BHK21, ATCC CCL 10); Chinese hamster ovary cells +/−DHFR (CHO, Urlaub and Chasin, Proc. Natl. Acad. Sci. USA, 77:4216, 1980); mouse sertoli cells (TM4, Mather, Biol. Reprod., 23:243-251, 1980); monkey kidney cells (CV1 ATCC CCL 70); African green monkey kidney cells (VERO-76, ATCC CRL-1 587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci., 383:44-68, 1982); MRC 5 cells; FS4 cells; and a human hepatoma line (Hep G2).

In some embodiments, inventive methods according to the present invention are used to purify recombinant ASA enzymes produced from human cells (e.g., HT1080). In some embodiments, inventive methods according to the present invention are used to purify recombinant ASA enzymes produced from CHO cells.

Typically, cells that are engineered to express recombinant ASA may comprise a transgene that encodes a recombinant ASA protein described herein. It should be appreciated that the nucleic acids encoding recombinant ASA may contain regulatory sequences, gene control sequences, promoters, non-coding sequences and/or other appropriate sequences for expressing the recombinant ASA. Typically, the coding region is operably linked with one or more of these nucleic acid components.

"Regulatory sequences" typically refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences. Sometimes, "regulatory sequences" are also referred to as "gene control sequences."

"Promoter" typically refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence that can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions.

The "3' non-coding sequences" typically refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor.

The "translation leader sequence" or "5' non-coding sequences" typically refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency.

Typically, the term "operatively linked" or "operably linked" refers to the association of two or more nucleic acid fragments on a single nucleic acid fragment so that the function of one is affected by the other. For example, a promoter is operatively linked with a coding sequence when it is capable of affecting the expression of that coding sequence (i.e., that the coding sequence is under the transcriptional control of the promoter). Coding sequences can be operatively linked to regulatory sequences in sense or antisense orientation.

The coding region of a transgene may include one or more silent mutations to optimize codon usage for a particular cell type. For example, the codons of an ASA transgene may be optimized for expression in a vertebrate cell. In some embodiments, the codons of an ASA transgene may be optimized for expression in a mammalian cell. In some embodiments, the codons of an ASA transgene may be optimized for expression in a human cell.

Optionally, a construct may contain additional components such as one or more of the following: a splice site, an enhancer sequence, a selectable marker gene under the control of an appropriate promoter, an amplifiable marker gene under the control of an appropriate promoter, and a matrix attachment region (MAR) or other element known in the art that enhances expression of the region where it is inserted.

Once transfected or transduced into host cells, a suitable vector can express extrachromosomally (episomally) or integrate into the host cell's genome.

Cell Culture Medium and Condition

Various cell culture medium and conditions may be used to produce a recombinant ASA protein. For example, a recombinant ASA protein may be produced in serum-containing or serum-free medium. In some embodiments, a recombinant ASA protein is produced in serum-free medium. In some embodiments, a recombinant ASA protein is produced in an animal free medium, i.e., a medium that lacks animal-derived components. In some embodiments, a recombinant ASA protein is produced in a chemically defined medium. As used herein, the term "chemically-defined nutrient medium" refers to a medium of which substantially all of the chemical components are known. In some embodiments, a chemically defined nutrient medium is free of animal-derived components such as serum, serum derived proteins (e.g., albumin or fetuin), and other components. In some cases, a chemically-defined medium comprises one or more proteins (e.g., protein growth factors or cytokines.) In some cases, a chemically-defined nutrient medium comprises one or more protein hydrolysates. In other cases, a chemically-defined nutrient medium is a protein-free media, i.e., a serum-free media that contains no proteins, hydrolysates or components of unknown composition.

In some embodiments, a chemically defined medium may be supplemented by one or more animal derived components. Such animal derived components include, but are not limited to, fetal calf serum, horse serum, goat serum, donkey serum, human serum, and serum derived proteins such as albumins (e.g., bovine serum albumin or human serum albumin). While the addition of serum is desirable because it contains constituents, such as vitamins, amino acids, growth factors, and hormones, it also constitutes a concentrated source of exogenous protein which can impede recombinant protein purification. For example, fetuin proteins are a family of related serum proteins that are secreted by cells, primarily hepatocytes, and have three characteristic domains (Brown W M, et al., Eur J Biochem. 1992 Apr. 1; 205(1):321-31). Fetuins are abundant during fetal life, and therefore, are often abundant in commercially available fetus-derived serums and constitute a major protein contaminant during purification. Thus, in some embodiments, a suitable medium is a xeno-free media, e.g., a medium that does not contain any bovine serum or bovine serum derived components. For example, a xeno-free medium may contain one or more of human serum albumin, human transferrin, human insulin, and human lipids. In some embodiments, a suitable medium contains fetuin-depleted serum. Fetuin may be depleted from serum using various methods known in the art. For example, fetuin may be depleted from serum by antibody affinity chromatography. (See, e.g., Toroian D and Price P A, Calcif Tissue Int (2008) 82:116-126). In some embodiments, a suitable medium is fetuin-free.

Various cell culture conditions may be used to produce recombinant ASA proteins at large scale including, but not limited to, roller bottle cultures, bioreactor batch cultures and bioreactor fed-batch cultures. In some embodiments, recombinant ASA protein is produced by cells cultured in suspense. In some embodiments, recombinant ASA protein is produced by adherent cells.

Purification of Recombinant Arylsulfatase A

Figure 2:
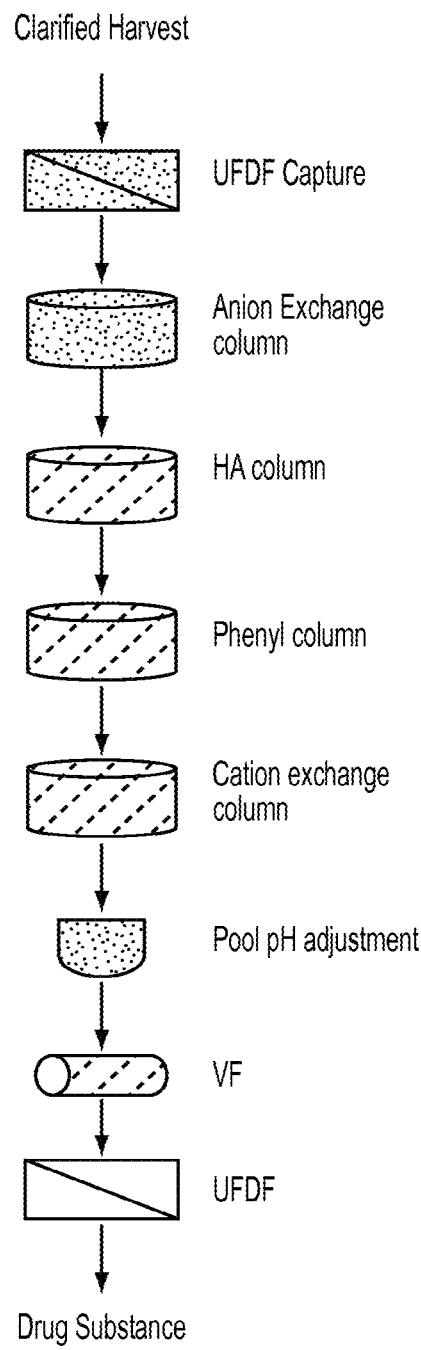
FIG. 2 illustrates a generalized flow diagram of an exemplary purification process involving a step of pooling eluate from cation exchange column and adjusting the pH of the pooled eluate.

Embodiments of the invention include purification processes for the production of Arylsulfatase A ("ASA"), particularly recombinant human ASA ("rhASA"), drug substances. A variety of techniques, in whole or in part, optionally with modifications as described herein, may be used to produce purified ASA drug substance. For example, FIG. 1 shows a generalized flow diagram of an embodiment of the invention. This exemplary purification process begins with thawing and pooling of rhASA unpurified bulk (UPB), which is then captured and filtered via ultrafiltration and diafiltration ("UFDF"). Following filtration, the captured material may be viral inactivated (not shown) before chromatographic purification. In the particular depicted embodiment, the next four purification process steps utilize in succession four chromatographic columns: a anion exchange column (e.g., a Q Sepharose Fast Flow ("Q-FF") column), a ceramic hydroxyapatite Type I (HA) column, a phenyl column, and a cation exchange (e.g., SP) column. After the fourth and final chromatography step, the SP eluate is concentrated and diafiltered using tangential flow ultrafiltration. The resultant filtrate is then viral filtered (e.g., through a Planova® 20N viral reduction filter) followed by a second concentration and diafiltration step to achieve a final target protein concentration. By comparison, FIG. 2 depicts another exemplary embodiment of the invention. The process proceeds as in FIG. 1, optionally using one or more different chromatographic resins (e.g., a TMAE anionic exchange resin). After the fourth and final chromatography step, however, the SP eluate is pooled, and the pH of the pool is adjusted. In some embodiments, the pH is adjusted to between 5.5 and 6.5 (e.g., about 6.0). The resultant pH-adjusted cation exchange eluate is then viral filtered followed by a single concentration and diafiltration step to achieve a final target protein concentration. Optional refinements of these processes and additional embodiments are described herein.

As used herein, a "contaminant" is a material that is different from the desired polypeptide product, e.g., arylsulfatase A (ASA). The contaminant may be a variant of the desired polypeptide (e.g., a deamidated variant or an amino-aspartate variant of the desired polypeptide) or another molecule, for example, polypeptide, nucleic acid, and endotoxin.

As used herein, by "purifying" a polypeptide from a composition or sample comprising the polypeptide and one or more contaminants is meant increasing the degree of purity of the polypeptide in the composition or sample by removing (completely or partially) at least one contaminant from the composition or sample. A "purification step" may be part of an overall purification process resulting in a composition comprising at least about 20%, 30%, 40%, 50%, 60%, 70%, 80%, 90%, 95%, 99%, 99.5%, 99.6%, 99.7%, 99.8%, or 99.9% by weight of the polypeptide of interest, based on total weight of the composition. The purity of arylsulfatase A can be measured by, e.g., one or more of: host cell protein (HCP) Western blot, SDS-PAGE Coomassie staining, SDS-PAGE silver staining, reverse phase HPLC, and size exclusion HPLC. In some embodiments, the specific activity of the purified arylsulfatase A is at least about 50 U/mg, 60 U/mg, 70 U/mg, 80 U/mg, 90 U/mg, 100 U/mg, 110 U/mg, 120 U/mg, 130 U/mg, 140 U/mg, e.g., as determined by a method described herein. In some embodiments, the purified recombinant ASA has a specific activity ranging from about 50-200 U/mg (e.g., about 50-190 U/mg, 50-180 U/mg, 50-170 U/mg, 50-160 U/mg, 50-150 U/mg, 50-140 U/mg, 50-130 U/mg, 50-120 U/mg, 50-110 U/mg, 50-100 U/mg, 60-140 U/mg, 60-130 U/mg, 60-120 U/mg, 60-110 U/mg, 60-100 U/mg, 70-140 U/mg, 70-130 U/mg, 70-120 U/mg, 70-110 U/mg, 70-100 U/mg, 80-140 U/mg, 80-130 U/mg, 80-120 U/mg, 80-110 U/mg, 80-100 U/mg, 90-140 U/mg, 90-130 U/mg, 90-120 U/mg, 90-110 U/mg, 90-100 U/mg, 100-140 U/mg, 100-130 U/mg, 100-120 U/mg, 100-110 U/mg, 110-140 U/mg, 110-130 U/mg, 110-120 U/mg, 120-140 U/mg, 120-130 U/mg, or 130-140 U/mg), e.g., as determined by a method described herein.

A starting material for the purification process is any impure preparation. For example, an impure preparation may be unprocessed cell culture medium containing recombinant ASA protein secreted from the cells (e.g., mammalian cells) producing ASA protein or raw cell lysates containing ASA protein. In some embodiments, an impure preparation may be partially processed cell medium or cell lysates. For example, cell medium or cell lysates can be concentrated, diluted, treated with viral inactivation, viral processing or viral removal. In some embodiments, viral removal may utilize nanofiltration and/or chromatographic techniques, among others. In some embodiments, viral inactivation may utilize solvent inactivation, detergent inactivation, pasteurization, acidic pH inactivation, and/or ultraviolet inactivation, among others. Cell medium or cell lysates may also be treated with protease, DNases, and/or RNases to reduce the level of host cell protein and/or nucleic acids (e.g., DNA or RNA). In some embodiments, unprocessed or partially processed biological materials (e.g., cell medium or cell lysate) may be frozen and stored at a desired temperature (e.g., 2-8° C., -4° C., -25° C., -75° C.) for a period time and then thawed for purification. As used herein, an impure preparation is also referred to as starting material or loading material.

The purification methods described herein can include, but not limited to, one or more of the following steps: depth filtration, viral inactivation, ion exchange chromatography (e.g., anion exchange chromatography, and/or cation exchange chromatography), mixed mode chromatography, hydrophobic interaction chromatography, ultrafiltration/diafiltration, and viral removal filtration. In some embodiments, the purification methods described herein further include affinity chromatography.

In the chromatography steps, the appropriate volume of resin used when packed into a chromatography column is reflected by the dimensions of the column, i.e., the diameter of the column and the height of the resin, and varies depending on e.g., the amount of protein in the applied solution and the binding capacity of the resin used. However, it is within the scope of the present disclosure to increase the scale of the production process as well as the purification process in order to obtain production and purification of ASA on an industrial scale. Accordingly parameters such as column size, diameter, and flow rate can be increased in order to comply with the speed and efficiency of such large-scale production. In some embodiments, the diameter of the column ranges from about 50-100 mm, the volume ranges from about 100-300 ml, and flow rate is between about 40-400 cm/hour (e.g., between about 100 cm/hour and 150 cm/hour) or about 5 to 100 ml.

Ultrafiltration—Capture

In some embodiments of the invention, the purification methods disclosed herein include one or more steps of upstream ultrafiltration to capture ASA (e.g., human recombinant ASA) produced from a perfusion bioreactor. Ultrafiltration, as used herein, refers to membrane filtration with filter pore sizes on the magnitude of 0.001 and 0.1 μm, which may be used for concentrating and desalting dissolved molecules (proteins, peptides, nucleic acids, carbohydrates, and other biomolecules), exchanging buffers, and gross fractionation. Methods of ultrafiltration for use in embodiments of the invention include tangential flow ultrafiltration or crossflow filtration.

Tangential flow filtration and ultrafiltration, as used herein, refers to arrangements where the feed stream passes parallel to the membrane face as one portion passes through the membrane (permeate) while the remainder (retentate) is recirculated back to the feed reservoir. In some embodiments, pore size of tangential flow ultrafiltration filters is chosen to allow recombinant ASA to permeate through the filter. In other embodiments, pore size is chosen so as to retain substantially all ASA in the feed passing over the filter. As noted elsewhere, ASA exists as a 480 kDa octamer in acidic conditions (pH≤about 5.0), but dissociates into dimers at neutral pH levels. Thus, the pH of the feed may be adjusted in combination with selection of appropriate pore size to either retain ASA on the filter membrane or allow it to pass through as a permeate.

Pore size may be selected with molecular weight cutoffs of at least 10 kDa, at least 20 kDa, at least 30 kDa, at least 40 kDa, at least 50 kDa, at least 60 kDa, at least 70 kDa, at least 80 kDa, at least 90 kDa, at least 100 kDa, at least 300 kDa, at least 400 kDa or at least 500 kDa. For example, a filter with a pore size of at least 10 kDa will retain in the feed a majority of proteins with molecular weights of approximately 11 kDa or higher. As another example, a filter of a pore size of at least 400 kDa will retain a majority of proteins with molecular weights higher than 400 kDa. In some embodiments, the feed retention rate is at least 75%, at least 80%, at least 85%, at least 90%, at least 95% or higher. Likewise, pore size may be selected for isolation of permeates of particular size. For example, a filter with a pore size of at least 500 kDa will allow a majority of proteins with molecular weights less than 500 kDa to permeate through. In some embodiments, the permeation rate is at least 75%, at least 80%, at least 85%, at least 90%, at least 95% or higher.

Filtration area or capacity may also be optimized for use in the processes disclosed herein. Considerations impacting selection of filtration area include robustness, cost, feed flow rate (i.e., crossflow velocity), transmembrane pressure, permeate flux rate, plant fit and throughput. In some embodiments, the permeate flux is about 50-100 liter per meter$^2$ per hour ("LMH"). In some embodiments, the feed flow is about 250-600 LMH, inclusive. In some embodiments, the feed flow is about 250-350 LMH, inclusive. In some embodiments, the feed flow is about 175-245 LMH, inclusive. In some embodiments, the feed flow is about 170-230 LMH, inclusive. In some embodiments, the feed flow is about 120-160 LMH, inclusive. In some embodiments, the feed flow is about 15-30 LMH, inclusive. In some embodiments, the fee flow is about 11-21 LMH, inclusive. In some embodiments, the filtration area is about 0.02 m$^2$, about 0.14 m$^2$, about 0.7 or about 3.5 m$^2$. In particular embodiments, the transmembrane pressure is about 55-60 psi, inclusive. In some embodiments, the transmembrane pressure is about 15-25 psi, inclusive. In some embodiments, the transmembrane pressure is about 10-20 psi, inclusive. In some embodiments, the transmembrane pressure is about 5-15 psi.

Ultrafiltration filters for use in embodiments of the invention may comprise membrane materials known to those of skill in the art, including but not limited to polyethersulfone and stabilized cellulose. One exemplary filter cassette for use in embodiments of the invention is the Sartorius ECO®. Another exemplary filter cassette for use in embodiments of the invention is the Sartorius HYDROSART® 30 kD Standard membrane.

Depth Filtration

The purification methods described herein can include one or more steps of depth filtration. Depth filters are the variety of filters that use a porous filtration medium to retain particles throughout the medium, rather than just on the surface of the medium. They contain filtration media having a graded density, which allows larger particles to be trapped near the surface of the filter while smaller particles penetrate the larger open areas at the surface of the filter, only to be trapped in the smaller openings nearer to the center of the filter. Although certain embodiments employ depth filtration steps only during the upstream recovery phase (i.e., before subsequent chromatographic purification steps), other embodiments employ depth filters during one or more additional phases of purification. In some embodiments of the invention, a Cuno Zeta Plus depth filter is used.

Depth filtration may optionally be followed by a 0.45 micron (±2 µm) filtration to remove particulates and reduce bioburden in preparation for downstream processing.

Viral Inactivation

The purification methods described herein can include one or more steps of viral inactivation. In some embodiments, the viral inactivation comprises a solvent and/or a detergent. The solvent or detergent can include, for example, polysorbate 80, Tri-n-Butyl-Phosphate (TnBP), or both. Viral inactivation may involve 3-24 hours of incubation in the solvent or detergent. In another embodiment, the viral inactivation comprises virus filtration, e.g., by using a Planova™ filter.

It is understood that these methods are intended to give rise to a preparation of an enzyme, which is substantially free of infectious viruses and which can be denoted a "virus-safe product". In addition, it is contemplated that the various methods can be used independently or in combination.

Virus-inactivation can be accomplished by the addition of one or more "virus-inactivating agents" to a solution comprising the enzyme. In some embodiments, a virus-inactivating step is performed prior to chromatographic purification steps (i.e., before loading the impure preparation onto the first chromatography column) in order to assure that the agent is not present in the final product in any amounts or concentrations that will compromise the safety of the product when used as a pharmaceutical or when the product is used for the preparation of a pharmaceutical; other embodiments employ depth filters during one or more additional phases of purification. For example, in some embodiments, an inventive method according to the invention further includes a step of viral removal after the last chromatography column.

The term "virus-inactivating agent" is intended to denote an agent (e.g., detergent) or a method, which can be used in order to inactivate lipid-enveloped viruses as well as non-lipid enveloped viruses. The term "virus-inactivating agent" is to be understood as encompassing both a combination of such agents and/or methods, whenever that is appropriate, as well as only one type of such agent or method.

Typical virus-inactivating agents are detergents and/or solvents, most typically detergent-solvent mixtures. It is to be understood that the virus inactivating agent is optionally a mixture of one or more detergents with one or more solvents. A wide variety of detergents and solvents can be used for virus inactivation. The detergent may be selected from the group consisting of non-ionic and ionic detergents and is selected to be substantially non-denaturating. Typically, a non-ionic detergent is used as it facilitates the subsequent elimination of the detergent from the rASA preparation in the subsequent purification steps. Suitable detergents are described, e.g. by Shanbrom et al., in U.S. Pat. Nos. 4,314,997, and 4,315,919. Typical detergents are those sold under the trademarks Triton X-100 and Tween 20 or Tween 80. Preferred solvents for use in virus-inactivating agents are di- or tri-alkylphosphates as described e.g. by Neurath and Horowitz in U.S. Pat. No. 4,764,369. A typical solvent is tri(n-butyl) phosphate (TnBP). An especially preferred virus-inactivating agent for the practice of the present invention is Tween 80, but, alternatively, other agents or combinations of agents can be used. The typical agent added in such a volume that the concentration of Tween-80 in the ASA-containing solution is within the range of about 0.5-4.0% by weight, preferably at a concentration of about 1% by weight. TnBP can then be added to a final concentration of 0.3% calculated based on the new volume of the sample containing ASA.

The virus-inactivation step is conducted under conditions inactivating enveloped viruses resulting in a substantially virus-safe rhASA-containing solution. In general, such conditions include a temperature of 4-37° C., such as 19-28° C., 23-27° C., typically about 25° C., and an incubation time found to be effective by validation studies. Generally, an incubation time of 1-24 hours is sufficient, preferably 10-18 hours, such as about 14 hours, to ensure sufficient virus inactivation. However, the appropriate conditions (temperature and incubation times) depend on the virus-inactivating agent employed, pH, and the protein concentration and lipid content of the solution.

It is contemplated that other methods for removal of or inactivating virus can also be employed to produce a virus-safe product, such as the addition of methylene blue with subsequent inactivation by radiation with ultraviolet light.

The purification methods described herein can include one or more steps of viral removal filtration. Typically, virus filtration is performed after purification of the enzyme by one or more steps of chromatography. In some embodiments, the virus filtration step is performed by passage of the ASA containing solution which is a result of a purification step through a sterile filter and subsequently passage of the sterile filtered solution through a nanofilter. By "sterile filter" is meant a filter, which will substantially remove all micro-organisms capable of propagating and/or causing infection. Whereas it is typical that the filter has a pore size of about 0.1 micron, the pore size could range between about 0.05 and 0.3 micron. It may be feasible to replace or combine virus filtration of the sample as performed in the purification process with contacting the sample with a detergent.

Some embodiments of the invention include at least two steps of viral inactivation and/or filtration. For example, viral inactivation before column chromatography may be combined viral removal after all of the chromatographic steps have been completed. Post-chromatographic viral removal can be done before or after one or more steps of ultrafiltration/diafiltration (UFDF) (e.g., tangential flow ultrafiltration). In a specific example, eluate is obtained from a final step of chromatographic purification (e.g., cation exchange (SP) chromatography), and the pH of the eluate pool is adjusted about 5.5, about 6.0, about 6.5 or about 7.0, followed by viral filtration. Thus, in certain embodiments, a single step of UFDF is preceded by viral filtration (e.g., using a Planova™ filter). In other example, eluate is obtained from a final step of chromatographic purification (e.g., cation exchange (SP) chromatography), is subjected to a first step of UFDF without pH adjustment, followed by viral filtration and a second step of UFDF.

In certain embodiments, pH-adjusted cation exchange eluate pool is viral filtered on a Planova 20N filter. In some embodiments, the yield relative to input following viral filtration of pH-adjusted cation exchange eluate is between about 90-100%; i.e., about 90%, about 95%, about 96%, about 97%, about 98%, about 99% or more, as assessed by A280 absorbance. Thus, in some embodiments, essentially no recombinant ASA is lost during viral filtration. The yield for viral filtration is significant as it verifies that pH adjustment to about 6.0 allows octamers of ASA (which are about 20 nm in diameter) to dissociate into dimeric form. Thus, the pore size of a viral filter may be selected to ensure that only the dimeric form is filtered (i.e., that the octameric form may be retained by the filter, or cause viral filter plugging). For examples, a viral filter with a pore size of 20 nm will retain the octameric form of ASA, but not the dimeric form.

Affinity Chromatography

The purification methods described herein can include one or more steps of affinity chromatography (e.g., immuno-affinity chromatography, immobilized metal ion affinity chromatography, and/or immobilized ligand affinity chromatography).

Briefly, affinity chromatography is a chromatographic technique which relies on highly specific interactions, such as, for example, between a receptor and ligand, an antigen and antibody, or an enzyme and substrate. As will be known by the person skilled in the art, selective molecules employed in an affinity chromatography step in the purification methods described herein may be based on various properties (e.g., three dimensional structure, glycosylation, etc.) of recombinantly produced ASA that can be exploited by the selective molecule. Exemplary selective molecules (or capture reagents) that can be utilized in an affinity chromatography step include protein A, protein G, an antibody, a metal ion (e.g., nickel), specific substrate, ligand or antigen. In some embodiments, a suitable selective molecule for an affinity chromatography step of the present invention utilizes an anti-Arylsulfatase A antibody (e.g., an anti-human Arylsulfatase A antibody). Suitable anti-Arylsulfatase A antibodies may be obtained commercially or through immunization of non-human animals (e.g., a mouse, rat, rabbit, chicken, goat, sheep, horse or other suitable animal for producing antibodies against a human protein).

Generally, a molecule of interest (e.g., recombinant ASA) is trapped on a solid or stationary phase or medium through interaction with a selective molecule, while other, undesired molecules are not trapped as they are not bound by the selective molecule(s). The solid medium may then be removed from the mixture, optionally washed, and the molecule of interest released from the entrapment by elution. In some embodiments, affinity columns may be eluted by changing the ionic strength through a gradient. For example, salt concentrations, pH, pI, and ionic strength may be used to separate or to form the gradient to separate.

In some embodiments, a recombinant ASA protein may be produced with a tag in order to facilitate purification by affinity chromatography. As will be known by the person skilled in the art, protein tags may include, for example, glutathione-S-transferase (GST), hexahistidine (His), maltose-binding protein (MBP), among others. In some embodiments, lectins are used in affinity chromatography to separate components within the sample. For example, certain lectins specifically bind a particular carbohydrate molecule and can be used to separate glycoproteins from non-glycosylated proteins, or one glycoform from another glycoform.

Ion Exchange Chromatography

The purification methods described herein can include one or more steps of ion exchange chromatography (e.g., anion exchange chromatography and/or cation exchange chromatography).

As will be known by the person skilled in the art, ion exchangers (e.g., anion exchangers and/or cation exchangers) may be based on various materials with respect to the matrix as well as to the attached charged groups. For example, the following matrices may be used, in which the materials mentioned may be more or less crosslinked: agarose based (such as SEPHAROSE™ CL-6B, SEPHAROSE™ Fast Flow and SEPHAROSE™ High Performance), cellulose based (such as DEAE SEPHACEL®), dextran based (such as SEPHADEX®), silica based and synthetic polymer based.

The ion exchange resin can be prepared according to known methods. Typically, an equilibration buffer, which allows the resin to bind its counter ions, can be passed through the ion exchange resin prior to loading the sample or composition comprising the polypeptide and one or more contaminants onto the resin. Conveniently, the equilibration buffer can be the same as the loading buffer, but this is not required.

In an optional embodiment of the invention, the ion exchange resin can be regenerated with a regeneration buffer after elution of the polypeptide, such that the column can be re-used. Generally, the salt concentration and/or pH of the regeneration buffer can be such that substantially all contaminants and the polypeptide of interest are eluted from the ion exchange resin. Generally, the regeneration buffer has a very high salt concentration for eluting contaminants and polypeptide from the ion exchange resin.

Anion Exchange Chromatography

Embodiments of the invention include, for example, providing a sample of arylsulfatase A (e.g., recombinant arylsulfatase A), and subjecting the sample to anion exchange chromatography, e.g., anion exchange chromatography described herein. For the anion exchange resin, the charged groups which are covalently attached to the matrix can be, for example, diethylaminoethyl (DEAE), quaternary aminoethyl (QAE), and/or quaternary ammonium (Q). In some embodiments, the anion exchange resin employed is a Q Sepharose column. The anion exchange chromatography can be performed using, e.g., Q SEPHAROSE™ Fast Flow, Q SEPHAROSE™ High Performance, Q SEPHAROSE™ XL, CAPTO™ Q, DEAE, TOYOPEARL GIGACAP® Q, FRACTOGEL® TMAE (trimethylaminoethyl, a quarternary ammonia resin), ESHMUNO™ Q, NUVIA™ Q, or UNOSPHERE™ Q. Other anion exchangers can be used within the scope of the invention, including but not limited to, but are not limited to, quaternary amine resins or "Q-resins" (e.g., CAPTO™-Q, Q-SEPHAROSE®, QAE SEPHADEX®); diethylaminoethane (DEAE) resins (e.g., DEAE-TRISACRYL®, DEAE SEPHAROSE®, benzoylated naphthoylated DEAE, diethylaminoethyl SEPHACEL®); AMBERJET® resins; AMBERLYST® resins; AMBERLITE® resins (e.g., AMBERLITE® IRA-67, AMBERLITE® strongly basic, AMBERLITE® weakly basic), cholestyramine resin, ProPac® resins (e.g., PROPAC® SAX-10, PROPAC® WAX-10, PROPAC® WCX-10); TSK-GEL® resins (e.g., TSKgel DEAE-NPR; TSKgel DEAE-5PW); and ACCLAIM® resins. In some embodiments, subjecting the sample of arylsulfatase A to the anion exchange chromatography is performed at a temperature about 23° C. or less, about 18° C. or less, or about 16° C. or less, e.g., about 23° C., about 20° C., about 18° C., or about 16° C.

Typical mobile phases for anionic exchange chromatography include relatively polar solutions, such as water, acetonitrile, organic alcohols such as methanol, ethanol, and isopropanol, or solutions containing 2-(N-morpholino)-ethanesulfonic acid (MES). Thus, in certain embodiments, the mobile phase includes about 0%, 1%, 2%, 4%, 6%, 8%, 10%, 12%, 14%, 16%, 18%, 20%, 25%, 30%, 35%, 40%, 45%, 50%, 55%, 60%, 65%, 70%, 75%, 80%, 85%, 90%, 95%, or about 100% polar solution. In certain embodiments, the mobile phase comprises between about 1% to about 100%, about 5% to about 95%, about 10% to about 90%, about 20% to about 80%, about 30% to about 70%, or about 40% to about 60% polar solution at any given time during the course of the separation.

In certain embodiments, rASA is loaded at a binding capacity about 23 AU/L resin or less, e.g., about 19 AU/L resin or less, about 15 AU/L resin or less, or about 12 AU/L resin or less, e.g., between about 12 AU/L resin and about 15 AU/L resin, or between about 15 AU/L resin and about 19 AU/L resin. In some embodiments, the sample of arylsulfatase A is loaded onto the anion exchange chromatography column at a binding capacity at least about 4.5 g/L resin (e.g., at least about 5 g/L resin, 6 g/L resin, 7 g/L resin, 8 g/L resin, 9 g/L resin, 10 g/L resin, 11 g/L resin, 12 g/L resin, 13 g/L resin, 14 g/L resin, or 15 g/L resin). In some embodiments, the sample of arylsulfatase A is loaded onto the anion exchange chromatography column at a binding capacity ranging between about 4.5-20 g/L resin (e.g., ranging between about 5-20 g/L resin; 5-19 g/L resin, 5-18 g/L resin, 5-17 g/L resin, 5-16 g/L resin, 5-15 g/L resin, 7.5-20 g/L resin, 7.5-19 g/L resin, 7.5-18 g/L resin, 7.5-17 g/L resin, 7.5-16 g/L resin, 7.5-15 g/L resin, 10-20 g/L resin, 10-19 g/L resin, 10-18 g/L resin, 10-17 g/L resin, 10-16 g/L resin, or 10-15 g/L resin).

The aqueous solution comprising the ASA and contaminant(s) can be loaded onto the anionic resin as a mobile phase using a loading buffer that has a salt concentration and/or a pH such that the polypeptide and the contaminant bind to the anion exchange resin. The resin can then be washed with one or more column volumes of loading buffer followed by one or more column volumes of wash buffer wherein the salt concentration is increased. Finally, the ASA can be eluted by an elution buffer of increasing salt concentration. Optionally, elution of the enzyme may also be mediated by gradually or stepwise decreasing the pH. The fractions containing ASA activity can be collected and combined for further purification.

In some embodiments, loading the sample of arylsulfatase A onto the anion exchange chromatography column is performed with a loading buffer. In one embodiment, the loading buffer does not contain sodium chloride. In another embodiment, the loading buffer contains sodium chloride. For example, the sodium chloride concentration of the loading buffer is from about 1 mM to about 25 mM, e.g., from about 1 mM to about 10 mM, from about 1 mM to about 5 mM, or from about 5 mM to about 10 mM. In some embodiments, salt concentration in the mobile phase is a gradient (e.g., linear or non-linear gradient). In some embodiments, salt concentration in the mobile phase is constant. In some embodiments, salt concentration in the mobile phase may increase or decrease stepwise. In some embodiments, loading the sample of arylsulfatase A onto the anion exchange chromatography column is performed at a pH from about 5 to about 9, e.g., from about 6 to about 8, e.g., about 7.

In some embodiments, washing the anion exchange chromatography column is performed with one or more washing buffers. For example, washing the anion exchange column can include two or more (e.g., a first and a second) washing steps, each using a different washing buffer. In one embodiment, the washing buffer does not contain sodium chloride. In another embodiment, the washing buffer contains sodium chloride. For example, the sodium chloride concentration of the washing buffer is from about 50 mM to about 200 mM, e.g., from about 50 mM to about 150 mM, from about 100 mM to about 200 mM, or from about 100 mM to about 150 mM, e.g., about 80 mM, about 100 mM, about 120 mM, or about 140 mM. In some embodiments, washing the anion exchange chromatography column is performed at a pH from about 5 to about 9, e.g., from about 6 to about 8, e.g., about 7.

In one embodiment, the elution buffer contains sodium phosphate. For example, the sodium phosphate concentration of the elution buffer is from about 20 mM to about 50 mM, e.g., from about 25 mM to about 45 mM, e.g., about 30 mM, about 35 mM, or about 40 mM. In another embodiment, the elution buffer does not contain sodium chloride. In yet another embodiment, the elution buffer contains sodium chloride. For example, the sodium chloride concentration of the elution buffer is from about 200 mM to about 300 mM, e.g., from about 240 mM to about 280 mM. In some embodiments, eluting the arylsulfatase A from the anion exchange chromatography column is performed at a pH from about 5 to about 9, e.g., from about 6 to about 8, e.g., about 7.

In some embodiments, eluting the arylsulfatase A from the anion exchange chromatography column includes one or more steps of elution peak collection. For example, the elution peak collection starts from about 50 mAU at the ascending side to about 50 mAU at the descending side, e.g., from about 100 mAU at the ascending side to about 50 mAU at the descending side, from about 200 mAU at the ascending side to about 50 mAU at the descending side, from about 50 mAU at the ascending side to about 100 mAU at the descending side, from about 50 mAU at the ascending side to about 200 mAU at the descending side, or from about 100 mAU at the ascending side to about 100 mAU at the descending side, e.g., as determined by spectrophotometry, e.g., at 280 nM.

It is apparent to the person of ordinary skill in the art that numerous different buffers may be used in the loading, washing, and elution steps. Typically, however, the column can be equilibrated with 1-10 column washes of a buffer comprising 0.05 M MES-Tris, pH 7.0. As of convenience the sample can be loaded in the buffer from the previous step of the purification process, or the sample can be loaded using a loading buffer. The column can be washed with 1-10 column volumes of the buffer used for equilibration, followed by a washing buffer comprising 0.02 MES-Tris, 0.12 M NaCl, pH 7.0. Alternatively, the column can be equilibrated, loaded, and washed with any other equilibration, loading, and washing buffers described herein for anion exchange chromatography. The sample can be eluted in a buffer comprising 0.02 MES-Tris, 0.26 M NaCl, pH 7.0. Alternatively, the sample can be eluted in any other elution buffer described herein for anion exchange chromatography.

The loading buffer, washing buffer, and elution buffer described herein can include one or more buffering agents. For example, the buffering agent can be TRIS, HEPES, MOPS, PIPES, SSC, MES, sodium phosphate, sodium acetate, or a combination thereof. The concentration of the buffering agent is between about 1 mM and about 500 mM, e.g., between about 10 mM and about 250 mM, between about 20 mM and about 100 mM, between about 1 mM and 5 mM, between about 5 mM and 10 mM, between about 10 mM and 50 mM, or between about 50 mM and about 100 mM, e.g., about 1 mM, about 5 mM, about 10 mM, about 20 mM, about 30 mM, about 40 mM, or about 50 mM.

Yield, activity and purity following anion exchange chromatography may vary. In some embodiments, the arylsulfatase A activity yield is at least about 75%, e.g., at least about 85%, e.g., between about 85% and about 99%, or between about 90% and about 99%. In some embodiments, the protein yield (AU or Absorbance Units) is from about 10% to 50%, e.g., from about 20% to about 35%, or from about 25% to about 30%, e.g., as determined by spectrophotometry, e.g., at 280 nm. In some embodiments (e.g., those using a TMAE column as described below), the elution pool protein activity yield (AU or Absorbance Units) is from about 70% to 400%, e.g., from about 80% to about 390%, or from about 90% to about 350%, or from about 100% to 150%, greater than at least 95%, e.g., as determined by spectrophotometry, e.g., at 280 nm. In some embodiments (e.g., those using a TMAE column as described below), the host cell protein (HCP) log reduction value (LRV) is between about 0.5 and about 1.1, e.g., between about 0.6 and 0.9, or between about 0.7 and 0.8. In some embodiments (e.g., those using a TMAE column as described below), the purity is at least 75%, e.g., at least 80%, at least 85%, at least 90% or higher, as determined by, for example, capillary electrophoresis-SDS PAGE. In preferred embodiments, the activity yield, HCP LRV and purity (as determined by capillary electrophoresis-SDS PAGE) following anion exchange chromatography are at least about 90%, at least about 0.6 and at least about 80%, respectively.

In preferred embodiments of the invention, an anionic exchange column with a high loading capacity is used. In certain embodiments of the invention, the column is characterized by a loading range between about 3-20 g/L (i.e., about 5-15 g/L, about 10-15 g/L, about 10-20 g/L). In some embodiments, the loading capacity is significantly greater than 4.3 g/L (e.g., is or greater than about 10 g/L, 12.5 g/L, 15 g/L, 17.5 g/L, or 20 g/L). In certain embodiments, the binding capacity of the resin is between about 75-100 AU/L (e.g. about 75 AU/L, about 80 AU/L, about 85 AU/L, about 90 AU/L, about 95 AU/L). In certain embodiments, the loading capacity is greater than about 80 AU/L. In some embodiments, the high load capacity column is a TMAE column. In particular embodiments, the column is selected from the group consisting of a Fractogel® TMAE column, a Nuvia Q column, a Q Sepharose Fast Flow column, a Capto Q column, a Q Sepharose XL column, a Eshmuno Q column, a UNOsphere Q column, or a GigaCap Q column.

In particular embodiments of the invention, a TMAE column is pre-equilibrated with a buffer comprising about 20 mM MES-Tris and 1000 mM NaCl at a pH of 7.0. In certain embodiments, the column is equilibrated with a buffer comprising 50 mM MES-Tris at a pH of 7.0. In some embodiments, the load flow rate of the TMAE column is about 75-125 cm/hr (i.e., about 75-115 cm/hr, about 75-110 cm/hr, about 75-105 cm/hr, about 75-100 cm/hr, about 85-115 cm/hr, about 85-110 cm/hr, about 85-105 cm/hr, about 85-100 cm/hr, about 95-115 cm/hr, about 95-110 cm/hr, about 95-105 cm/hr, about 95-100 cm/hr, about 100-120 cm/hr, about 100-115 cm/hr, about 100-110 cm/hr, about 100 cm/hr). Loading conditions may be optimized and assessed by A280 absorbance as described herein.

In particular embodiments utilizing a TMAE column (e.g., a Fractogel TMAE column), very little product is lost in the flow through during loading, even at loading capacities greater than 15 g/L. The capability of increasing loading capacity while minimizing flow-through loss is a significant improvement in purification methodology. In particular embodiments of the invention, the amount of flow-through product loss is less than 30% of the load (e.g. less than about 25%, less than about 20%, less than about 15%, less than about 10%, or less than about 5%).

After loading, in some embodiments, a TMAE column is washed at least once. In particular embodiments, the column is washed twice. A first or second wash buffer may comprise an optimized level of sodium chloride. In some embodiments, the amount of sodium chloride is a first or second wash buffer is between about 50-150 mM (e.g. about 50-140 mM, about 50-130 mM, about 50-120 mM, about 50-110 mM, about 50-100 mM, about 50-90 mM, about 50-80 mM, about 80-150 mM, about 80-140 mM, about 80-130 mM, about 80-120 mM, about 80-110 mM, about 80-100 mM, about 80-90 mM, about 80 mM, or about 120 mM). In some embodiments, a first wash buffer comprises 50 mM MES-Tris at pH 7.0. In some embodiments, a second wash buffer comprises, 20 mM MES-Tris, 100 mM NaCl at pH 7.0. Further optimization of wash conditions, particularly second wash conditions, is encompassed within embodiments of the present invention. For example, increasing the salt concentration of a second wash may improve host cell protein (HCP) log reduction values (LRV) and overall purity, but decrease both activity and A280 yield. As described herein, particular washing conditions must be balanced with the elution conditions described below in order to provide the optimal combination of purity, activity and yield.

In embodiments of the invention, recombinant ASA bound to a TMAE column is eluted with an elution buffer. In some embodiment, the amount of sodium chloride in the elution buffer is optimized. In particular embodiments, the amount of sodium chloride in the elution buffer is between about 150-300 mM (e.g. about 150-290 mM, about 150-280 mM, about 150-270 mM, about 150-260 mM, about 150-250 mM, about 150-240 mM, about 150-230 mM, about 150-220 mM, about 150-210 mM, about 170-290 mM, about 170-280 mM, about 170-270 mM, about 170-260 mM, about 170-250 mM, about 170-240 mM, about 170-230 mM, about 170-220 mM, about 170-210 mM about 180-290 mM, about 180-280 mM, about 180-270 mM, about 180-260 mM, about 180-250 mM, about 180-240 mM, about 180-230 mM, about 180-220 mM, about 180-210 mM, about 180, about 220 or about 260). In a particular example, the elution buffer comprises 50 mM MES-Tris and 1M NaCl at a pH of 7.0. In some embodiments, the A280 yield following elution is greater than 60% of the load (e.g., about 60%, about 70%, about 80% or higher). Further optimization of elution conditions is encompassed within embodiments of the present invention. For example, increase elution salt concentration (i.e., conductivity) provides better yield but results in poorer purity and HCP removal. And as noted above, particular washing conditions must be balanced with the elution conditions in order to provide the optimal combination of purity, activity and yield.

Cation Exchange Chromatography

In some embodiments, the method further includes subjecting the sample of arylsulfatase A to cation exchange chromatography, e.g., sulfopropyl (SP) cation exchange chromatography, e.g., as described herein. In some embodiments, the sample of arylsulfatase A is subjected to anion exchange chromatography prior to cation exchange chromatography. In a typical embodiment, the cation exchange chromatography comprises sulfopropyl (SP) cation exchange chromatography, but other cation chromatography membranes or resins can be used, for example, a MUSTANG™ S membrane, an S-SEPHAROSE™ resin, or a Blue SEPHAROSE™ resin. In some embodiments, the method further comprises concentrating and/or filtering the sample of arylsulfatase A, e.g., by ultrafiltration and/or diafiltration, e.g., by tangential flow ultrafiltration. The cation exchange chromatography can be performed at an optimized temperature, e.g., as described herein, to enhance target binding and/or decrease impurity binding. For example, the cation exchange chromatography can be performed at a temperature of about 23° C., 18° C., 16° C., or less.

In one embodiment, the cation exchange chromatography includes sulfopropyl (SP) cation exchange chromatography. In another embodiment, the cation exchange chromatography is a polishing step. The cation exchange chromatography (e.g., sulfopropyl (SP) cation exchange chromatography) can be performed using, e.g., one or more of: TOYOPEARL® SP-650, TOYOPEARL® SP-550, TSK-GEL® SP-3PW, TSKGEL® SP-5PW, SP SEPHAROSE™ Fast Flow, SP SEPHAROSE™ High Performance, SP SEPHAROSE™ XL, SARTOBIND® S membrane, POROS® HS50, UNOSPHERE™ S, and MACROCAP™ S.

The aqueous solution comprising the arylsulfatase A and contaminant(s) can be loaded onto the cationic resin using a loading buffer that has a salt concentration and/or a pH such that the polypeptide and the contaminant bind to the cation exchange resin. The resin can then be washed with one or more column volumes of equilibration butter or loading buffer, and optionally followed by one or more column volumes of wash buffer wherein the salt concentration is increased. Finally, the arylsulfatase A can be eluted in an elution buffer. The fractions containing arylsulfatase A activity can be collected and combined for further purification.

In a typical embodiment, the NaCl concentration and/or pH of the loading buffer, washing buffer, and/or elution buffer, can be optimized, e.g., as described herein, to enhance target binding and/or decrease impurity binding. In some embodiments, the NaCl concentration in the loading buffer is about 20 mM, 15 mM, 10 mM, or less. In some embodiments, the loading buffer has a pH of about 4.5, 4.3, 4.0, or less. In some embodiments, the NaCl concentration in the washing buffer is about 20 mM, 15 mM, 10 mM, or less. In some embodiments, the NaCl concentration in the elution buffer is about 55 mM, 50 mM, 45 mM, 40 mM, or less.

In some embodiments, subjecting the sample of arylsulfatase A to a cation exchange chromatography includes: loading the sample of arylsulfatase A onto a cation chromatography column (e.g., a sulfopropyl (SP) cation exchange column), washing the cation exchange chromatography column, and eluting the arylsulfatase A from the column. In some embodiments, the columns can be equilibrated with more than 3, e.g., 5 to 10 column volumes of 0.01 M NaAc, 0.01 M NaCl, 0.03 M acetic acid, pH 4.2.

In some embodiments, the sample can be loaded in the buffer from the previous step of the purification process, or the sample can be loaded using a loading buffer. In one embodiment, the loading buffer contains sodium chloride. For example, the sodium chloride concentration of the loading buffer is from about 1 mM to about 25 mM, e.g., from about 5 mM to about 20 mM, e.g., about 5 mM, about 10 mM, about 15 mM, or about 20 mM. In another embodiment, the loading buffer contains sodium acetate. For example, the sodium acetate concentration of the loading buffer is from about 10 mM to about 100 mM, e.g., about 20 mM, about 40 mM, or about 60 mM. In some embodiments, loading the sample of arylsulfatase A onto the cation exchange chromatography column is performed at a pH from about 3.0 and about 6.0, e.g., from about 4.0 and about 5.0, e.g., about 4.0, about 4.3, or about 4.5. In some embodiments, the sample of arylsulfatase A is loaded onto the cation exchange chromatography column at a binding capacity about 15 AU/L resin or less, e.g., about 14 AU/L resin or less, or about 12 AU/L resin or less, e.g., between about 10 AU/L resin and about 14 AU/L resin, or between about 10 AU/L resin and about 12 AU/L resin.

In some embodiments, washing the cation exchange chromatography column is performed with one or more washing buffers. For example, washing the cation exchange column can include two or more (e.g., a first and a second) washing steps, each using a different washing buffer. The column can be washed with 1-10 column volumes of the buffer used for equilibration. Alternatively, the column can be equilibrated, loaded, and washed with any other equilibration, loading, and washing buffers described herein for cation exchange chromatography. In one embodiment, the washing buffer contains sodium chloride. For example, the sodium chloride concentration of the washing buffer is from about 1 mM to about 25 mM, e.g., from about 5 mM to about 20 mM, or from about 10 mM to about 15 mM, e.g., about 5 mM, about 10 mM, about 15 mM, or about 20 mM. In another embodiment, the washing buffer contains sodium acetate. For example, the sodium acetate concentration of the loading buffer is from about 10 mM to about 100 mM, e.g., about 20 mM, about 40 mM, or about 60 mM. In some embodiments, washing the cation exchange chromatography column is performed at a pH from about 3.0 and about 6.0, e.g., from about 4.0 and about 5.0, e.g., about 4.0, about 4.3, or about 4.5.

In some embodiments, eluting the arylsulfatase A from the cation exchange chromatography column is performed with an elution buffer. In one embodiment, the elution buffer contains sodium chloride. For example, the sodium chloride concentration of the elution buffer is from about 25 mM to about 75 mM, e.g., from about 45 mM to about 60 mM, e.g., about 45 mM, about 50 mM, about 55 mM, or about 55 mM. In some embodiments, eluting the arylsulfatase A from the cation exchange chromatography column is performed at a pH from about 3.0 and about 6.0, e.g., from about 4.0 and about 5.0, e.g., about 4.0, about 4.3, or about 4.5. Thus, as one particular example, the sample can be eluted in a buffer comprising 0.02 M NaAc, 0.05 M NaCl, pH 4.5. Alternatively, the sample can be eluted in any other elution buffer described herein for cation exchange chromatography.

In some embodiments, eluting the arylsulfatase A from the cation exchange chromatography column includes one or more steps of elution peak collection. For example, the elution peak collection starts from about 50 mAU at the ascending side to about 50 mAU at the descending side, e.g., from about 100 mAU at the ascending side to about 50 mAU at the descending side, from about 200 mAU at the ascending side to about 50 mAU at the descending side, from about 50 mAU at the ascending side to about 100 mAU at the descending side, from about 50 mAU at the ascending side to about 200 mAU at the descending side, or from about 100 mAU at the ascending side to about 100 mAU at the descending side, e.g., as determined by spectrophotometry, e.g., at 280 nM. Collected eluate peaks may be pooled.

The loading buffer, washing buffer, and elution buffer described herein can include one or more buffering agents. For example, the buffering agent can be TRIS, HEPES, MOPS, PIPES, SSC, MES, sodium phosphate, sodium acetate, or a combination thereof. The concentration of the buffering agent is between about 1 mM and about 500 mM, e.g., between about 10 mM and about 250 mM, between about 20 mM and about 100 mM, between about 1 mM and 5 mM, between about 5 mM and 10 mM, between about 10 mM and 50 mM, or between about 50 mM and about 100 mM, e.g., about 1 mM, about 5 mM, about 10 mM, about 20 mM, about 30 mM, about 40 mM, or about 50 mM.

In some embodiments, subjecting the sample of arylsulfatase A to the cation exchange chromatography is performed at a temperature about 23° C. or less, about 18° C. or less, or about 16° C. or less, e.g., about 23° C., about 20° C., about 18° C., or about 16° C. In some embodiments, subjecting the sample of arylsulfatase A to the cation exchange chromatography is performed between about 23° C. and about 16° C., e.g., at about 23° C., about 20° C., about 18° C., or about 16° C., and loading the sample of arylsulfatase A onto the cation exchange chromatography column is performed at a pH between about 4.5 and about 4.3, e.g., at about 4.5, about 4.4, or about 4.3. In some embodiments, subjecting the sample of arylsulfatase A to the cation exchange chromatography is performed at about 23° C. and loading the sample of arylsulfatase A onto the cation exchange chromatography column is performed at a pH about 4.5. In some embodiments, subjecting the sample of arylsulfatase A to the cation exchange chromatography is performed at about 23° C. and loading the sample of arylsulfatase A onto the cation exchange chromatography column is performed at a pH about 4.3. In some embodiments, subjecting the sample of arylsulfatase A to the cation exchange chromatography is performed at about 18° C. and loading the sample of arylsulfatase A onto the cation exchange chromatography column is performed at a pH about 4.5. In some embodiments, subjecting the sample of arylsulfatase A to the cation exchange chromatography is performed at about 18° C. and loading the sample of arylsulfatase A onto the cation exchange chromatography column is performed at a pH about 4.3.

The yield following cation exchange chromatography may vary. In some embodiments, the arylsulfatase A activity yield is at least about 75%, e.g., at least about 80%, e.g., between about 80% and about 105%. In some embodiments, the protein yield (AU or Absorbance Units) is from about 65% to 100%, e.g., from about 70% to about 95%, e.g., as determined by spectrophotometry, e.g., at 280 nm.

The purity and activity following cation exchange chromatography is greatly improved. In some embodiments, the host cell protein (HCP) log reduction value (LRV) is between about 1.0 and about 2.5, e.g., between about 1.5 and about 2.0 or between about 1.7 and about 1.9. The specific activity of the purified arylsulfatase A can be at least from about 50 U/mg to about 140 U/mg, e.g., at least about 70 U/mg, at least about 90 U/mg, at least about 100 U/mg, or at least about 120 U/mg, e.g., as determined by a method described herein. In some embodiments, the arylsulfatase A is purified to at least about 95%, at least about 98%, at least about 99%, at least about 99.5%, at least about 99.6%, at least about 99.7%, at least about 99.8%, or at least about 99.9%. The purity of arylsulfatase A can be measured by, e.g., one or more of: host cell protein (HCP) Western blot, SDS-PAGE Coomassie staining, SDS-PAGE silver staining, reverse phase HPLC, and size exclusion HPLC. In certain embodiments, decreasing the salt concentration of the loading buffer and lowering its pH enhances binding ASA to the cation exchange column but does not impact impurity binding. In other words, an optimal balance of salt concentration and pH, as set forth above, can increase yield after cation exchange chromatography without adversely affecting purity.

In some embodiments, the pH of a cation exchange eluate pool may be adjusted. In certain embodiments, the pH is adjusted immediately prior to viral filtration. Cation exchange eluate (e.g., SP eluate) may be pH adjusted to about 5.5, about 6.0 about 6.5 or about 7.0 using a pH adjustment buffer comprising 0.25M sodium phosphate, 1.33M sodium chloride, 0.34M sodium citrate, pH 7.0. In certain embodiments, the pH-adjusted SP eluate pool is viral filtered on a Planova 20N filter. In some embodiments, the yield relative to input following viral filtration of pH-adjusted cation exchange eluate is between about 90-100%; i.e., about 90%, about 95%, about 96%, about 97%, about 98%, about 99% or more, as assessed by A280 absorbance. The yield for viral filtration is significant as it verifies that pH adjustment to about 6.0 allows octamers of ASA (which are about 20 nm in diameter) to dissociate into dimeric form. Thus, the pore size of a viral filter may be selected to ensure that only the dimeric form is filtered (i.e., that the octameric form may be retained by the filter, or cause viral filter plugging). For examples, a viral filter with a pore size of 20 nm will retain the octameric form of ASA, but not the dimeric form.

Mixed-Mode Chromatography

The purification methods described herein can include one or more steps of mixed-mode chromatography. Mixed-mode chromatography is a type of chromatography in which several modes of separation are applied to resolve a mixture of different molecules, typically in liquid chromatography. For example, a mixed-mode separation can include combinational phases with ion-exchange and reversed phase characteristics at the same time. These stationary phases with more than one interaction type are available from several column manufacturers.

In one aspect, the disclosure features a method of purifying arylsulfatase A from a sample, where the method includes, for example, providing a sample of arylsulfatase A (e.g., recombinant arylsulfatase A), and subjecting the sample of arylsulfatase A to mixed mode chromatography, e.g., mixed mode chromatography described herein, such as a method including ceramic hydroxyapatite (HA) chromatography, e.g., hydroxyapatite type I or type II chromatography. In some embodiments, the mixed mode chromatography is performed using one or more of: CHT™ Ceramic Hydroxyapatite Type I Media, CHT™ Ceramic Hydroxyapatite Type II Media, BIO-GEL® HT Hydroxyapatite, and BIO-GEL® HTP Hydroxyapatite.

In some embodiments, subjecting the sample of arylsulfatase A to mixed mode chromatography includes: loading the sample of arylsulfatase A onto a mixed mode chromatography column (e.g., HA chromatography), washing the mixed mode chromatography column, and eluting the arylsulfatase A from the column. In some embodiments, subjecting the sample of arylsulfatase A to the mixed mode exchange chromatography is performed at a temperature about 23° C. or less, about 18° C. or less, or about 16° C. or less, e.g., about 23° C., about 20° C., about 18° C., or about 16° C.

In some embodiments, loading the sample of arylsulfatase A onto the mixed mode chromatography column is performed with a loading buffer. In one embodiment, the loading buffer contains sodium phosphate. For example, the sodium phosphate concentration of the loading buffer is from about 1 mM to about 10 mM, e.g., from about 1 mM to about 5 mM, from about 5 mM to about 10 mM, e.g., about 1 mM, about 2 mM, or about 5 mM. In another embodiment, the loading buffer contains sodium chloride. For example, the sodium chloride concentration of the loading buffer is from about 100 mM to about 400 mM, e.g., from about 200 to about 300 mM, e.g., about 220 mM, about 240 mM, about 260 mM, or about 280 mM.

In some embodiments, loading the sample of arylsulfatase A onto the mixed mode chromatography column is performed at a pH from about 5 to about 9, e.g., from about 6 to about 8, e.g., about 7.

In some embodiments, the mixed-mode chromatography includes ceramic hydroxyapatite (HA) chromatography. Hydroxyapatite (HAP) usually refers to the crystalline form of calcium phosphate. The mechanism of HAP involves non-specific interactions between negatively charged protein carboxyl groups and positively charged calcium ions on the resin, and positively charged protein amino groups and negatively charged phosphate ions on the resin. Basic or acidic proteins can be adsorbed selectively onto the column by adjusting the buffer's pH; elution can be achieved by varying the buffer's salt concentration. Again, it is evident that numerous buffer compositions as well as combinations of buffers can be employed. Typically, however, the column can be equilibrated with 1-10 column washes of a buffer comprising 0.001 M $NaPO_4$, 0.02 M MES-Tris, 0.26 M NaCl, pH 7.0. As of convenience the sample can be loaded in the buffer from the previous step of the purification process, or the sample can be loaded using a loading buffer. The column can be washed with 1-10 column volumes of the buffer used for equilibration, followed by a washing buffer comprising 0.005 M $NaPO_4$, 0.02 M MES-Tris, 0.26 M NaCl, pH 7.0. Alternatively, the column can be equilibrated, loaded, and washed with any other equilibration, loading, and washing buffers described herein for mixed mode chromatography. The sample can be eluted in a buffer comprising 0.04 M $NaPO_4$, pH 7.0. Optionally, the column can be stripped by washing with 1-10 column volumes of 0.4 M $NaPO_4$, pH 12. Alternatively, the sample can be eluted in any other elution buffer described herein for mixed mode chromatography.

In some embodiments, washing the mixed mode chromatography column is performed with one or more washing buffers. For example, washing the mixed mode chromatography column can include two or more (e.g., a first and a second) washing steps, each using a different washing buffer.

In one embodiment, the washing buffer contains sodium phosphate. For example, the sodium phosphate concentration of the washing buffer is from about 1 mM to about 10 mM, e.g., from about 1 mM to about 5 mM, from about 5 mM to about 10 mM, e.g., about 1 mM, about 5 mM, or about 10 mM. In another embodiment, the washing buffer contains sodium chloride. For example, the sodium chloride concentration of the washing buffer is from about 50 mM to about 600 mM, e.g., from about 100 mM to about 500 mM, or from about 200 to about 400 mM, e.g., about 220 mM, about 240 mM, about 260 mM, or about 280 mM.

In some embodiments, washing the mixed mode chromatography column is performed at a pH from about 5 to about 9, e.g., from about 6 to about 8, e.g., about 7.

In some embodiments, eluting the arylsulfatase A from the mixed mode chromatography column is performed at a pH from about 5 to about 9, e.g., from about 6 to about 8, e.g., about 7. In some embodiments, eluting the arylsulfatase A from the mixed mode chromatography column includes one or more steps of elution peak collection. For example, the elution peak collection starts from about 50 mAU at the ascending side to about 50 mAU at the descending side, e.g., from about 100 mAU at the ascending side to about 50 mAU at the descending side, from about 200 mAU at the ascending side to about 50 mAU at the descending side, from about 50 mAU at the ascending side to about 100 mAU at the descending side, from about 50 mAU at the ascending side to about 200 mAU at the descending side, or from about 100 mAU at the ascending side to about 100 mAU at the descending side, e.g., as determined by spectrophotometry, e.g., at 280 nM.

The loading buffer, washing buffer, and elution buffer described herein can include one or more buffering agents. For example, the buffering agent can be TRIS, HEPES, MOPS, PIPES, SSC, MES, sodium phosphate, sodium acetate, or a combination thereof. The concentration of the buffering agent is between about 1 mM and about 500 mM, e.g., between about 10 mM and about 250 mM, between about 20 mM and about 100 mM, between about 1 mM and 5 mM, between about 5 mM and 10 mM, between about 10 mM and 50 mM, or between about 50 mM and about 100 mM, e.g., about 1 mM, about 5 mM, about 10 mM, about 20 mM, about 30 mM, about 40 mM, or about 50 mM.

In some embodiments, the purification of ASA by mixed mode chromatography succeeds the purification by ion-exchange chromatography (e.g., anion exchange chromatography). It is contemplated, however, that these steps could be performed in the reverse order.

Yield following mixed mode chromatography may vary. In some embodiments, the arylsulfatase A activity yield is at least about 80%, e.g., at least about 90%, e.g., between about 80% and about 115%. In some embodiments, the protein yield (AU or Absorbance Units) is from about 30% to 80%, e.g., from about 35% to about 75%, or from about 50% to about 70%, e.g., as determined by spectrophotometry, e.g., at 280 nm.

Purity following mixed mode chromatography is greatly improved. In some embodiments, the specific activity of the purified arylsulfatase A is at least from about 50 U/mg to about 140 U/mg, e.g., at least about 70 U/mg, at least about 90 U/mg, at least about 100 U/mg, or at least about 120 U/mg, e.g., as determined by a method described herein. In some embodiment, the arylsulfatase A is purified to at least about 95%, at least about 98%, at least about 99%, at least about 99.5%, at least about 99.6%, at least about 99.7%, at least about 99.8%, or at least about 99.9%. The purity of arylsulfatase A can be measured by, e.g., one or more of: host cell protein (HCP) Western blot, SDS-PAGE Coomassie staining, SDS-PAGE silver staining, reverse phase HPLC, and size exclusion HPLC. In some embodiments, the host cell protein (HCP) log reduction value (LRV) is between about 0.3 and about 0.6, e.g., between about 0.4 and 0.5.

Hydrophobic Interaction Chromatography (HIC)

The purification methods described herein can include subjecting the sample of arylsulfatase A to hydrophobic interaction chromatography (HIC). In one embodiment, the hydrophobic interaction chromatography includes phenyl chromatography. In other embodiments, the hydrophobic interaction chromatography includes butyl chromatography or octyl chromatography. In some embodiments, subjecting the sample of arylsulfatase A to HIC is performed at a temperature about 23° C. or less, about 18° C. or less, or about 16° C. or less, e.g., about 23° C., about 20° C., about 18° C., or about 16° C. In some embodiments, the sample of arylsulfatase A is subjected to mixed mode chromatography prior to HIC.

Hydrophobic interaction chromatography utilizes the attraction of a given molecule for a polar or non-polar environment, and in terms of protein, this propensity is governed by the hydrophobicity or hydrophilicity of residues on the exposed, outer surface of a protein. Thus, proteins are fractionated based upon their varying degrees of attraction to a hydrophobic matrix, typically an inert support with alkyl linker arms of 2-18 carbons in chain length. The stationary phase consists of small non-polar groups (butyl, octyl, or phenyl) attached to a hydrophilic polymer backbone (e.g., cross-linked Sepharose™, dextran, or agarose). Thus, the HIC column is typically a butyl SEPHAROSE™ column or a phenyl SEPHAROSE™ column, most typically a phenyl SEPHAROSE™ column. In some embodiments, the hydrophobic interaction chromatography includes phenyl chromatography using one or more of Phenyl SEPHAROSE™ High Performance, Phenyl SEPHAROSE™ 6 Fast Flow (low sub), or Phenyl SEPHAROSE™ 6 Fast Flow (high sub).

In some embodiments, subjecting the sample of arylsulfatase A to hydrophobic interaction chromatography includes: loading the sample of arylsulfatase A onto a HIC column, washing the HIC column, and eluting the arylsulfatase A from the column. Loading, washing and elution in HIC basically follow the same principle as described above for the ion-exchange chromatography, but often nearly opposite conditions to those used in ion exchange chromatography are applied. Thus, the HIC process involves the use of a high salt loading buffer, which unravels the protein to expose hydrophobic sites. The protein is retained by the hydrophobic ligands on the column, and is exposed to a gradient of buffers containing decreasing salt concentrations. As the salt concentration decreases, the protein returns to its native conformation and eventually elutes from the column. Alternatively proteins may be eluted with PEG.

In some embodiments, loading the sample of arylsulfatase A onto the HIC column is performed with a loading buffer. In one embodiment, the loading buffer contains sodium chloride. For example, the sodium chloride concentration of the loading buffer is from about 0.5 M to about 2.5 M, e.g., about 1 M or about 1.5 M. In another embodiment, the loading buffer contains sodium phosphate. For example, the sodium phosphate concentration of the loading buffer is from about 10 mM to about 100 mM, e.g., about 25 mM, about 50 mM, or about 75 mM. In some embodiments, loading the sample of arylsulfatase A onto the HIC column is performed at a pH from about 5 to about 7, e.g., from about 5.5 to about 6.5, e.g., about 5.5, about 6.0, or about 6.5. In some embodiments, the sample of arylsulfatase A is loaded onto the HIC column at a binding capacity about 12 AU/L resin or less, e.g., about 10 AU/L resin or less, about 9 AU/L resin or less, about 7 AU/L resin or less, or about 5 AU/L resin or less, e.g., between about 5 AU/L resin and about 9 AU/L resin, or between about 5 AU/L resin and about 7 AU/L resin.

The use of phenyl SEPHAROSE™ as solid phase in the HIC is typical in the present disclosure. Again, it is readily apparent that, when it comes to the exact conditions as well as the buffers and combinations of buffers used for the loading, washing and elution processes, a large number of different possibilities exist. In a typical embodiment, the column can be equilibrated in a buffer which contains 0.05 M $NaPO_4$, 1 M NaCl, pH 5.5. As of convenience the sample can be loaded in the buffer from the previous step of the purification process, or the sample can be loaded using a loading buffer.

In some embodiments, washing the HIC column is performed with one or more washing buffers. For example, washing the HIC column can include two or more (e.g., a first and a second) washing steps, each using a different washing buffer. In some embodiments, the washing buffer contains sodium chloride. For example, the sodium chloride concentration of the washing buffer is from about 100 mM to about 1.5 M, e.g., from about 250 mM to about 1 M, e.g., about 250 mM, about 500 mM, about 750 mM, or about 1 M. In another embodiment, the washing buffer contains sodium phosphate. For example, the sodium phosphate concentration of the loading buffer is from about 10 mM to about 100 mM, e.g., about 25 mM, about 50 mM, or about 75 mM. In some embodiments, washing the HIC column is performed at a pH from about 5 to about 7, e.g., from about 5.5 to about 6.5, e.g., about 5.5, about 6.0, or about 6.5. For example, washing can be performed using 1-2 column washes of equilibration buffer followed by 1-5 column volumes of 0.02 M MES, 0.05 M $NaPO_4$, 0.5 M NaCl, pH 5.5. Alternatively, the column can be equilibrated, loaded, and washed with any other equilibration, loading, and washing buffers described herein for HIC.

In some embodiments, eluting the arylsulfatase A from the HIC column is performed with an elution buffer. In some embodiments, the elution buffer contains sodium chloride. For example, the sodium chloride concentration of the elution buffer is from about 30 mM to about 100 mM, e.g., from about 45 mM to about 85 mM, e.g., about 50 mM, about 60 mM, about 70 mM, or about 80 mM. In some embodiments, eluting the arylsulfatase A from the HIC column is performed at a pH from about 5 to about 9, e.g., from about 6 to about 8, e.g., about 7. For example, arylsulfatase A can be eluted using 0.02 M MES-Tris, 0.06 M NaCl, pH 7.0. Alternatively, the sample can be eluted in any other elution buffer described herein for HIC.

In some embodiments, eluting the arylsulfatase A from the HIC column includes one or more steps of elution peak collection. For example, the elution peak collection starts from about 50 mAU at the ascending side to about 50 mAU at the descending side, e.g., from about 100 mAU at the ascending side to about 50 mAU at the descending side, from about 200 mAU at the ascending side to about 50 mAU at the descending side, from about 50 mAU at the ascending side to about 100 mAU at the descending side, from about 50 mAU at the ascending side to about 200 mAU at the descending side, or from about 100 mAU at the ascending side to about 100 mAU at the descending side, e.g., as determined by spectrophotometry, e.g., at 280 nM.

In some embodiments, the purification of arylsulfatase A by HIC succeeds the purification by ion-exchange chromatography (e.g., anion exchange chromatography) and/or mixed mode chromatography. It is contemplated, however, that these steps could be performed in the reverse order.

The loading buffer, washing buffer, and elution buffer described herein can include one or more buffering agents. For example, the buffering agent can be TRIS, HEPES, MOPS, PIPES, SSC, MES, sodium phosphate, sodium acetate, or a combination thereof. The concentration of the buffering agent is between about 1 mM and about 500 mM, e.g., between about 10 mM and about 250 mM, between about 20 mM and about 100 mM, between about 1 mM and 5 mM, between about 5 mM and 10 mM, between about 10 mM and 50 mM, or between about 50 mM and about 100 mM, e.g., about 1 mM, about 5 mM, about 10 mM, about 20 mM, about 30 mM, about 40 mM, or about 50 mM.

Yield following HIC may vary. In some embodiments, the arylsulfatase A activity yield is at least about 60%, e.g., at least about 70%, e.g., between about 70% and about 100%. In some embodiments, the protein yield (AU or Absorbance Units) is from about 45% to 100%, e.g., from about 50% to about 95%, or from about 55% to about 90%, e.g., as determined by spectrophotometry, e.g., at 280 nm.

Purity following HIC is greatly improved. In some embodiments, the specific activity of the purified arylsulfatase A is at least from about 50 U/mg to about 140 U/mg, e.g., at least about 70 U/mg, at least about 90 U/mg, at least about 100 U/mg, or at least about 120 U/mg, e.g., as determined by a method described herein.

In some embodiments, the arylsulfatase A is purified to at least about 95%, at least about 98%, at least about 99%, at least about 99.5%, at least about 99.6%, at least about 99.7%, at least about 99.8%, or at least about 99.9%. The purity of arylsulfatase A can be measured by, e.g., one or more of: host cell protein (HCP) Western blot, SDS-PAGE Coomassie staining, SDS-PAGE silver staining, reverse phase HPLC, and size exclusion HPLC. In some embodiments, the host cell protein (HCP) log reduction value (LRV) is between about 0.6 and about 1.2, e.g., between about 0.7 and 0.95.

Ultrafiltration/Diafiltration

The purification methods described herein can include one or more steps of downstream ultrafiltration and/or diafiltration. In some embodiments, the method further comprises concentrating and/or filtering the sample of arylsulfatase A, e.g., by ultrafiltration and/or diafiltration, e.g., by tangential flow ultrafiltration.

Ultrafiltration refers to a membrane separation process, driven by a pressure gradient, in which the membrane fractionates components of a liquid as a function of their solvated size and structure. Diafiltration is a specialized type of ultrafiltration process in which the retentate is diluted with water and re-ultrafiltered, to reduce the concentration of soluble permeate components and increase further the concentration of retained components. Ultrafiltration is often combined with diafiltration into ultrafiltration/diafiltration (UFDF) purification steps.

Embodiments of the invention utilize at least one, at least two, at least three or more downstream UFDF purification steps. One or more diafiltrations may occur within UFDF step (e.g., UFDFDF). In some embodiments, the protein yield (AU or Absorbance Units) following downstream UFDF, relative the amount from the preceding purification step, is from about 90% to 105%, e.g., from about 95% to about 100%, e.g., from about 97% to about 99%, as determined by spectrophotometry, e.g., at 280 nm. In some embodiments, essentially no protein is lost during UFDF.

In some embodiments of the invention, downstream UFDF results in rASA that is at least about 95%, at least about 97%, at least about 98%, at least about 99% or more pure, as determined by size exclusion chromatography-high performance liquid chromatography (SEC-HPLC) and/or reverse phase-high performance liquid chromatography (RP-HPLC). In some embodiment, the arylsulfatase A is purified to at least about 95%, at least about 98%, at least about 99%, at least about 99.5%, at least about 99.6%, at least about 99.7%, at least about 99.8%, or at least about 99.9%. The purity of arylsulfatase A can be measured by, e.g., one or more of: host cell protein (HCP) Western blot, SDS-PAGE Coomassie staining, SDS-PAGE silver staining, reverse phase HPLC, and size exclusion HPLC. The specific activity of the rASA is at least from about 60 U/mg to about 100 U/mg, e.g., at least about 65 U/mg, at least about 90 U/mg, at least about 70 U/mg, or at least about 90 U/mg, e.g., as determined by a sulfatase release assay, as described below.

In some embodiments, arylsulfatase A is purified by separation from contaminants according to their size in an acidic environment by tangential flow filtration. Arylsulfatase A forms an octamer at low pH with a theoretical molecular weight of 480 kDa and will therefore be retained by a relatively open membrane while most of the contaminants will pass this membrane (Sommerlade et al., (1994) *Biochem. J.,* 297; 123-130; Schmidt et al., (1995) *Cell,* 82 271-278; Lukatela et al., (1998) *Biochemistry,* 37, 3654-3664).

In a typical embodiment, the diafiltration buffer comprises 0.01 M sodium phosphate-citrate, 0.137 M NaCl, pH 6.0.

In some embodiments, as the starting material for this process is a suspension of arylsulfatase A as eluted from the chromatography column in the previous step of the process, the pH in this suspension is adjusted to 4-5 by addition of 0.2-1 M Na-acetate pH 4.5. Diafiltration is then performed against 1-10 buffer volumes of Na-acetate pH 4.0-5.5 in a manner well known to somebody skilled in the art. The filtration can be performed with the application of several different filter types with nominal weight cut-off values ranging from 20-450 kDa, however it is typical to use a filter with a cut-off value ranging from 100-300 kDa. For further processing of the arylsulfatase A containing solution the pH is adjusted to a value within the range between 7 and 8 by addition of Tris-base to a final concentration of approximately 20-50 mM.

As an alternative to the acidic tangential flow filtration as described above, separation of ASA from the contaminants can be obtained with acidic gel filtration using essentially the same conditions and compositions of buffers. The filtration is performed at low pH through a gel filtration column, which has been equilibrated with a solution at low pH, for example, a 0.2-0.9 M solution of Na-acetate at pH 4-5. As an option, the solution of arylsulfatase A can be concentrated by tangential flow filtration through a 20-50 kDa filter prior to the gel filtration. The extent of concentration may vary considerably so that arylsulfatase A may be concentrated from about 0.1 mg/ml to about 50 mg/ml, preferably to about 5 mg/ml.

In some embodiments, the sample pool is concentrated against a Biomax A-screen, 30 kDa. Diafiltration is performed against 3-5 column washes of 20 mM Na-acetate, pH 5.4-5.7.

Characterization of Purified ASA Proteins

Purified recombinant ASA protein may be characterized using various methods.

Purity

The purity of purified recombinant ASA protein is typically measure by the level of various impurities (e.g., host cell protein or host cell DNA) present in the final product. For example, the level of host cell protein (HCP) may be measured by ELISA or SDS-PAGE. In some embodiments, the purified recombinant ASA protein contains less than 150 ng HCP/mg ASA protein (e.g., less than 140, 130, 120, 110, 100, 90, 80, 70, 60, 50, 40, 30, 30, 20, 10 ng HCP/mg ASA protein). In some embodiments, the purified recombinant ASA protein contains less than about 150 pg/mg, 140 pg/mg, 130 pg/mg, 120 pg/mg, 110 pg/mg, 100 pg/mg, 90 pg/mg, 80 pg/mg, 70 pg/mg, 60 pg/mg, 50 pg/mg, 40 pg/mg, 30 pg/mg, 20 pg/mg, or 10 pg/mg Host Cell DNA.

In some embodiments, the purified recombinant ASA protein, when subject to SDS-PAGE with Coomassie Brilliant Blue staining, has no new bands with intensity greater than the 0.05%, 0.01%, 0.15%, 0.2%, 0.25%, 0.3%, 0.35%, 0.4%, 0.45%, or 0.5% assay control. In some embodiments, the purified recombinant ASA protein, when subject to SDS-PAGE with Western blotting against HCP, has no bands with intensity greater than the 15 kDa HCP band assay control, and no new bands with intensity greater than the 0.05%, 0.01%, 0.15%, 0.2%, 0.25%, 0.3%, 0.35%, 0.4%, 0.45%, 0.5%, or 1.0% assay control. In some embodiments, the purified recombinant ASA protein, when subject to SDS-PAGE with silver staining, has no new bands with intensity greater than the 0.05%, 0.01%, 0.15%, 0.2%, 0.25%, 0.3%, 0.35%, 0.4%, 0.45%, or 0.5% assay control. In some embodiments, the host cell protein (HCP) log reduction value (LRV) is between about 0.3 and about 0.6, e.g., between about 0.4 and 0.5. Various assay controls may be used, in particular, those acceptable to regulatory agencies such as FDA.

The purity of purified recombinant ASA protein may also be determined by one or more of size exclusion chromatography-high performance liquid chromatography (SEC-HPLC), capillary electrophoresis-SDS PAGE (CE-SDS PAGE), and/or reverse phase-high performance liquid chromatography (RP-HPLC) (e.g., using columns of octadecyl (C18)-bonded silica, and carried out at an acidic pH with TFA as a counter-ion). In some embodiments of the invention, the major peak in the chromatogram is ASA. Parameters that may be altered or optimized to increase resolution include gradient conditions, organic modifier, counter ion, temperature, column pore size and particle size, solvent composition and flow rate. Purity levels may be discerned by main peak percentage, as known to those of skill in the art. For example, purity may be determined by integrating the main and side peaks observed and calculating the main peak's percentage of the total area. In some embodiments of the invention, the purity of ASA purified by the methods disclosed herein and as determined by the main peak percentage of SEC-HPLC is greater than or equal to 95% (e.g., about 96%, about 97%, about 98%, about 99% or higher). In some embodiments of the invention, the purity of ASA purified by the methods disclosed herein and as determined by main peak percentage of RP-HPLC is greater than or equal to 98% (i.e., about 98%, about 99% or higher).

Specific Activity

Purified recombinant ASA protein may also be characterized by evaluating functional and/or biological activity. The enzyme activity of a recombinant ASA composition may be determined using methods known in the art. Typically the methods involve detecting the removal of sulfate from a synthetic substrate, which is known as sulphate release assay. One example of an enzyme activity assay involves the use of ion chromatography. This method quantifies the amount of sulfate ions that are enzymatically released by recombinant ASA from a substrate. The substrate may be a natural substrate or a synthetic substrate. In some cases, the substrate is heparin sulfate, dermatan sulfate, or a functional equivalent thereof. Typically, the released sulfate ion is analyzed by ion chromatography with a conductivity detector. In this example, the results may be expressed as U/mg of protein where 1 Unit is defined as the quantity of enzyme required to release 1 μmole sulfate ion per hour from the substrate. In some embodiments, the purified recombinant ASA has a specific activity of at least about 50 U/mg, 60 U/mg, 70 U/mg, 80 U/mg, 90 U/mg, 100 U/mg, 110 U/mg, 120 U/mg, 130 U/mg, 140 U/mg. In some embodiments, the purified recombinant ASA has a specific activity ranging from about 50-200 U/mg (e.g., about 50-190 U/mg, 50-180 U/mg, 50-170 U/mg, 50-160 U/mg, 50-150 U/mg, 50-140 U/mg, 50-130 U/mg, 50-120 U/mg, 50-110 U/mg, 50-100 U/mg, 60-200 U/mg, 60-190 U/mg, 60-180 U/mg, 60-170 U/mg, 60-160 U/mg, 60-150 U/mg, 60-140 U/mg, 60-130 U/mg, 60-120 U/mg, 60-110 U/mg, 60-100 U/mg, 70-200 U/mg, 70-190 U/mg, 70-180 U/mg, 70-170 U/mg, 70-160 U/mg, 70-150 U/mg, 70-140 U/mg, 70-130 U/mg, 70-120 U/mg, 70-110 U/mg, 70-100 U/mg, 80-200 U/mg, 80-190 U/mg, 80-180 U/mg, 80-170 U/mg, 80-160 U/mg, 80-150 U/mg, 80-140 U/mg, 80-130 U/mg, 80-120 U/mg, 80-110 U/mg, 80-100 U/mg, 90-200 U/mg, 90-190 U/mg, 90-180 U/mg, 90-170 U/mg, 90-160 U/mg, 90-150 U/mg, 90-140 U/mg, 90-130 U/mg, 90-120 U/mg, 90-110 U/mg, 90-100 U/mg, 100-200 U/mg, 100-190 U/mg, 100-180 U/mg, 100-170 U/mg, 100-160 U/mg, 100-150 U/mg, 100-140 U/mg, 100-130 U/mg, 100-120 U/mg, 100-110 U/mg, 110-200 U/mg, 110-190 U/mg, 110-180 U/mg, 110-170 U/mg, 110-160 U/mg, 110-150 U/mg, 110-140 U/mg, 110-130 U/mg, 110-120 U/mg, 120-200 U/mg, 120-190 U/mg, 120-180 U/mg, 120-170 U/mg, 120-160 U/mg, 120-150 U/mg, 120-140 U/mg, 120-130 U/mg, 130-200 U/mg, 130-190 U/mg, 130-180 U/mg, 130-170 U/mg, 130-160 U/mg, 130-150 U/mg, or 130-140 U/mg).

In another example, enzyme activity of a recombinant ASA composition may be determined by measuring the removal of sulfate from a 4-methylumbelliferyl-sulfate (4-MUF-sulfate) substrate to form the fluorescent methylumbelliferone. In this example, the fluorescence signal generated by a test sample can be used to calculate enzyme activity (in mU/mL) using a standard of 4-MUF. One milliunit of activity is defined as the quantity of enzyme required to convert 1 nanomole of 4-MUF-sulfate to 4-MUF in 1 minute at 37° C. Specific activity may then calculated by dividing the enzyme activity by the protein concentration.

In some embodiments, activity is determined by hydrolysis of the synthetic, chromogenic substrate, para-Nitrocatechol sulphate (pNCS) which has an end product, para-Nitrocatechol (pNC) that absorbs light at 515 nm. The following equation may be used to calculate the enzyme activity in μmol pNCS hydrolyzed/min×ml (=Units/ml):

$$\frac{V tot \,(\mathrm{ml})}{\varepsilon M/1000 \times V\mathrm{sample\,(ml)} \times \mathrm{Incubation\,time\,(min)}} \times \Delta A = \mathrm{Units/ml} \qquad (1)$$

where:

ΔA=absorbance of sample−absorbance of blank

Vtot (ml)=total reaction volume in ml (in this case 0.15 ml)

Vsample (ml)=added sample volume in ml (in this case 0.05 ml)

εM=the molar extinction coefficient for the product pNC, which in this case is 12 400 M-1 cm-1.

Equation 1 can be simplified as:

$$\Delta A \times (0.15/(12\,400/1000 \times 0.05 \times 30)) = X\,\mathrm{\mu mol/(minute \times ml)(=Units/ml)} \qquad (1)$$

To calculate the specific activity in μmol pNC consumed/(minute×mg) (=Units/mg), equation 1 is divided by the protein concentration of the sample:

$$\mathrm{Eq.\,1/Protein\,conc.\,(mg/ml)} = Y\,\mathrm{mmol/(minute \times mg) = Units/mg} \qquad (2)$$

In any example, the protein concentration of a recombinant ASA composition may be determined by any suitable method known in the art for determining protein concentrations. In some cases, the protein concentration is determined by an ultraviolet light absorbance assay. Such absorbance assays are typically conducted at about a 280 nm wavelength (A280).

In some embodiments, purified recombinant ASA has a specific activity on a 4-methylumbelliferone substrate in a range of about $1.0\times10^3$ mU/mg to $100.0\times10^3$ mU/mg, about $1.0\times10^3$ mU/mg to $50.0\times10^3$ mU/mg, about $1.0\times10^3$ mU/mg to $40.0\times10^3$ mU/mg, about $1.0\times10^3$ mU/mg to $30.0\times10^3$ mU/mg, about $1.0\times10^3$ mU/mg to $20.0\times10^3$ mU/mg, about $1.0\times10^3$ mU/mg to $10.0\times10^3$ mU/mg, about $4.0\times10^3$ mU/mg to $8.0\times10^3$ mU/mg, about $4.0\times10^3$ mU/mg to $10.0\times10^3$ mU/mg, about $4.5\times10^3$ mU/mg to $10.0\times10^3$ mU/mg, about $5.0\times10^3$ mU/mg to $10.0\times10^3$ mU/mg, about $5.5\times10^3$ mU/mg to $15.0\times10^3$ mU/mg, or about $4.0\times10^3$ mU/mg to $20.0\times10^3$ mU/mg. In some embodiments, purified recombinant ASA has a specific activity on a 4-methylumbelliferone substrate of about $1.0\times10^3$ mU/mg, about $2.0\times10^3$ mU/mg, about $3.0\times10^3$ mU/mg, about $4.0\times10^3$ mU/mg, about $5.0\times10^3$ mU/mg, about $10.0\times10^3$ mU/mg, about $15.0\times10^3$ mU/mg, about $20.0\times10^3$ mU/mg, about $25.0\times10^3$ mU/mg, about $30.0\times10^3$ mU/mg, about $35.0\times10^3$ mU/mg, about $40.0\times10^3$ mU/mg, about $45.0\times10^3$ mU/mg, about $50.0\times10^3$ mU/mg, or more.

Charge Profile

Purified recombinant ASA may be characterized by the charge profile associated with the protein. Typically, protein charge profile reflects the pattern of residue side chain charges, typically present on the surface of the protein. Charge profile may be determined by performing an ion exchange (IEX) chromatography (e.g., HPLC) assay on the protein. In some embodiments, a "charge profile" refers to a set of values representing the amount of protein that elutes from an ion exchange column at a point in time after addition to the column of a mobile phase containing an exchange ion.

Typically, a suitable ion exchange column is an anion exchange column. For example, a charge profile may be determined by strong anion exchange (SAX) chromatography using a high performance liquid chromatography (HPLC) system. In general, recombinant ASA adsorbs onto the fixed positive charge of a strong anion exchange column and a gradient of increasing ionic strength using a mobile phase at a predetermined flow rate elutes recombinant ASA species from the column in proportion to the strength of their ionic interaction with the positively charged column. More negatively charged (more acidic) ASA species elute later than less negatively charged (less acid) ASA species. The concentration of proteins in the eluate are detected by ultraviolet light absorbance (at 280 nm).

In some embodiments, recombinant ASA adsorbs at about pH 8.0 in 20 mM TRIS-HCl onto the fixed positive charge of a Mini Q PE column and a gradient of increasing ionic strength using a mobile phase consisting of 20 mM TRIS-HCL, 1 M sodium chloride, pH 8.0 at a flow rate of 0.8 ml/min elutes recombinant ASA species from the column in proportion to the strength of their ionic interaction with the positively charged column.

In some embodiments, a charge profile may be depicted by a chromatogram of absorbance units versus time after elution from the HPLC column. The chromatogram may comprise a set of one or more peaks, with each peak in the set identifying a subpopulation of recombinant ASAs of the composition that have similar surface charges.

Glycan Mapping

In some embodiments, a purified recombinant ASA protein may be characterized by its proteoglycan composition, typically referred to as glycan mapping. Without wishing to be bound by any theory, it is thought that glycan linkage along with the shape and complexity of the branch structure may impact in vivo clearance, lysosomal targeting, bioavailability, and/or efficacy.

Typically, a glycan map may be determined by enzymatic digestion and subsequent chromatographic analysis. Various enzymes may be used for enzymatic digestion including, but not limited to, suitable glycosylases, peptidases (e.g., endopeptidases, exopeptidases), proteases, and phosphatases. In some embodiments, a suitable enzyme is alkaline phosphatase. In some embodiments, a suitable enzyme is neuraminidase. Glycans (e.g., phosphoglycans) may be detected by chromatographic analysis. For example, phosphoglycans may be detected by High Performance Anion Exchange Chromatography with Pulsed Amperometric Detection (HPAE-PAD) or size exclusion High Performance Liquid Chromatography (HPLC). The quantity of glycan (e.g., phosphoglycan) represented by each peak on a glycan map may be calculated using a standard curve of glycan (e.g., phosphoglycan), according to methods known in the art and disclosed herein.

In some embodiments, a purified recombinant ASA protein according to the present invention is characterized with a glycan map comprising at least seven peak groups indicative of neutral (peak group 1), mono-sialylated (peak group 2), capped mannose-6-phosphated (peak group 3), di-sialylated (peak group 4), mono-mannose-6-phosphated (peak group 5), hybrid (peak group 6), and di-mannose-6-phosphated (peak group 7) ASA protein, respectively.

Peptide Mapping

In some embodiments, peptide mapping may be used to characterize amino acid composition, post-translational modifications, and/or cellular processing; such as cleavage of a signal peptide, and/or glycosylation. Typically, a recombinant protein may be broken into discrete peptide fragments, either through controlled or random breakage, to produce a pattern or peptide map. In some cases, a purified ASA protein may be first subjected to enzymatic digest prior to analytic analysis. Digestion may be performed using a peptidase, glycoside hydrolase, phosphatase, lipase or protease and/or combinations thereof, prior to analytic analysis. The structural composition of peptides may be determined using methods well known in the art. Exemplary methods include, but are not limited to, Mass spectrometry, Nuclear Magnetic Resonance (NMR) or HPLC.

Metals Analysis

In some embodiments, a purified recombinant ASA protein may be characterized by metals analysis. Various methods of analyzing trace metals in purified drug substances are known in the art and can be used to practice the present invention.

In some embodiments, residual phosphorous is measured and compared to a reference sample. Without wishing to be bound by any particular theory, it is hypothesized that residual phosphorus contributes to maintaining drug substance pH. In some embodiments of the invention, residual phosphorous is between about 10-50 ppm (i.e., between about 10-45 ppm, about 10-40 ppm, about 10-30 ppm, about 20-50 ppm about 20-45 ppm, about 20-40 ppm, about 20-30 ppm, about 30-50 ppm, about 30-40 ppm). In some embodiments, the pH range of recombinant ASA purified according to the methods disclosed herein is between about 5-7 (i.e., between about 5.5-7.0, about 5.5-6.5, about 5.5-6.0, about 6.0-7.0, about 6.0-6.5, about 6.0-6.4, about 6.0-6.3, about 6.0-6.2, about 6.0-6.1, about 6.1-6.2).

In some embodiments, recombinant ASA purified according to the methods disclosed herein contains calcium. Without wishing to be bound by any particular theory, it is hypothesized that calcium ions present in the active site of ASA may be necessary for enzymatic activity. In some embodiments of the invention, calcium is present at levels between about 1-20 ppm (i.e., between about 1-15 ppm, about 1-10 ppm, about 5-15 ppm, about 5-10 ppm, about 10-20 ppm, about 10-15 ppm, about 10-14 ppm, about 10-13 ppm, about 10-12 ppm).

Pharmaceutical Composition and Administration

Purified recombinant ASA protein may be administered to a MLD patient in accordance with known methods. For example, purified recombinant ASA protein may be delivered intravenously, subcutaneously, intramuscularly, parenterally, transdermally, or transmucosally (e.g., orally or nasally)).

In some embodiments, a recombinant ASA or a pharmaceutical composition containing the same is administered to a subject by intravenous administration.

In some embodiments, a recombinant ASA or a pharmaceutical composition containing the same is administered to a subject by intrathecal administration. As used herein, the term "intrathecal administration" or "intrathecal injection" refers to an injection into the spinal canal (intrathecal space surrounding the spinal cord). Various techniques may be used including, without limitation, lateral cerebroventricular injection through a burrhole or cisternal or lumbar puncture or the like. In some embodiments, "intrathecal administration" or "intrathecal delivery" according to the present invention refers to IT administration or delivery via the lumbar area or region, i.e., lumbar IT administration or delivery. As used herein, the term "lumbar region" or "lumbar area" refers to the area between the third and fourth lumbar (lower back) vertebrae and, more inclusively, the L2-S1 region of the spine. In some embodiments, a recombinant ASA or a pharmaceutical composition containing the same is administered to a subject by intrathecal administration as described in PCT international publications WO2011/163648 and WO2011/163650, incorporated herein by reference in their entirety.

In some embodiments, a recombinant ASA or a pharmaceutical composition containing the same is administered to the subject by subcutaneous (i.e., beneath the skin) administration. For such purposes, the formulation may be injected using a syringe. However, other devices for administration of the formulation are available such as injection devices (e.g., the Inject-ease and Genject devices); injector pens (such as the GenPen); needleless devices (e.g., MediJector and BioJector); and subcutaneous patch delivery systems.

In some embodiments, intrathecal administration may be used in conjunction with other routes of administration (e.g., intravenous, subcutaneously, intramuscularly, parenterally, transdermally, or transmucosally (e.g., orally or nasally)).

The present invention contemplates single as well as multiple administrations of a therapeutically effective amount of a recombinant ASA or a pharmaceutical composition containing the same described herein. A recombinant ASA or a pharmaceutical composition containing the same can be administered at regular intervals, depending on the nature, severity and extent of the subject's condition (e.g., a lysosomal storage disease). In some embodiments, a therapeutically effective amount of a recombinant ASA or a pharmaceutical composition containing the same may be administered periodically at regular intervals (e.g., once every year, once every six months, once every five months, once every three months, bimonthly (once every two months), monthly (once every month), biweekly (once every two weeks), weekly, daily or continuously).

A recombinant ASA or a pharmaceutical composition containing the same can be formulated with a physiologically acceptable carrier or excipient to prepare a pharmaceutical composition. The carrier and therapeutic agent can be sterile. The formulation should suit the mode of administration.

Suitable pharmaceutically acceptable carriers include but are not limited to water, salt solutions (e.g., NaCl), saline, buffered saline, alcohols, glycerol, ethanol, gum arabic, vegetable oils, benzyl alcohols, polyethylene glycols, gelatin, carbohydrates such as lactose, amylose or starch, sugars such as mannitol, sucrose, or others, dextrose, magnesium stearate, talc, silicic acid, viscous paraffin, perfume oil, fatty acid esters, hydroxymethylcellulose, polyvinyl pyrolidone, etc., as well as combinations thereof. The pharmaceutical preparations can, if desired, be mixed with auxiliary agents (e.g., lubricants, preservatives, stabilizers, wetting agents, emulsifiers, salts for influencing osmotic pressure, buffers, coloring, flavoring and/or aromatic substances and the like) which do not deleteriously react with the active compounds or interference with their activity. In some embodiments, a water-soluble carrier suitable for intravenous administration is used.

The composition or medicament, if desired, can also contain minor amounts of wetting or emulsifying agents, or pH buffering agents. The composition can be a liquid solution, suspension, emulsion, tablet, pill, capsule, sustained release formulation, or powder. The composition can also be formulated as a suppository, with traditional binders and carriers such as triglycerides. Oral formulation can include standard carriers such as pharmaceutical grades of mannitol, lactose, starch, magnesium stearate, polyvinyl pyrollidone, sodium saccharine, cellulose, magnesium carbonate, etc.

The composition or medicament can be formulated in accordance with the routine procedures as a pharmaceutical composition adapted for administration to human beings. For example, in some embodiments, a composition for intravenous administration typically is a solution in sterile isotonic aqueous buffer. Where necessary, the composition may also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where the composition is to be administered by infusion, it can be dispensed with an infusion bottle containing sterile pharmaceutical grade water, saline or dextrose/water. Where the composition is administered by injection, an ampule of sterile water for injection or saline can be provided so that the ingredients may be mixed prior to administration.

In some embodiments, arylsulfatase A is formulated in an isotonic solution such as 154 mM NaCl, or 0.9% NaCl and 10-50 mM sodium phosphate pH 6.5-8.0 or sodium phosphate, glycine, mannitol or the corresponding potassium salts. In another embodiment, the ASA is formulated in a physiological buffer, such as:
  a) formulation buffer I containing (in mM): $Na_2HPO_4$ (3.50-3.90), $NaH_2PO_4$ (0-0.5), Glycine (25-30), Mannitol (230-270), and water for injection; or b) formulation buffer II containing (in mM): Tris-HCl (10), Glycine (25-30), Mannitol (230-270), and water for injection.

Arylsulfatase A purified by a method herein can be used as a medicament for reducing the sphingolipid 3-O-sulfo-galactosylceramide (galactosyl sulphatide) levels within cells in the peripheral nervous system and/or within the central nervous system in a subject suffering from and/or being diagnosed with Metachromatic Leukodystrophy. The administration of ASA will lead to decreased impairment of motor-learning skills and or to increased nerve motor conduction velocity and/or nerve conduction amplitude. As used herein, the term "therapeutically effective amount" is largely determined based on the total amount of the therapeutic agent contained in the pharmaceutical compositions of the present invention. Generally, a therapeutically effective amount is sufficient to achieve a meaningful benefit to the subject (e.g., treating, modulating, curing, preventing and/or ameliorating the underlying disease or condition). For example, a therapeutically effective amount may be an amount sufficient to achieve a desired therapeutic and/or prophylactic effect, such as an amount sufficient to modulate lysosomal enzyme receptors or their activity to thereby treat such lysosomal storage disease or the symptoms thereof (e.g., a reduction in or elimination of the presence or incidence of "zebra bodies" or cellular vacuolization following the administration of the compositions of the present invention to a subject). Generally, the amount of a therapeutic agent (e.g., a recombinant lysosomal enzyme) administered to a subject in need thereof will depend upon the characteristics of the subject. Such characteristics include the condition, disease severity, general health, age, sex and body weight of the subject. One of ordinary skill in the art will be readily able to determine appropriate dosages depending on these and other related factors. In addition, both objective and subjective assays may optionally be employed to identify optimal dosage ranges.

A therapeutically effective amount is commonly administered in a dosing regimen that may comprise multiple unit doses. For any particular therapeutic protein, a therapeutically effective amount (and/or an appropriate unit dose within an effective dosing regimen) may vary, for example, depending on route of administration, on combination with other pharmaceutical agents. Also, the specific therapeutically effective amount (and/or unit dose) for any particular patient may depend upon a variety of factors including the disorder being treated and the severity of the disorder; the activity of the specific pharmaceutical agent employed; the specific composition employed; the age, body weight, general health, sex and diet of the patient; the time of administration, route of administration, and/or rate of excretion or metabolism of the specific fusion protein employed; the duration of the treatment; and like factors as is well known in the medical arts.

It is to be further understood that for any particular subject, specific dosage regimens should be adjusted over time according to the individual need and the professional judgment of the person administering or supervising the administration of the enzyme replacement therapy and that dosage ranges set forth herein are exemplary only and are not intended to limit the scope or practice of the claimed invention.

EXAMPLES

Example 1. Tangential Flow Ultrafiltration—Capture

This example demonstrates that tangential flow ultrafiltration (also known as crossflow filtration) can be used to capture recombinant ASA protein directly from production bioreactor.

Specifically, unpurified bulk material was captured from a production profusion bioreactor by tangential flow ultrafiltration. Tangential flow filtration was performed in a Sartorius Hydrosart® 30 kD Standard membrane within manufacturer's specifications.

Additional experiments were performed in which tangential flow filtration was performed with a Sartorius HYDROSART® ECO membrane while maintaining the same composition and molecular weight cut-off. The ECO membrane allowed the process to utilize lower crossflow rates.

Figure 3:
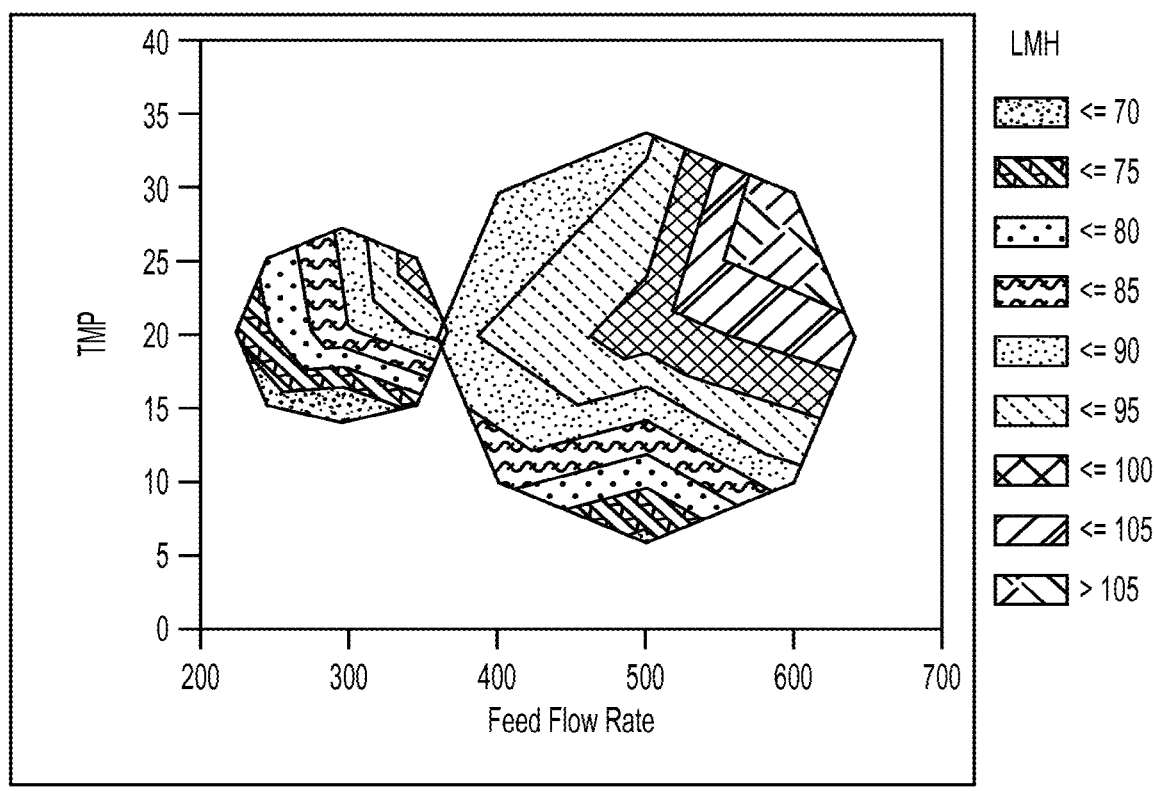
FIG. 3 depicts exemplary results illustrating the correlation between the feed flow rate, transmembrane pressure (TMP) and the permeate flux for each membrane.

The permeate flux values (LMH) yielded from the twelve excursion run conditions performed using the ECO and Standard membranes were analyzed using the contour profiler function. This function showed response contours for two factors at a time. In this study, feed flow rate and transmembrane pressure ("TMP") were compared to the permeate flux for each membrane. Exemplary results are shown in FIG. 3.

As can be seen, a contour plot of the ECO versus Standard membrane excursion runs, the ECO membrane showed a much more robust flux output at the given parameter ranges tested. The ECO membrane was capable of achieving higher flux rates at a lower feed flow rate within the operational range.

More specifically, based on data analysis from design runs, titer Elisa recovery ranges from about 92% to 132%. Host cell protein (HCP) log reduction values range from about 0.11-0.38. Titer ELISA recovery, host cell protein (HCP) log reduction values (LRV) and percent activity recovery were determined as described elsewhere in the application.

The results from this experiment demonstrated the feasibility of implementing a UFDF capture step in the Arylsulfatase A phase III purification process. Based on a side-by-side UFDF excursion run, the ECO membrane was particularly effective because it was capable of achieving higher flux rates at a lower feed flow rate within the operational range. Design experiments were also performed using the ECO membrane in order to evaluate potential impact on operational parameters of load challenge, TMP, feed flow rate, initial concentration factor, and processing temperature on the performance of rhASA capture process. Host Cell Protein (HCP) ELISA and activity step yield were not significantly affected by the operational parameters of the ECO membrane.

Example 2. Depth Filtration and Viral Inactivation

This experiment illustrates the conditions for depth filtration and viral inactivation that may be implemented during the purification process.

For example, the captured unpurified bulk material was thawed at 2-8° C. for ≤120 hrs. Temperature of the bulk material was adjusted to about 18±2° C. and filtered through a Cuno Zeta Plus depth filter followed by polishing filtration. A Sartorious Maxicap Sartopore 2, 0.45±0.2 µm polishing filtration capsule was connected downstream of the depth filter to remove particulates and reduce bioburden in preparation for downstream processing. The filters are flushed with water-for-injection ("WFI") followed by MES-Tris, pH 7.1 equilibration solution.

A final rinse was performed after filtration to recover hold-up material from the filtration train. Once filtration was completed, the filter train was flushed with 0.05 MES-Tris, pH 7.0 rinse solution. Collected rinse was added to the filtered pooled bulk material.

The filtered but unpurified bulk was subsequently processed through a viral inactivation step by addition of Polysorbate 80 and Tri-n-Butyl-Phosphate (TnBP) with about 3-24 hours of subsequent incubation as follows. Polysorbate 80 was added from a 10% (v/v) stock solution in 0.05M MES-Tris, pH 7.1 to the filtered, pooled unpurified bulk to achieve a final concentration of 1%. Tri-n-Butyl-Phosphate (TnBP) was then added to a final concentration of about 0.3% calculated based on the new volume of unpurified bulk containing Polysorbate 80. The resultant pool was mixed to obtain consistency and incubated with continued mixing for about 3-24 hours.

When viral inactivation was complete, the pool was processed through a polyvinylidine difloride (PVDF) 0.2 µm filter before loading onto the first chromatography column. In this experiment, the filtered viral inactivated pool was applied to a Q column (as described below) within about 28 hours of the viral inactivation incubation start time. The viral inactivated intermediate was filtered, and at the end of filtration, the filter was flushed with 0.05M MES-Tris, pH 7.0 buffer to maximize product recovery.

Example 3. Anion Exchange Chromatography

This example illustrates exemplary conditions for anion exchange chromatography, in particular, when the anion exchange chromatography was used as the first chromatography step. In this particular example, Q SEPHAROSE™ Fast Flow (Q FF) resin was utilized in a quarternary amine anion exchange operated in bind and elute modes.

Q FF columns were prepared using standard methods. ASA bound to the Q column at a pH of 7.0 and was eluted with 0.02M MES-Tris, 0.26M NaCl at pH 7.1. The loading, wash and elution were performed at flow rate of about 100. The operating temperature ranges from 16-23° C. The Q elution was collected via absorbance at 280 nm (A280) with set points of 0.5 AU/cm on the ascending side of the peak to 0.25 AU/cm on the descending side of the peak. Exemplary conditions used for anion exchange columns are shown in Table 2.

TABLE 2

Exemplary Conditions Used for Anion Exchange Columns

| Solutions | Use |
| --- | --- |
| 0.5M NaOH | Sanitation |
| 0.02M MES-Tris, 1M NaCl, pH 7.0 | Pre-equilibration and strip |
| 0.05M MES-Tris, pH 7.0 | Equilabration and wash1 |
| 0.02M MES-Tris, 0.12M NaCl, pH 7.1 | Wash 2 |
| 0.02M MES-Tris, 0.26M NaCl, pH 7.1 | Elution and post-use filter chase |
| 0.5M NaOH, 3M NaCl | Clean |
| 0.01M NaOH | Storage |

Additional experiments were conducted to compare exemplary anion exchange resins with respect to purity, activity and throughput (e.g. target loading capacity). In particular, in order to facilitate scale-up, several high capacity anion exchange resins were screened and evaluated in this study.

Once "packed", the resin was equilibrated, loaded, washed and eluted using the conditions shown in Table 3. In this study, binding conditions were kept the same as the Q FF process described above. Fractions of flow through (FT), wash (W) and elution/strip (EL/strip) were collected and analyzed using A280 absorbance, titer assay and SDS-PAGE (Coomassie and Silver stain).

TABLE 3

Exemplary Conditions

| Step | Buffer or material |
| --- | --- |
| Equilibration | 50 mM MES-Tris, pH7.0 |
| Load | Atlas GMP-1 H19/20 UPB |
| Wash | 50 mM MES-Tris, pH7.0 |
| Elute/strip | 50 mM MES-Tris, 1M NaCl, 7.0 |

Seven resins in addition to Q FF were evaluated to determine binding capacity, selectivity, and recovery. Overall yield was comparable for all of the resins ranging from 80-83%, indicating similar recovery and consistent experimental operation. Some resins had less binding capacity than Q FF, while others had higher binding capacities. In particular, Fractogel demonstrated highest binding capacity, best selectivity among all the resins tested and comparable recovery. Furthermore, very little product loss was observed in the flow-through for Fractogel at a loading of 15 g/L.

Exemplary results showing the yield and binding capacity of Q FF and Fractogel resin are shown in Table 4.

TABLE 4

Exemplary Results of Binding Capacities and Yield

| Resin | A280 Yield | | | | Binding (AU/L) |
| --- | --- | --- | --- | --- | --- |
| | FT | Wash | Elution/strip | Sum | |
| QFF | 37% | 2% | 42% | 82% | 62 |
| Fractogel | 17% | 2% | 62% | 81% | 83 |

Side-by-Side Confirmation Runs

To verify the Fractogel process and evaluate its impact on subsequent purification steps and final drug substance ("DS") quality, side-by-side purification processes of Fractogel TMAE versus Q FF were performed from unpurified bulk material through to drug substance, inclusive of the chromatographic steps described in the instant examples. The additional purification steps following anion exchange chromatography were as described below (presented in order of execution): HA column mixed mode chromatography, phenyl column hydrophobic interaction chromatography, SP column cation exchange chromatography, and two steps of ultrafiltration/diafiltration with an intervening viral filtration step.

Both A280 and titer yields were comparable. The HCP reductions were also similar across the columns.

Moreover, SDS-PAGE (silver) gels (FIG. 4) showed similar band profiles for both Fractogel and Q FF through the entire process. CE-SDS data showed better purity for Fractogel than Q FF as the first step, but comparable results after the phenyl column step. This was confirmed by the HCP/rhASA ratio.

Quality attributes were assessed for SP eluate from both columns, as well as a control run SP eluate. The Fractogel and Q FF processes provided similarly pure and acceptable SP eluate, although certain attributes differed slightly from the control due to differences in the unpurified load starting materials.

Overall, using Fractogel as first column provided comparable process performance (yields, HCP reduction) and SP quality attributes as the control process using Q FF, as confirmed by the above results. However, the Fractogel column provided a higher loading capacity and increased throughput.

In conclusion, side-by-side confirmation runs showed that the Fractogel TMAE process had comparable performance (yields, HCP removal) to the Q FF process, but provided the added benefit of a higher target loading capacity (e.g., at least 10 g rhASA/L). No significant yield lost was observed for the characterized loading range between 5-20 g/L. Quality attributes of SP eluate from Fractogel run were also comparable to the control Q FF run.

Example 4. Mixed Mode Hydroxyapatite (HA) Chromatography

This example illustrates exemplary conditions for mixed mode hydroxyapatite chromatography that can be used in the purification of recombinant ASA protein.

Specifically, anion exchange chromatography eluate, prepared as above, was subsequently purified by hydroxyapatite (HA) chromatography. A commercially available, ceramic hydroxyapatite Type 1 resin column was prepared. In this example, the column was pre-equilibrated with a 0.250 M sodium phosphate buffer, pH 7.0.

The HA column was operated in bind and eluate modes. The anion exchange eluate was first warmed to ambient temperature and then adjusted to about 0.001 M sodium phosphate prior to loading onto the HA column. rhASA bound to the column at pH 7.0 and was eluted from the column with about 0.04 M sodium phosphate, pH 7.1. The loading, wash and elution were performed at flow rate of about 150 cm/hr. The HA elution was collected via absorbance at 280 nm (A280) set points of 0.5 AU/cm on the ascending side of the peak to 0.25 AU/cm on the descending side of the peak. Exemplary conditions used for HA columns are shown in Table 5.

TABLE 5

Exemplary Conditions Used for HA Columns

| Solutions | Use |
| --- | --- |
| 0.5M NaOH | Sanitization |
| 0.25M Sodium Phosphate, pH 7.0 | Charge and load adjustment |
| 0.001M Sodium Phosphate, 0.02M MES-Tris, 0.26M NaCl, pH 7.0 | Equilibration and wash 1 |
| 0.005M Sodium Phosphate, 0.02M MES-Tris, 0.26M NaCl, pH 7.0 | Wash 2 |
| 0.04M Sodium Phosphate, pH 7.1 | Elution and post use filter chase |
| 0.4M Sodium Phosphate, pH 12 | Strip |
| 0.5M NaOH | Clean |
| 0.1M NaOH | Storage |

Example 5. Hydrophobic Interaction (Phenyl) Chromatography

This example illustrates exemplary conditions for hydrophobic interaction (phenyl) chromatography that can be used in the purification of recombinant ASA protein.

Specifically, HA column chromatography eluate, prepared as above, was subsequently purified by phenyl column chromatography. A commercially available phenyl Sepharose Fast Flow column was packed and prepared for purification of rhASA.

The Phenyl column was operated in the bind and elute mode. After warming up to ambient temperature, the HA eluate was adjusted to about 1.1 M NaCl and to a pH of about 5.6 using 0.5M MES, free acid before being loaded onto the phenyl column rhASA bound to the column at pH 5.6 and was eluted from the column using 0.02M MES-Tris, 0.06M NaCl, pH 7.1. The loading, wash and elution were performed at flow rate of about 150 cm/hr. The phenyl eluate was collected via absorbance at 280 nm (A280) set points of 0.5 AU/cm on the ascending side of the peak to 0.25 AU/cm on the descending side of the peak. Exemplary conditions for phenyl columns are shown in Table 6.

TABLE 6

Exemplary Conditions for Phenyl Columns

| Solutions | Use |
| --- | --- |
| 0.5M NaOH | Sanitization and Clean |
| 0.05M Sodium Phosphate, 1M NaCl, pH 5.6 | Equilibration and wash1 |
| 5M NaCl | Load adjustment |
| 0.5M MES, free acid | Load adjustment |
| 0.02M MES, 0.05M Sodium Phosphate, 0.5M NaCl, pH 5.6 | Wash2 |
| 0.02M MES-Tris, 0.06M NaCl, pH 7.1 | Elution and post use filter chase |
| WFI | Strip |
| 0.01M NaOH | Storage |

Example 6. Cation Exchange Chromatography

This example illustrates exemplary conditions for cation exchange chromatography that can be used in the purification of recombinant ASA protein.

Specifically, phenyl column chromatography eluate, prepared as above, was subsequently purified by cation exchange chromatography. In this example, a SP-650M column (TOYOPEARL) was packed and prepared.

The SP column was operated in the bind and elute mode. The phenyl column eluate was warmed to 16-23° C. and then diluted with WFI to lower the conductivity, and adjusted with about 1 M acetic acid to pH 4.2 before being loaded onto the SP column. rhASA bound to the column at pH 4.2 and was eluted from the column using 0.01 M sodium acetate, 0.01 M acetic acid, 0.05M NaCl, pH 4.5. The loading, wash and elution were performed at flow rate of about 150 cm/hr. The SP elution was collected via absorbance at 280 nm (A280) set points of 0.25 AU/cm on the ascending side of the peak to 0.25 AU/cm on the descending side of the peak. Exemplary conditions for SP columns are shown in Table 7.

TABLE 7

Exemplary Conditions for SP Columns

| Solutions | Use |
| --- | --- |
| 0.5M NaOH | Sanitization and Clean |
| 0.013M Sodium Acetate, 0.007M Acetic Acid, 1M NaCl, pH 4.5 | Pre-equilibration and strip |

TABLE 7-continued

Exemplary Conditions for SP Columns

| Solutions | Use |
|---|---|
| 0.01M Sodium Acetate, 0.01M NaCl, 0.03M Acetic Acid, pH 4.2 | Equilibration and wash |
| 0.01M Sodium Acetate, 0.01M Acetic Acid, 0.05M NaCl, pH 4.5 | Elution and post use filter chase |
| 1M Acetic acid | Load adjustment |
| WFI | Load adjustment |
| 0.01M NaOH | Storage |

Example 7. Ultrafiltration/Diafiltration and Viral Filtration

This example illustrates exemplary conditions for ultrafiltration/diafiltration and viral filtration that can be used in the purification of recombinant ASA protein.

Ultrafiltration/Diafiltration 1

The SP elution pool was concentrated and diafiltered using 10 kDa Hydrosart Sartocon membrane. The product pool was concentrated to approximately 15 mg/mL and diafiltered with 6-8 volumes of 0.01 M sodium phosphate-citrate, 0.137 M NaCl, pH 6.0. The concentrated and diafiltered product pool was then processed through a 0.2 μm filter.

The concentrated/diafiltered pool was 0.2 μm filtered and stored at 2-8° C., typically, for less than about 24 hours.

Viral Filtration

A viral filtration operation may be followed ultrafiltration/diafiltration 1 to remove any viral like particles from the process stream. For example, a filtration train with pump, Planova filter and pressure gauge were setup. The filter was flushed with 1 L of 0.154 M NaCl through the retentate side and then greater than 3 L through the permeate side at a target pressure of 11.0 lb/in². Upon completion, the filter was flushed with 4 L of 0.154 M NaCl to increase product recovery. A gold particle test was performed on the filter post-use to ensure that filter integrity was maintained.

Ultrafiltration/Diafiltration 2

The viral filtered material was concentrated to 15-30 mg/ml and diafiltered with 6-8 diavolumes of diafiltration buffer of 0.154 M NaCl using 10 kDa Hydrosart Sartocon UFDF membrane. Upon completion of diafiltration, the material was further concentrated to 48-50 mg/ml. The system was then flushed with diafiltration buffer. An appropriate amount of system rinse was then added back to the product concentrate to achieve a target final concentration of approximately 40 mg/ml.

Example 8. Single Ultrafiltration/Diafiltration Unit Operation

The process described in Example 7 involves ultrafiltration/diafiltration ("UFDF") of SP column eluate (UFDF1), viral filtration of the UFDF1 concentrate, and a final UFDF of the viral filtrate (UFDF2) to produce pre-final drug substance (DS). An exemplary flow diagram of such processes are shown in FIG. 1.

In this example, additional experiments were conducted to determine the feasibility of removing one of the UFDF unit operations to reduce the overall process time, cost, and potentially increase process yield. Thus, studies were conducted to evaluate the feasibility of performing the viral filtration of the pH-adjusted SP eluate, followed by one single UFDF unit operation to generate pre-final filtered drug substance ("DS").

Studies utilized partially purified source materials that had been previously purified from unpurified bulk material ("UPB") through SP eluate, as described above. SP eluate was used as load for the three UFDF runs performed in the current study including two feasibility experimental runs and one control run of the double UFDF process as described above. The two experimental (a.k.a., feasibility) runs consisted of one UFDF following pH adjustment of the SP eluate pool, and one ultrafiltration/double diafiltration ("UFDFDF"). SP eluate for feasibility runs was pH adjusted to 6.0 and subsequently viral filtered via, e.g., a Planova 20N viral filter. Experimental runs were compared to a control run of UPDF1-viral filtration-UFDF2, as described above.

SP Eluate was adjusted to pH 6.0, viral filtered and allocated into two equal volumes; each experimental feasibility run utilized one of the two viral filtrate pools. An exemplary SP elution pool pH-adjustment buffer formulation was designed as set forth in Table 8. A volume per volume addition method of about 0.075 L adjustment buffer/L of SP Eluate was determined to yield the target pH of about 6.0.

TABLE 8

Exemplary pH Adjustment Buffer

| Chemical Component | Concentration (g/L) | Concentration (mM) |
|---|---|---|
| Sodium Phosphate, Monobasic | 4 | 30 |
| Sodium Phosphate, Dibasic | 58 | 220 |
| Sodium Citrate, Dihydrate | 10 | 34 |
| Sodium Chloride | 77 | 1330 |

Upon receipt of the SP eluate pool for experimental runs, a pH adjustment to 6.0 was performed; the adjustment produced SP eluate with pH 5.98. The pH adjusted SP eluate was then viral filtered on a Planova 20N filter.

Table 9 contains a summary of the individual unit operation step yields. As observed, all UFDF runs exhibited similar A280-based recovery yields. An experimental viral filtration unit operation produced a step yield of 106.6%, indicating that no A280 absorbing protein was lost during filtration. The yield for viral filtration was significant as it verified that pH-adjustment to about 6.0 allowed the 20 nm diameter rhASA octamer molecule to dissociate into the dimeric form. It was thought that in acidic conditions (pH 5.0) the rhASA molecule exists as an octamer, but at neutral pH it dissociates into dimeric form. As the Planova 20N has a pore size of 20 nm, it was important that the rhASA protein molecular conformation was not in the octamer form because octameric rhASA may likely be retained/lost within the viral filter. The step yield data confirmed the feasibility of performing the viral filtration prior to UFDF operation by adjusting the pH of the SP eluate. These yield data indicated that rhASA was not lost during viral filtration, and pH adjustment was an important step in both the efficiency of purification and targeting drug substance formulation pH.

TABLE 9

Step Yield Summary

| Run | Step Yield |
|---|---|
| Feasibility Viral Filtration | 106.6% |
| Experimental Run 1—UFDFDF | 97.5% |

TABLE 9-continued

Step Yield Summary

| Run | Step Yield |
|---|---|
| Experimental Run 2—UFDF | 99.6% |
| Control UFDF1 | 99.3% |
| Control UFDF2 | 98.0% |

Upon completion of the viral filtration, the viral filtrate pool was divided evenly into two portions. One portion was fed into Experimental Run 1 (UFDFDF) and the other fed into Experimental Run 2 (UFDF).

As evidenced below, both experimental runs produced similar average permeability during UF and initial DF segments. Additionally, Experimental 1's second DF segment exhibited similar average permeability to the UF and initial DF segments. The control run UFDF1 and UFDF2 both produced consistently lower average permeability values when compared to the feasibility runs, which may have been caused by variability within the scale of devices utilized.

TABLE 10

Average Permeability and Total Processing Times

| Run | UF Average Permeability (LMH/psi) | DF1 Average Permeability (LMH/psi) | DF2 Average Permeability (LMH/psi) | Total Processing Time (min) |
|---|---|---|---|---|
| Experimental 1; UFDFDF | 2.5 | 2.4 | 2.3 | 86 |
| Experimental 2; UFDF | 2.5 | 2.6 | N/A | 60 |
| Control UFDF1 | 1.6 | 1.5 | N/A | 58 |
| Control UFDF2 | 1.6 | 1.3 | N/A | 48 |

Product quality of the drug substance from the control run and experimental runs were compared by a series of analytical assays including: SEC-HPLC, RP-HPLC, Activity, SDS-PAGE/HCP Western, SDS-PAGE (Coomassie), Glycan Mapping, peptide mapping, and metals analysis.

SEC-HPLC & RP-HPLC

Table 11 provides size exclusion (SEC-HPLC) and reverse phase (RP-HPLC) results. Both SEC and RP data indicated negligible differences between the experimental runs and the control run drug substances, indicating that both experimental runs produced drug substance with SEC and RP main peak percentages comparable to the drug substance from the control run. These data demonstrated the feasibility of utilization of either experimental run in place of the double UFDF control processes, as no discernible difference in purity was identified.

TABLE 11

SEC-HPLC & RP-HPLC Results

| DS Lot | SEC Main Peak % | RP Main Peak % |
|---|---|---|
| Experimental 1; UFDFDF | 98 | 99 |
| Experimental 2; UFDF | 98 | 99 |
| Control | 98 | 99 |

Activity

Table 12 details the activity (U/mL) and the specific activity (U/mg); the concentration (mg/mL) was determined by dividing the absorbance (AU) by the known extinction coefficient of 0.67. While Experimental Run 1 (UFDFDF) was observed to produce the lowest specific activity value, it was also well within the desired specification range of 50-140 U/mg. Experimental Run 2 (UFDF) produced comparable specific activity to the control run. All three runs, two experimental and one control, were comparable, which indicated that the method for obtaining formulated drug substance does not impact drug substance activity.

TABLE 12

Activity and Specific Activity Results

| DS Lot | Activity (U/mL) | Concentration (mg/mL) | Specific Activity (U/mg) |
|---|---|---|---|
| Feasibility 1; UFDFDF | 2683 | 38.7 | 69.3 |
| Feasibility 2; UFDF | 3320 | 39.5 | 84.1 |
| Control | 3658 | 40.4 | 90.5 |

Host Cell Protein (HCP) Western & SDS-PAGE (Coomassie)

Figure 5:
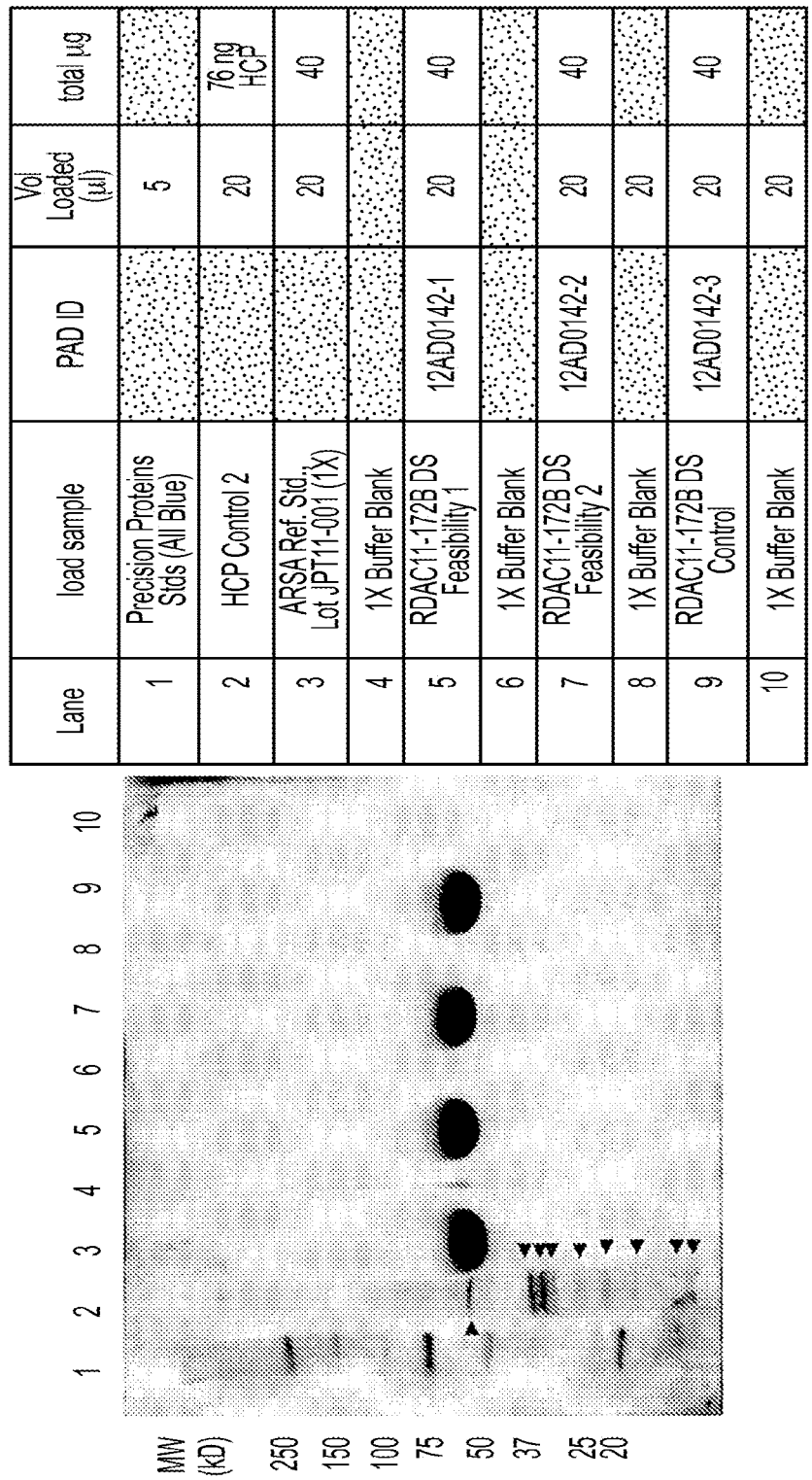
FIG. 5 depicts exemplary results showing that feasibility runs involving single UFDF or UFDFDF step and control runs exhibited similar band patterns as the reference standard (lane 3), indicating that drug substance from all runs exhibited comparably low levels of HCP.
Figure 6:
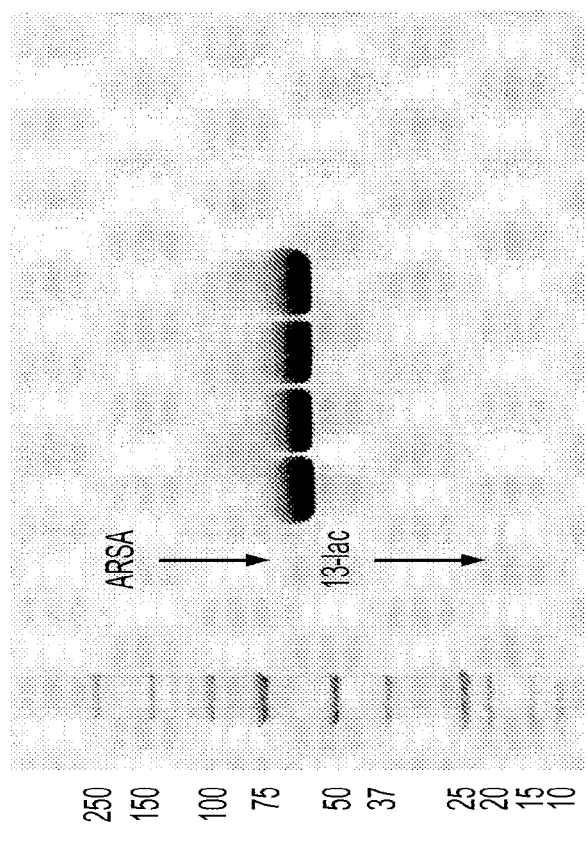
FIG. 6 depicts exemplary results demonstrating comparability between experimental (feasibility) and control runs to the reference standard and that no additional band patterns were detected via SDS-PAGE (Coomassie).

FIGS. 5 and 6 present the SDS-PAGE/HCP Western Blot and SDS-PAGE (Coomassie) gel images, respectively. As observed in FIG. 5, experimental (feasibility) and control run samples (Lanes 5, 7, 9) exhibited similar band patterns as the reference standard (Lane 3), indicating drug substance from all runs exhibited comparably low levels of HCP. FIG. 6 also demonstrated comparability between experimental (feasibility) and control runs to the reference standard; no additional band patterns were detected via SDS-PAGE (Coomassie). These data indicated that the product quality of the drug substance from the experimental run conditions was comparable to that from the control run based on SDS-PAGE/HCP Western Blot and SDS-PAGE (Coomassie) analyses. No HCP bands greater than the intensity of the 15 kDa HCP band of the control were observed in the HPC Western Blot; and no new bands greater than the intensity of the 1% assay control were observed.

Glycan Mapping

Table 13 presents an exemplary glycan map. All glycosylated forms were found to be present at similar levels across all samples tested. The results indicated that the product quality of the drug substance from the experimental (feasibility) runs was comparable to the drug substance of the control run.

TABLE 13

Glycan Map Results

| Form | Peak Group |
|---|---|
| Neutral | 1 |
| 1-SA | 2 |
| capped M6P | 3 |
| 2-SA | 4 |
| 1-M6P | 5 |
| Hybrid | 6 |
| 2-M6P | 7 |

Metals Analysis and pH

A metals analysis on the experimental- and control-produced drug substances (DS) was also performed to determine the level of residual phosphate. Table 14 presents the residual phosphorus and final pH of each drug samples. Residual phosphorus was found to be comparable across all run conditions. pH was also found to be similar regardless of run conditions. As residual phosphate was hypothesized to contribute to maintaining drug substance pH, and the results of the residual phosphorus were consistent with the observation that the pH of all three lots of drug substances was maintained. These data indicated that both experimental (feasibility) runs produce similar levels of residual phosphate in the drug substance as the control run, and all three drug substance lots were able to maintain the target pH of about 6.0 (i.e., 5.5-6.5) in the final formulation.

The metals analysis also detected elevated levels of calcium, as shown in Table 14. The calcium levels were fairly consistent across all samples. Previous research has shown that calcium ions are present in the active site of rhASA, which is important for the enzymatic activity.

TABLE 14

Residual Phosphorous, Calcium and pH Results

| DS Lot | Phosphorous (ppm) | Calcium (ppm) | pH |
|---|---|---|---|
| Feasibility 1; UFDFDF | 29 | 11 | 6.2 |
| Feasibility 2; UFDF | 31 | 10 | 6.1 |
| Control | 33 | 11 | 6.2 |

Peptide Mapping

Peptide mapping analysis was performed. Again, all samples produced similar profiles, suggesting that the run conditions tested yield comparable rhASA peptide map as the control.

Conclusion

The experiments above evaluated the feasibility of viral filtration prior to UFDF operations by pH adjustment of the SP eluate, feasibility of a single UFDF step to replace two UFDF steps, and feasibility of a single diafiltration (versus double filtration) within the post-viral filtration UFDF step.

The high step yield for viral filtration unit operation in the experimental feasibility runs demonstrated the feasibility of viral filtration prior to UFDF operations. As the viral filtrate permitted the passage of the rhASA molecule to the filtrate, two UFDF feasibility runs were performed. As all product quality and process performance metrics indicated comparability of both feasibility runs to the control, a single UFDF step has been determined to be feasible. The results also demonstrated the feasibility of single diafiltration directly into final formulation solution (0.9% saline solution) (experimental feasibility run 2) as the process is able to produce drug substance of comparable quality as produced by both the control and the double diafiltration experiment (experimental feasibility run 1).

Based on these data, it has been determined that a pH adjustment to about 6.0, utilizing for example the buffer formulation contained in Table 4, will produce pH-adjusted SP eluate suitable for viral filtration prior to final UFDF operations. This process, exemplified in FIG. 2, has been shown to be a feasible replacement for processes comprising a UFDF step, followed by viral filtration, followed by another UFDF step. The pH-adjustment-viral filtration-UFDF process has been demonstrated to produce drug substance of comparable quality and purity produced by more complicated, costly and time-consuming processes.

Example 9. Recombinant Human Arylsulfatase A (rhASA) Drug Substance rhASA purified according to the processes described above was formulated to 35-45 mg/ml in a 154 mM NaCl buffer with a pH of about 5.5-6.5.

The peptide and glycan maps of the final drug substance conformed to those described in Example 8. Residual host cell DNA was present in amounts ≤100 pg/mg as determined by the THRESHOLD® DNA assay. Purity determined by reverse phase and size exclusion HPLC indicated greater than 98% and greater than 95% main peak areas, respectively. Western blotting indicated no host cell protein (HCP) bands with intensity greater than the intensity of an approximately 15 kDa HCP band in the assay control. No more than three HCP bands were detected. SDS-PAGE (Coomassie; reduced) analysis conformed to the reference standard with no new bands with intensity greater than the 1% assay control. Specific activity was determined to be 50-140 U/mg.

EQUIVALENTS AND SCOPE

Those skilled in the art will recognize, or be able to ascertain using no more than routine experimentation, many equivalents to the specific embodiments of the invention described herein. The scope of the present invention is not intended to be limited to the above Description, but rather is as set forth in the following claims.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or the entire group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, (e.g., in Markush group or similar format) it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. The publications, websites and other reference materials referenced herein to describe the background of the invention and to provide additional detail regarding its practice are hereby incorporated by reference.

We claim:

1. A method of purifying recombinant arylsulfatase A (ASA) protein, the method comprising
purifying recombinant arylsulfatase A (ASA) protein from an impure preparation by conducting two or more chromatography steps;
pooling eluate from the final chromatography steps;
adjusting the pH of the pooled elute to between 5.8 to 6.4; and
subjecting the pH-adjusted eluate to a single step of post chromatographic ultrafiltration and/or diafiltration,
thereby exchanging the purified recombinant ASA protein directly into a saline-based formulation, and
wherein the method does not comprise more than one ultrafiltration and/or diafiltration step.

2. The method of claim 1, wherein the pH is adjusted to about 6.0.

3. The method of claim 1, wherein the pH is adjusted using a buffer comprising about 0.1-0.5 M sodium phosphate, 0.5-2.5 M sodium chloride and 0.1-0.6 M sodium citrate with pH 7.0.

4. The method of claim 1, wherein a viral filtration is performed before the step of ultrafiltration and diafiltration.

5. The method of claim 1, wherein the ultrafiltration is tangential flow ultrafiltration.

6. The method of claim 1, the last chromatography step is cation-exchange chromatography.

7. The method of claim 6, wherein one or more of anion-exchange chromatography, mixed-mode chromatography, and hydrophobic interaction chromatography are conducted prior to conducting the cation-exchange chromatography.

8. The method of claim 7, wherein the anion-exchange chromatography is Q chromatography.

9. The method of claim 7, wherein the anion-exchange chromatography comprises a TMAE resin.

10. The method of claim 7, wherein the anion-exchange chromatography utilizes a column selected from the group consisting of Q Sepharose™ Fast Flow, Q Sepharose™ High Performance, Q Sepharose™ XL, Capto™ Q, DEAE, TOYOPEARL GigaCap® Q, Fractogel® TMAE, Eshmuno™ Q, Nuvia™ Q, or UNOsphere™ Q.

11. The method of claim 7, wherein the mixed-mode chromatography is hydroxyapatite (HA) chromatography.

12. The method of claim 7, wherein the hydrophobic interaction chromatography is phenyl chromatography.

13. The method of claim 1, wherein conducting one or more chromatography steps comprises conducting anion-exchange chromatography with TMAE resin, HA chromatography, phenyl chromatography and cation-exchange SP chromatography, in that order.

14. The method of claim 1, wherein ultrafiltration uses a membrane filter comprising a pore size with a molecular weight cutoff of at least 10 kDA.

15. The method of claim 1, wherein the purified recombinant ASA protein contains less than 60 ng/mg HCP.

16. The method of claim 1, wherein the purified recombinant ASA protein contains less than 50 pg/mg host cell DNA.

* * * * *